(12) United States Patent
Fischer et al.

(10) Patent No.: US 11,339,241 B2
(45) Date of Patent: *May 24, 2022

(54) WATER-SOLUBLE AND/OR WATER-SWELLABLE HYBRID POLYMER

(71) Applicant: Clariant International Ltd., Muttenz (CH)

(72) Inventors: Dirk Fischer, Hahnheim (DE); Katharina Berz, Seligenstadt (DE); Gundula Starkulla, Mainz (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,025

(22) PCT Filed: Dec. 6, 2017

(86) PCT No.: PCT/EP2017/081681
§ 371 (c)(1),
(2) Date: Jun. 14, 2019

(87) PCT Pub. No.: WO2018/108667
PCT Pub. Date: Jun. 21, 2018

(65) Prior Publication Data
US 2020/0010598 A1 Jan. 9, 2020

(30) Foreign Application Priority Data
Dec. 15, 2016 (EP) .................................... 16204382

(51) Int. Cl.
*C08F 251/00* (2006.01)
*A61K 8/73* (2006.01)
(Continued)

(52) U.S. Cl.
CPC .............. *C08F 251/00* (2013.01); *A61K 8/73* (2013.01); *A61K 8/8158* (2013.01);
(Continued)

(58) Field of Classification Search
None
See application file for complete search history.

(56) References Cited

U.S. PATENT DOCUMENTS 2,614,989 A 10/1952 Hunter
2,809,971 A 10/1957 Bernstein
(Continued)

FOREIGN PATENT DOCUMENTS

CN 101066940 A 11/2007
CN 101636381 A 1/2010
(Continued)

OTHER PUBLICATIONS

Modified Carrageenan. 4. Synthesis and Swelling Behavior of Crosslinked C-g-AMPS Superabsorbent Hydrogel with Antisalt and pH-Responsiveness Properties, Pourjavadi et al., Journal of Applied Polymer Science, vol. 98, 255-263 (2005). (Year: 2005).*
(Continued)

*Primary Examiner* — Peter A Salamon
(74) *Attorney, Agent, or Firm* — Tod A. Waldrop

(57) ABSTRACT

A water-soluble and/or water-swellable hybrid polymer comprising:
(i) from 5 wt.-% to 95 wt.-% water-soluble and/or water-swellable polysaccharide polymer;
(ii) from 5 wt.-% to 95 wt.-% synthetic polymer comprising:
(a) from 90 mol-% to 99.9 mol-%, preferably 95 mol-% to 99.5 mol-% of repeating units according to Formula (1)

(Continued)

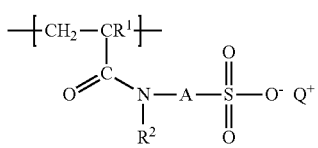

(b) from 0.01 mol-% to 10 mol-%, preferably to 5 mol-%, more preferably to 3 mol-% of crosslinking or branching units, wherein the crosslinking or branching units result from the incorporation of a monomer comprising at least two olefinically unsaturated double bonds;

wherein components (i) and (ii) are polymerized by radical precipitation polymerization in a polar solvent.

15 Claims, 2 Drawing Sheets

(51) Int. Cl.
A61K 8/81 (2006.01)
C08F 220/56 (2006.01)
(52) U.S. Cl.
CPC ........ C08F 220/56 (2013.01); A61K 2800/48 (2013.01); A61K 2800/546 (2013.01); A61K 2800/5424 (2013.01)

(56) References Cited

U.S. PATENT DOCUMENTS

| | | | |
|---|---|---|---|
| 2,865,876 A | 12/1958 | Scott, Jr. | |
| 2,904,580 A | 9/1959 | Idol, Jr. | |
| 2,905,565 A | 9/1959 | Dietz | |
| 3,052,628 A | 9/1962 | Stanberry, Jr. | |
| 3,236,733 A | 2/1966 | Karsten | |
| 3,509,113 A | 4/1970 | Monagle | |
| 3,544,597 A | 12/1970 | Killam | |
| 3,753,196 A | 8/1973 | Kurtz | |
| 3,761,418 A | 9/1973 | Parran | |
| 3,937,721 A | 2/1976 | Schroeck | |
| 3,960,918 A | 6/1976 | Schroeck | |
| 4,015,991 A | 4/1977 | Persinski | |
| 4,138,430 A | 2/1979 | Stiles | |
| 4,323,683 A | 4/1982 | Bolich, Jr. | |
| 4,342,653 A | 8/1982 | Halverson | |
| 4,345,080 A | 8/1982 | Bolich, Jr. | |
| 4,379,753 A | 4/1983 | Bolich, Jr. | |
| 4,470,982 A | 9/1984 | Winkler | |
| 4,487,864 A | 12/1984 | Bermudez | |
| 4,555,269 A | 11/1985 | Rao | |
| 4,655,943 A | 4/1987 | Elmquist | |
| 4,669,920 A | 6/1987 | Dymond | |
| 4,703,801 A | 11/1987 | Fry | |
| 4,722,958 A | 2/1988 | Sauer | |
| 4,800,071 A | 1/1989 | Kaesler | |
| 4,931,489 A | 6/1990 | Kucera | |
| 5,025,040 A | 6/1991 | Crema | |
| 5,104,646 A | 4/1992 | Bolich, Jr. | |
| 5,194,639 A | 3/1993 | Connor | |
| 5,331,021 A | 7/1994 | Ahmed | |
| 5,472,051 A | 12/1995 | Brothers | |
| 5,510,049 A | 4/1996 | Connor | |
| 5,792,828 A | 8/1998 | Quinn | |
| 6,277,900 B1 | 8/2001 | Oswald | |
| 6,297,337 B1* | 10/2001 | Marchant | C08F 6/12 526/324 |
| 6,437,068 B2 | 8/2002 | Loeffler | |
| 6,683,144 B2 | 1/2004 | Loeffler | |
| 6,891,009 B2 | 5/2005 | Loeffler | |
| 7,208,556 B2 | 4/2007 | Loeffler | |
| 8,420,214 B2 | 4/2013 | Kavanagh | |
| 8,629,224 B2 | 1/2014 | Loeffler | |
| 9,399,692 B1 | 7/2016 | Jiang | |
| 9,434,793 B1 | 9/2016 | Kane | |
| 9,611,419 B1 | 4/2017 | Ferrell, Jr. | |
| 2003/0064044 A1 | 4/2003 | Chen | |
| 2004/0228809 A1 | 11/2004 | Birkel | |
| 2005/0003984 A1 | 1/2005 | Himmrich | |
| 2006/0019835 A1 | 1/2006 | Kayser | |
| 2007/0100102 A1 | 5/2007 | Fenchl | |
| 2008/0226577 A1 | 9/2008 | L Alloret | |
| 2010/0048850 A1 | 2/2010 | Dubois | |
| 2010/0274048 A1 | 10/2010 | Wakayama | |
| 2010/0278763 A1 | 11/2010 | Loeffler | |
| 2010/0311904 A1 | 12/2010 | Chambers | |
| 2010/0331904 A1 | 12/2010 | Warren | |
| 2011/0110878 A1 | 5/2011 | Knappe | |
| 2011/0136718 A1 | 6/2011 | Rodrigues | |
| 2011/0318515 A1 | 12/2011 | Dubois | |
| 2012/0039819 A1 | 2/2012 | Nakatani | |
| 2012/0100084 A1* | 4/2012 | Peter | C08F 220/26 424/59 |
| 2012/0138299 A1 | 6/2012 | Joseph | |
| 2013/0043384 A1 | 2/2013 | Matsumoto | |
| 2013/0129652 A1* | 5/2013 | Blin | A61K 8/19 424/63 |
| 2014/0051819 A1 | 2/2014 | Davidson | |
| 2014/0086854 A1 | 3/2014 | Klug | |
| 2014/0127147 A1 | 5/2014 | Klug | |
| 2014/0128513 A1 | 5/2014 | Carlson | |
| 2014/0154758 A1 | 6/2014 | Dubois | |
| 2014/0256880 A1 | 9/2014 | Rodrigues | |
| 2015/0239803 A1 | 8/2015 | Sun | |
| 2015/0329877 A1 | 11/2015 | Bockrath | |
| 2016/0177002 A1 | 6/2016 | Palchik | |
| 2016/0185948 A1 | 6/2016 | Kaneumi | |
| 2016/0190641 A1 | 6/2016 | Lee | |
| 2016/0194416 A1 | 7/2016 | Fukuhara | |
| 2016/0194423 A1 | 7/2016 | Michitaka | |
| 2016/0200670 A1 | 7/2016 | Reb | |
| 2016/0200952 A1 | 7/2016 | Takahara | |
| 2016/0211521 A1 | 7/2016 | Iwayasu | |
| 2016/0214896 A1 | 7/2016 | Cadix | |
| 2016/0222580 A1 | 8/2016 | Shimada | |
| 2016/0236982 A1 | 8/2016 | Menceloglu | |
| 2016/0244594 A1 | 8/2016 | Langlotz | |
| 2016/0244629 A1 | 8/2016 | Xu | |
| 2016/0271988 A1 | 9/2016 | Oharuda | |
| 2016/0272676 A1 | 9/2016 | Mikhail | |
| 2016/0288045 A1 | 10/2016 | Kramer | |
| 2016/0298110 A1 | 10/2016 | Mcgall | |
| 2016/0333199 A1 | 11/2016 | Akkerman | |
| 2016/0333215 A1 | 11/2016 | Kawai | |
| 2016/0340456 A1 | 11/2016 | Mori | |
| 2016/0340540 A1 | 11/2016 | Brust | |
| 2016/0340541 A1 | 11/2016 | Lele | |
| 2016/0340617 A1 | 11/2016 | Orizet | |
| 2016/0346188 A1 | 12/2016 | Singh | |
| 2016/0346395 A1 | 12/2016 | Reineke | |
| 2016/0354771 A1 | 12/2016 | Inomata | |
| 2016/0355624 A1 | 12/2016 | Chen | |
| 2016/0355735 A1 | 12/2016 | Motooka | |
| 2016/0355736 A1 | 12/2016 | Motooka | |
| 2016/0359156 A1 | 12/2016 | Ohkubo | |
| 2016/0367468 A1 | 12/2016 | Graham | |
| 2016/0369025 A1 | 12/2016 | Yukawa | |
| 2017/0001188 A1 | 1/2017 | Choi | |
| 2017/0001382 A1 | 1/2017 | Stepper | |
| 2017/0002152 A1 | 1/2017 | Fonnum | |
| 2017/0009111 A1 | 1/2017 | Bauer | |
| 2017/0015693 A1 | 1/2017 | Carlson | |
| 2017/0022451 A1 | 1/2017 | Tamareselvy | |
| 2017/0029305 A1 | 2/2017 | Gill | |
| 2017/0029548 A1 | 2/2017 | Kawai | |
| 2017/0030015 A1 | 2/2017 | Amin | |
| 2017/0031243 A1 | 2/2017 | Hatakeyama | |
| 2017/0037170 A1 | 2/2017 | Gonzalez | |
| 2017/0037206 A1 | 2/2017 | Antheunis | |

(56) References Cited

U.S. PATENT DOCUMENTS

| | | |
|---|---|---|
| 2017/0037286 A1 | 2/2017 | Lee |
| 2017/0038500 A1 | 2/2017 | Benz |
| 2017/0044287 A1 | 2/2017 | Yahagi |
| 2017/0045819 A1 | 2/2017 | Karasawa |
| 2017/0059990 A1 | 3/2017 | Tsuchimura |
| 2017/0073446 A1 | 3/2017 | Corten |
| 2017/0106013 A1 | 4/2017 | Piergallini |
| 2017/0121567 A1 | 5/2017 | Kawasaki |
| 2017/0123106 A1 | 5/2017 | Chien |
| 2017/0123229 A1 | 5/2017 | Chien |
| 2017/0129812 A1 | 5/2017 | Langlotz |
| 2017/0130076 A1 | 5/2017 | Most |
| 2017/0135941 A1 | 5/2017 | Green |
| 2017/0145244 A1 | 5/2017 | Yang |
| 2017/0158951 A1 | 6/2017 | Liang |
| 2017/0166776 A1 | 6/2017 | Derocher |
| 2017/0174901 A1 | 6/2017 | Okumura |
| 2017/0174905 A1 | 6/2017 | Bohling |
| 2017/0175335 A1 | 6/2017 | Daniels |
| 2017/0198189 A1 | 7/2017 | Panamarathupalayam |
| 2017/0210864 A1 | 7/2017 | Zhao |
| 2017/0210937 A1 | 7/2017 | Okazaki |
| 2017/0214047 A1 | 7/2017 | Naito |
| 2017/0225404 A1 | 8/2017 | Naruse |
| 2017/0226050 A1 | 8/2017 | Voronov |
| 2017/0240799 A1 | 8/2017 | Wei |
| 2017/0242174 A1 | 8/2017 | Ito |
| 2017/0244095 A1 | 8/2017 | Sonobe |
| 2017/0247487 A1 | 8/2017 | Hemmi |
| 2017/0247489 A1 | 8/2017 | Tekobo |
| 2017/0253683 A1 | 9/2017 | Fujiwara |
| 2017/0275408 A1 | 9/2017 | Yang |
| 2017/0275447 A1 | 9/2017 | Junk |
| 2017/0275813 A1 | 9/2017 | Isobe |
| 2017/0283537 A1 | 10/2017 | Hatton |
| 2017/0291971 A1 | 10/2017 | Serrano |
| 2017/0298155 A1 | 10/2017 | Takafuji |
| 2017/0299779 A1 | 10/2017 | Mita |
| 2017/0305855 A1 | 10/2017 | Klun |
| 2017/0306060 A1 | 10/2017 | Fujita |
| 2017/0306195 A1 | 10/2017 | Lachapell |
| 2017/0313801 A1 | 11/2017 | Takeo |
| 2017/0320985 A1 | 11/2017 | Al-Ghamdi |
| 2017/0321050 A1 | 11/2017 | Elanany |
| 2017/0327679 A1 | 11/2017 | Ghosh |
| 2017/0334778 A1 | 11/2017 | Vilinska |
| 2017/0342220 A1 | 11/2017 | Iijima |
| 2017/0348219 A1 | 12/2017 | Uyama |
| 2017/0349679 A1 | 12/2017 | Yashiki |
| 2017/0355873 A1 | 12/2017 | Wu |
| 2017/0361297 A1 | 12/2017 | Yamanaka |
| 2017/0363956 A1 | 12/2017 | Mizuguchi |
| 2017/0369697 A1 | 12/2017 | Yahagi |
| 2017/0369698 A1 | 12/2017 | Suzuki |
| 2018/0002553 A1 | 1/2018 | Harada |
| 2018/0002563 A1 | 1/2018 | Taylor |
| 2018/0008936 A1 | 1/2018 | Martinez |
| 2018/0016739 A1 | 1/2018 | Coppens |
| 2018/0036689 A1 | 2/2018 | Inoue |
| 2018/0037753 A1 | 2/2018 | Dombrowski |
| 2018/0052152 A1 | 2/2018 | Sacha |
| 2018/0057629 A1 | 3/2018 | Letondor |
| 2018/0072932 A1 | 3/2018 | Kaneko |
| 2018/0079158 A1 | 3/2018 | Qiu |
| 2018/0080119 A1 | 3/2018 | Strand |
| 2018/0086936 A1 | 3/2018 | Steiner |
| 2018/0086966 A1 | 3/2018 | Favero |
| 2018/0093113 A1 | 4/2018 | Schade |
| 2018/0111900 A1 | 4/2018 | Miller |
| 2018/0118970 A1 | 5/2018 | Kaur |
| 2018/0118978 A1 | 5/2018 | Yabu |
| 2018/0133662 A1 | 5/2018 | Kang |
| 2018/0133986 A1 | 5/2018 | Harada |
| 2018/0148578 A1 | 5/2018 | Ohta |
| 2018/0148635 A1 | 5/2018 | Shen |
| 2018/0155478 A1 | 6/2018 | Kayser |
| 2018/0163078 A1 | 6/2018 | Sukhishvili |
| 2018/0169296 A1 | 6/2018 | Benz |
| 2018/0171051 A1 | 6/2018 | Junk |
| 2018/0171203 A1 | 6/2018 | Cadix |
| 2018/0171207 A1* | 6/2018 | Fischer .............. C08L 3/02 |
| 2018/0171208 A1 | 6/2018 | Fischer |
| 2018/0179412 A1 | 6/2018 | Bitler |
| 2018/0186993 A1 | 7/2018 | Tanida |
| 2018/0194882 A1 | 7/2018 | Chambrol |
| 2018/0194948 A1 | 7/2018 | Fan |
| 2018/0194969 A1 | 7/2018 | An |
| 2018/0201713 A1 | 7/2018 | Iwasaki |
| 2018/0206484 A1 | 7/2018 | Bittner |
| 2018/0215925 A1 | 8/2018 | Hatanaka |
| 2018/0217294 A1 | 8/2018 | Hyuugaji |
| 2018/0229023 A1 | 8/2018 | Hatakeyama |
| 2018/0229024 A1 | 8/2018 | Hatakeyama |
| 2018/0230256 A1 | 8/2018 | Yamamuro |
| 2018/0237561 A1 | 8/2018 | Hatakeyama |
| 2018/0237567 A1 | 8/2018 | Klee |
| 2018/0240564 A1 | 8/2018 | Hatakeyama |
| 2018/0244609 A1 | 8/2018 | Favero |
| 2018/0244911 A1 | 8/2018 | Iso |
| 2018/0258297 A1 | 9/2018 | Kitou |
| 2018/0273743 A1 | 9/2018 | Sumerlin |
| 2018/0273761 A1 | 9/2018 | Yoshimura |
| 2018/0273774 A1 | 9/2018 | Brown |
| 2018/0290377 A1 | 10/2018 | Talken |
| 2018/0291219 A1 | 10/2018 | Kiyosada |
| 2018/0312739 A1 | 11/2018 | Panamarathupalayam |
| 2018/0321589 A1 | 11/2018 | Tsuchimura |
| 2018/0325789 A1 | 11/2018 | Takemoto |
| 2018/0327585 A1 | 11/2018 | Adkins |
| 2018/0340098 A1 | 11/2018 | Tanabe |
| 2018/0344615 A1 | 12/2018 | Gamez-Garcia |
| 2018/0346626 A1 | 12/2018 | Ying |
| 2018/0346634 A1 | 12/2018 | Cesar |
| 2018/0346804 A1 | 12/2018 | Blazewicz |
| 2018/0348405 A1 | 12/2018 | Chien |
| 2018/0351149 A1 | 12/2018 | Akiike |
| 2018/0353650 A1 | 12/2018 | Bose |
| 2018/0356561 A1 | 12/2018 | Hyugaji |
| 2018/0362689 A1 | 12/2018 | Lucia |
| 2018/0362833 A1 | 12/2018 | Jackson |
| 2019/0058195 A1 | 2/2019 | Hanasaki |
| 2019/0202737 A1 | 7/2019 | Hesselbarth |
| 2019/0241509 A1 | 8/2019 | Kayser |
| 2019/0338060 A1 | 11/2019 | Fischer |
| 2019/0359735 A1 | 11/2019 | Fischer |
| 2020/0009041 A1 | 1/2020 | Fischer |
| 2020/0010598 A1* | 1/2020 | Fischer .............. C08F 2/14 |
| 2020/0017618 A1 | 1/2020 | Fischer |
| 2020/0017619 A1 | 1/2020 | Fischer |
| 2020/0078287 A1 | 3/2020 | Fischer |
| 2020/0095356 A1 | 3/2020 | Fischer |
| 2020/0270506 A1 | 8/2020 | Fischer |

FOREIGN PATENT DOCUMENTS

| | | |
|---|---|---|
| CN | 102351744 A | 2/2012 |
| CN | 102361894 A | 2/2012 |
| CN | 102952044 A | 3/2013 |
| CN | 103492437 A | 1/2014 |
| CN | 103819614 | 5/2014 |
| CN | 104204080 A | 12/2014 |
| CN | 104884628 A | 9/2015 |
| CN | 105694403 A | 6/2016 |
| EP | 0157055 | 10/1985 |
| EP | 0217608 | 4/1987 |
| EP | 0244981 | 11/1987 |
| EP | 0550637 | 7/1993 |
| EP | 0750899 | 1/1997 |
| EP | 0816403 | 1/1998 |
| EP | 1045869 | 10/2000 |
| EP | 1084696 | 3/2001 |
| EP | 1351654 A1 | 10/2003 |
| EP | 2105127 | 9/2009 |
| EP | 2166060 | 3/2010 |

(56) References Cited

FOREIGN PATENT DOCUMENTS

| | | |
|---|---|---|
| JP | 2008084852 A | 4/2008 |
| JP | 2009149536 A | 7/2009 |
| JP | 2010519191 A | 6/2010 |
| JP | 2011506703 A | 3/2011 |
| JP | 2012087256 A | 5/2012 |
| JP | 2014500334 | 1/2014 |
| JP | 2014055232 A | 3/2014 |
| WO | 9206154 | 4/1992 |
| WO | 9507340 | 3/1995 |
| WO | 9800094 | 1/1998 |
| WO | 9924549 | 5/1999 |
| WO | 9926991 | 6/1999 |
| WO | 9966017 | 12/1999 |
| WO | 0226925 | 4/2002 |
| WO | 2009063120 A1 | 5/2009 |
| WO | 2009072480 A | 6/2009 |
| WO | 2010092875 A1 | 8/2010 |
| WO | 2011089709 | 7/2011 |
| WO | 2012084977 A1 | 6/2012 |
| WO | 2012113671 | 8/2012 |
| WO | 2013017262 | 2/2013 |
| WO | 2013113938 A1 | 8/2013 |
| WO | 2013120636 A1 | 8/2013 |
| WO | 2013178668 | 12/2013 |
| WO | 2013178700 | 12/2013 |
| WO | 2014004616 | 1/2014 |
| WO | 2014086780 | 6/2014 |
| WO | 2014088034 | 6/2014 |
| WO | 2015034948 | 3/2015 |
| WO | 2016042011 | 3/2016 |
| WO | 2017220512 | 12/2017 |

OTHER PUBLICATIONS

Adhikary et al, Synthesis, characterization, and application of amylopectin-graft-poly(AM-co-AMPS), Journal of Applied Polymer Science (2012), 126(S1), 6 pages.
Anonymous, "Bio-based material-Wikipedia, the free encyclopedia", (Mar. 12, 2015), URL: https://en.wikipedia.org/wiki/Bio-based_material, (Sep. 1, 2016), XP055299147.
ASTM International, ASTM D6866-12, Standard Test Methods for Determining the Biobased Content of Solid, Liquid, and Gaseous Samples Using Radiocarbon Analysis (2012) (Year: 2012).
Babu, R. P. et al., "Current progress on bio-based polymers and their future trends", Progress in Biomaterials 2013, 2(8), 1-16. (Year: 2013).
Bernd Tieke, "Makromolekulare Chemie Chapters", ISBN 10:3527313796, 2005.
Bernd Tieke, "Makromolekulare Chemie: Eine Einführung", Wiley-VCH, 2. vollständig überarbeitete und erweiterte Auflage (3. Nachdruck 2010) ISBN-13: 978 3-527-31379-2, p. 259-261.
Bianca et al., "Fermentative production of isobutene", Appl Microbiol Biotechnol (2012) 93:1377-1387.
CTFA Cosmetic Ingredient Dictionary, Second Edition, 1977, 3 pages.
CTFA Cosmetic Ingredient Handbook, Second Edition, 1992, 2 pages.
de Jong et al., "Product developments in the bio-based chemicals arena", Biofuels, Bioprod. Bioref. 6:606-624 (2012).
Dräger-Röhrchen & CMS-Handbuch, 17. Auflage, Mar. 2015, 9 pages.
EP1351654B1—Google English Translation (Year: 2003), 19 pages.
George Odian, "Principles of Polymerization", Third Edition, Wiley-Interscience, New York, in chapter 1-4, p. 19 to 24, ISBN 0-471-61020-8, Aug. 1992.

International Cosmetic Ingredient Dictionary, Fifth Edition, 1993.
International Preliminary Report on Patentability for PCT/EP2017/064977, dated Dec. 25, 2018, 7 pages.
International Search Report for App. No. PCT/EP2017/081415, dated Jan. 16, 2018, 3 pages.
International Search Report for App. No. PCT/EP2017/081417, dated Apr. 4, 2018, 2 pages.
International Search Report for App. No. PCT/EP2017/081667, dated Jan. 23, 2018, 3 pages.
International Search Report for App. No. PCT/EP2017/081681, dated Apr. 11, 2018, 3 pages.
International Search Report for PCT/EP2017/06477, dated Aug. 29, 2017, 2 pages.
International Search Report for PCT/EP2017/081665, dated Jan. 23, 2018, 2 pages.
International Search Report for PCT/EP2017/081666, dated Jan. 23, 2018, 2 pages.
Kourosh Kabiri et al.: "Chitosan-modified nanoclay-poly(AMPS) nanocomposite hydrogels with improved gel strength", Polymer International, vol. 58, No. 11, Sep. 10, 2009 (Sep. 10, 2009), pp. 1252-1259, XP055379190.
Le Notre et al., Green Chemistry, Biobased synthesis of acrylonitrile from glutamic acid, 2011, 13, pp. 807-809, (Year: 2011).
M. A. Bañares, M. O. Guerrero-Pérez, "Appl. Catal. B: Environmental", 148-149 (2013) 601-603.
M. O. Guerrero-Pérez, M. A. Bañares, "New Reaction: Conversion of Glycerol into Acrylonitrile", ChemSusChem 1 (2008) 511-513.
M. O. Guerrero-Péreza and M. A. Bañares, "Metrics of acrylonitrile: From biomass vs. petrochemical route", Catalysis Today 239 (2015) 25-30.
Machine Translation of AOI Keigo, et al., Bio-based Polymers Seni Gakkaishi, 2010, vol. 66 No. 4, p. 124-128.
Machine Translation of Netsu Sokutei, 2012, 39(4), p. 143-150.
Masao Kunioka, "Measurement Methods of Biobased Carbon Content for Biomass-Based Chemicals and Plastics", Radioisotopes, 62, 901-925 (2013).
Mithilesh Yadav et al.: "Superabsorbent nanocomposite (alginate-g-PAMPS/MMT): Synthesis, characterization and swelling behavior", Carbohydrate Polymers, Applied Science Publishers, Ltd. Barking, GB, vol. 90, No. 1, May 4, 2012 (May 4, 2012), pp. 165-173, XP028432003.
Rana, V. et al., "Carbohydrate Polymers", 83 (2011) 1031-1047.
Renae Canterbery Pepe et al., International Cosmetic Ingredient Dictionary and Handbook, 9th Edition, 2002, vol. 4, Published by The Cosmetic, Toiletry, and Fragrance Association, 3 pages.
Srivastava et al., "Graft copolymerization of 2- Acrylamideo-2-methyl-1-propane sulphonic acid onto xanthan gum by ascorbic/bromate redox pair," PMSE Preprints (2004), 90, pp. 291-292.
Srivastava et al., Modification of natural polymer via free radical graft copolymerization of 2 acrylamideo-2-methyl-1-propane sulfonic acid in aqueous media and study of swelling and metal ion sorption behaviour, Journal of Applied Polymer Science (2009), 114(3), 1426-1434.
Le Notre et al., "Supporting Information, Biobased synthesis of acrylonitrile from glutamic acid", Green Chemistry, 2011, 13(4), pp. 807-809.
Tateo, F. et al. "Determination of gamma-butyrolactone (GBL) in foods by SBSE-TD/GC/MS". Journal of Food Composition and Analysis 2003, 16, 721-727. (Year: 2003).
Teodorescu, M. et al. "Poly(vinylpyrrolidone)—A Versatile Polymer for Biomedical and Beyond Medical Applications". Polymer-Plastics Technology and Engineering 2015, 54(9), pp. 923-943.
Zhang, Q. et al. "Enhancing the Acetylene Yield from Methane by Decoupling Oxidation and Pyrolysis Reactions: A Comparison with the Partial Oxidation Process". Industrial & Engineering Chemistry Research 2016, 55, 8383-8394 (Year: 2016).

\* cited by examiner

WATER-SOLUBLE AND/OR WATER-SWELLABLE HYBRID POLYMER

FIELD OF THE INVENTION

The present invention relates to a water-soluble and/or water-swellable hybrid polymer.

BACKGROUND OF THE INVENTION

Cleansing and caring for the skin, scalp, and hair is very important for general hygiene e.g. for removal of unwanted materials such as sebum, oils, dirt, makeup, or for moisturisation, colouring or protection. Many cosmetic products require a certain minimum viscosity in order to achieve ease of application to the substrate and/or retention on the substrate to be treated. Many cosmetic products comprise viscosity-increasing or rheology-influencing agents. These are often referred to as thickening agents, thickeners or gelling agents. Thickening agents used in cosmetics or personal hygiene products include viscous liquids such as polyethylene glycol, synthetic polymers such as polyacrylic acid and vegetable gums. In the 1990s, innovative thickeners based on 2-acrylamido-2-methyl-1-propanesulfonic acid (AMPS) and their salts were introduced into the market (EP0816403 and WO98/00094). In both homopolymer and copolymer form (e.g. Aristoflex® AVC from Clariant), such thickeners are superior in many respects to the corresponding polycarboxylates (Carbopols).

Many materials employed in cosmetics are traditionally derived from crude oil. Environmental, economic and sustainability questions are restricting the use of products derived from this limited resource: synthetic surfactants, for example, have been blamed for environmental incidents, particularly vis-à-vis aquatic problems in rivers and lakes. Therefore, there is a desire to identify more sustainable and biodegradeable, yet gentle and effective materials. Indeed, consumers are very interested in "natural" products including products with a high percentage of "natural" compounds and/or compounds that are derived from renewable materials. Consumers perceive compounds derived from natural materials to be gentler and more environmentally friendly. Recent industrial developments in "bio-based" chemicals are summarised, for example, in de Jong et al, "Product developments in the bio-based chemicals arena", Biofuels, Bioprod. Bioref. 6:606-624 (2012).

Compounds derived from natural materials have various other benefits, including increased biodegradability and also more sustainable availability because they are not based on a limited resource. Compounds derived from plant-based resources are particularly useful since the source compound can simply be regrown. Consumers are also particularly comfortable with using compounds derived from well-known plants, especially those that are considered staple products.

US20040228809A1, for example, discloses an aerosol or pump foam product for treating hair, said product comprising a composition for foam production and said composition comprising inter alia at least one cationic cellulose derivative and at least one chitosan. Cellulose and chitosan are both natural polymers (or derivatives thereof) and they are also both polysaccharides. Indeed, chitosan is derived from chitin, which is what the shells of crustaceans are made from.

However, some natural polymers or derivatives thereof have some performance drawbacks, such as leaving residues and/or having poor solubility in an aqueous formulation environment. Attempts have been made to combine 2-acrylamideo-2-methyl-1-propane sulfonic acid monomers with polysaccharides—for example: Srivastava et al, Modification of natural polymer via free radical graft copolymerization of 2-acrylamideo-2-methyl-1-propane sulfonic acid in aqueous media and study of swelling and metal ion sorption behaviour, Journal of Applied Polymer Science (2009), 114(3), 1426-1434; Srivastava et al, Graft copolymerization of 2-Acrylamideo-2-methyl-1-propane sulphonic acid onto xanthan gum by ascorbic/bromate redox pair, PMSE Preprints (2004), 90, 698-699; Adhikary et al, Synthesis, characterization, and application of amylopectin-graft-poly(AM-co-AMPS), Journal of Applied Polymer Science (2012), 126(S1). However, these disclosures do not provide final polymers that have acceptable performance. Furthermore, the polymers provided are not in a form that is sufficiently useful.

There is a need, therefore, for providing polymeric thickening agents that can provide the excellent performance of modern polymers with the increased biodegradability as well as the more sustainable availability of natural-based polymers.

SUMMARY OF THE INVENTION

In a first aspect, the present invention relates to a water-soluble and/or water-swellable hybrid polymer comprising:
  (i) from 5 wt.-% to 95 wt.-% water-soluble and/or water-swellable polysaccharide polymer;
  (ii) from 5 wt.-% to 95 wt.-% synthetic polymer comprising:
    (a) from 90 mol-% to 99.9 mol-%, preferably 95 mol-% to 99.5 mol-% of repeating units according to Formula (1)

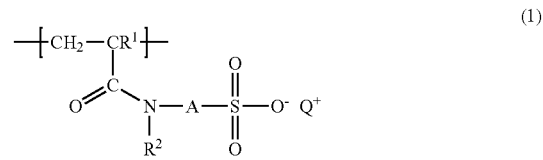

wherein
    $R^1$ and $R^2$ are independently selected from H, methyl or ethyl; A is a linear or branched $C_1$-$C_{12}$-alkyl group; and $Q^+$ is $H^+$, $NH_4^+$, an organic ammonium ion $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear monohydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $Q^+$ is $Li^+$, $Na^+$, $K^+$, $½Ca^{++}$, $½Mg^{++}$, $½Zn^{++}$, $⅓Al^{+++}$, or combinations thereof;
    (b) from 0.01 mol-% to 10 mol-%, preferably to 5 mol-%, more preferably to 3 mol-% of crosslinking or branching units, wherein the crosslinking or branching units result from the incorporation of a monomer comprising at least two olefinically unsaturated double bonds;

characterised in that the components (i) and (ii) are polymerised by radical precipitation polymerisation in a polar solvent.

DETAILED DESCRIPTION OF THE INVENTION

Definitions and General

Figure 1A:
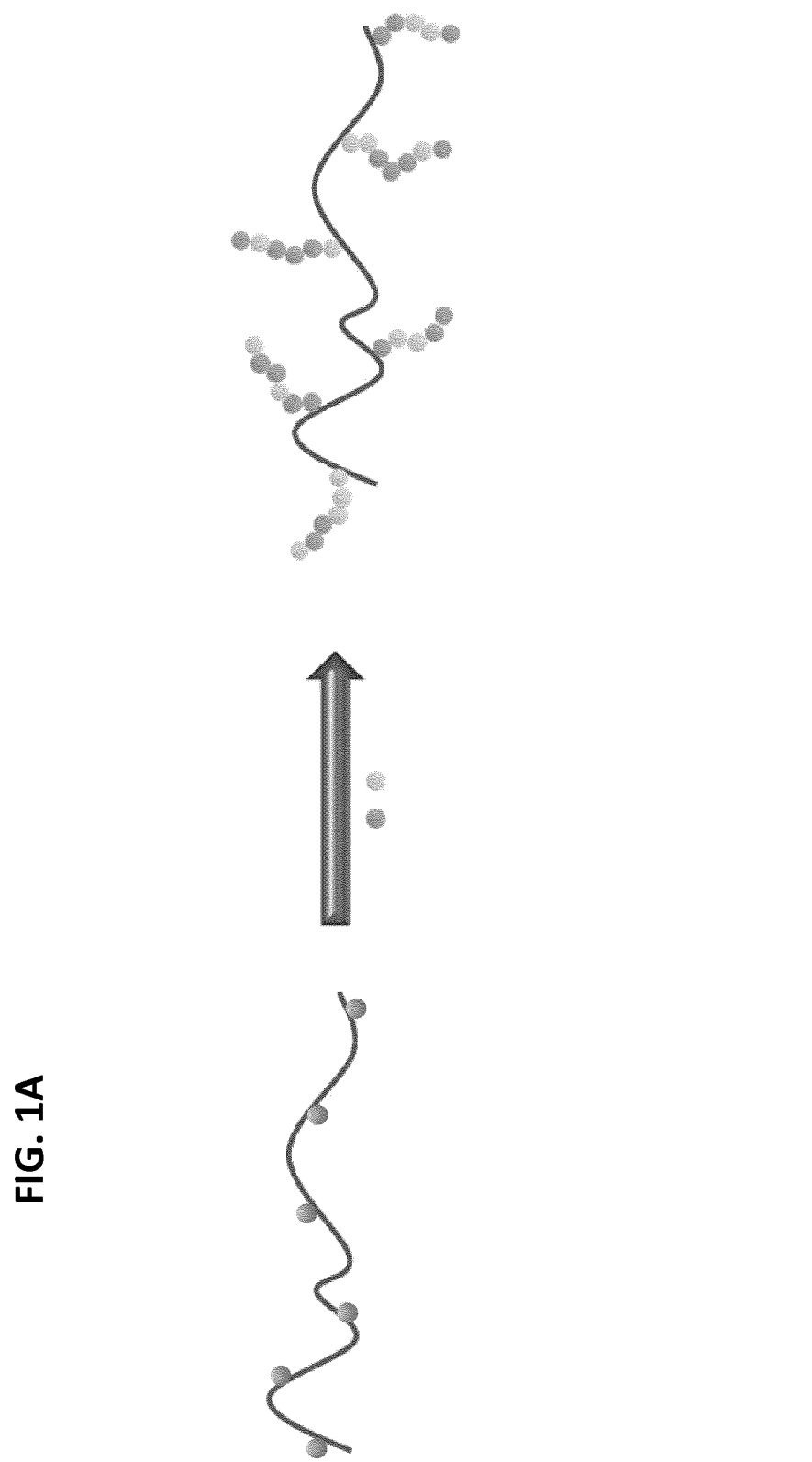
FIG. 1A: Example synthesis of a hybrid polymer. The black line represents a polysaccharide polymer chain. An initiator covalently bonds with suitable sites on the polysaccharide polymer chain. Synthetic monomers are added (see under the arrow). The polysaccharide polymer is grated with synthetic polymers.
Figure 1B:
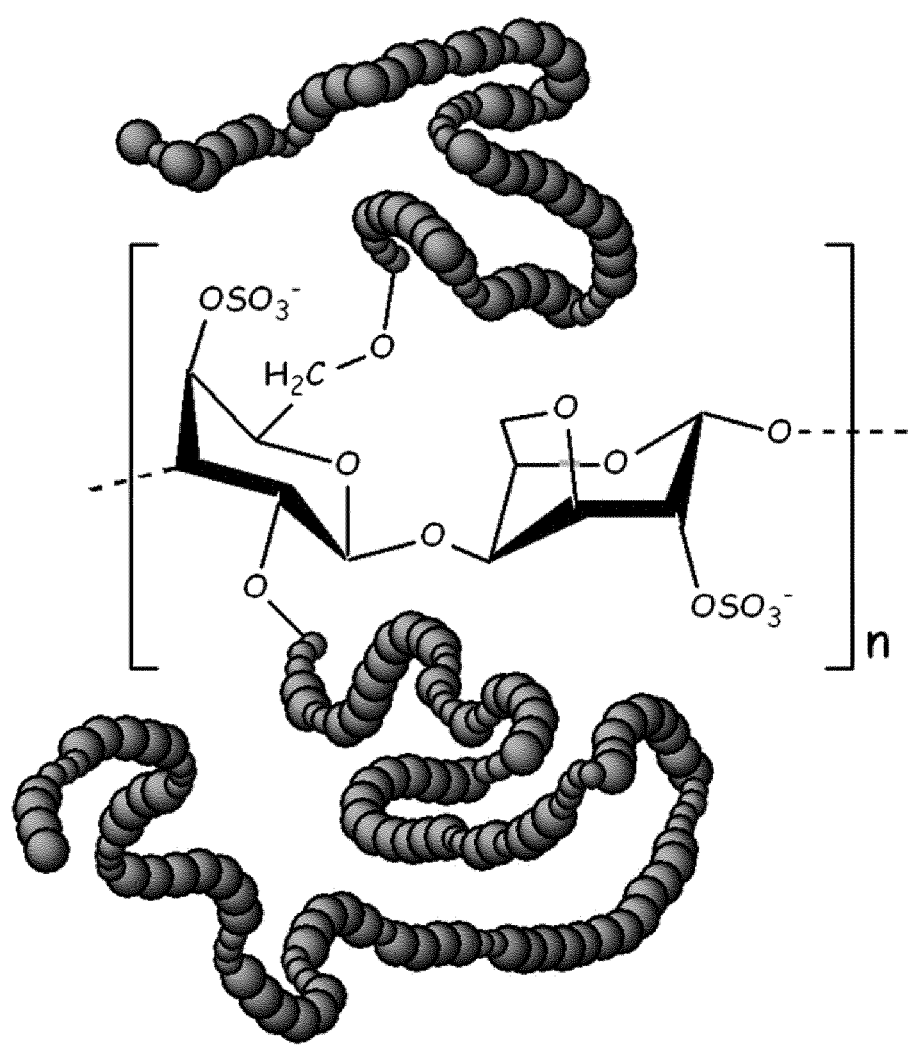
FIG. 1B: Example hybrid polymer. In this case a carrageenan polysaccharide polymer is grafted with synthetic polymers.

In this document, including in all embodiments of all aspects of the present invention, the following definitions apply unless specifically stated otherwise. All percentages are by weight (w/w) of the total composition. "wt.-%" means percentage by weight. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

"Independently selected from," means that the referenced groups can be the same, different, or a mixture thereof, unless the context clearly indicates otherwise. Thus, under this definition, the phrase "X1, X2, and X3 are independently selected from noble gases" would include the scenario where X1, X2, and X3 are all the same, where X1, X2, and X3 are all different, and where X1 and X2 are the same but X3 is different.

"Molecular weight" or "M.Wt." or "MW" and grammatical equivalents mean the weight average molecular weight unless otherwise specifically specified.

Number average molecular weight: Mn

The number average molecular weight is the statistical average molecular weight of all the polymer chains in the sample, and is defined by:

$$Mn = \frac{\sum NiMi}{\sum Ni}$$

where Mi is the molecular weight of a chain and Ni is the number of chains of that molecular weight. Mn can be predicted by polymerisation mechanisms and is measured by methods that determine the number of molecules in a sample of a given weight; for example, colligative methods such as end-group assay. If Mn is quoted for a molecular weight distribution, there are equal numbers of molecules on either side of Mn in the distribution.

Weight average molecular weight: MW

The weight average molecular weight is defined by:

$$MW = \frac{\sum NiMi^2}{\sum NiMi}$$

Compared to Mn, MW takes into account the molecular weight of a chain in determining contributions to the molecular weight average. The more massive the chain, the more the chain contributes to MW. MW is determined by methos that are sensitive to the molecular size rather than just their number, such as light scattering techniques. If MW is quoted for the molecular weight distribution, there is an equal weight of molecules on either side of MW in the distribution.

The polydispersity index PDI is used as a measure of the broadness of a molecular weight distribution of a polymer, and is defined by:

$$PDI = \frac{MW}{Mn}$$

The larger the PDI, the broader the molecular weight. A monodisperse polymer where all the chain lengths are equal (such as a protein) has an MW/Mn=1.

"Viscosity" is measured at 25° C. viscosity in centipoise (cP) using an RVDV Brookfield viscometer with 10-90% torque at 20 RPM, unless otherwise stated.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as radical polymerisation, polycondensation, polyaddition, anionic or cationic polymerization, ring opening polymerisation or coordination insertion polymerisation. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

Explanation of and Benefits provided by the Invention

Surprisingly, it has now been found that hybrid polymers can be synthesised that combine the advantages of modern, synthetic polymers with those of natural or naturally-derived polymers. Furthermore, such hybrid polymers can be synthesised in a one-step process, rather than a process requiring multiple synthesis and/or purification steps. Indeed, the hybrid polymers herein described are polymerised by radical precipitation polymerisation in a polar solvent. This polymerization method results in the production of the hybrid polymer in a convenient form—powder form. Such solid form has the advantage that it is more economical to ship in view of the low weight and high concentration of active material (hybrid polymer), and lack of solvent. Furthermore, being in powder form reduces the risks associated with shipping and/or storing the product in liquid form—in terms of the product degrading in view of the molecules being able to move and react with other molecules such as the container walls and/or microbes being able to survive in the liquid and consume, grow in and/or contaminate the product.

The herein described one-step process providing powder form is achieved in view of the fact that precipitation polymerisation is used i.e. the product of the reaction is produced as an insoluble precipitate—the product crashes out of the reaction mixture. The precipitant thus is no longer soluble in the reaction mixture and thus has no influence on the rheology and viscosity of the reaction mixture.

Conventional radical graft polymerization as disclosed in the prior art results in a highly viscous gel. This has the disadvantage that once a certain viscosity level is reached, it is no longer possible to stir the reaction mixture in order to ensure even distribution of reactants and temperature. The viscosity, however, depends on the natural polymer used. Nevertheless, in most cases the reaction must be stopped relatively early and thus only a low yield of hybrid polymer can be produced.

Furthermore, the reaction product is soluble and thus in solution with solvent. For example, it is not acceptable for formulators using the hybrid polymer in e.g. end-applications to supply them with a 50% solution of hybrid polymer. As a result, with conventional radical graft polymerization as disclosed in the prior art, further processing steps are required in order to remove the solvent from the product and thus increase the concentration level of hybrid polymer versus solvent—indeed it is preferred to remove as much solvent as possible. When considering Srivastava et al (2009), which is cited above in the Background section, it is clear from the section on page 1427 of Srivastava et al (2009) entitled "Procedure for grafting" that precipitation polymerization was not employed since it states that after the reaction has been stopped, the "graft copolymer was precipitated by pouring the reaction mixture into a water—methanol mixture and kept overnight", it is clear that radical precipitation polymerisation as per the present invention has not be employed in Srivastava et al (2009) because a subsequent precipitation step was needed in order to separate the hybrid polymer from the solution. A second disadvantage is that during the drying process of highly viscous gels is that insoluble surface/film-forming coatings and/or non-homogenous clumps result that have a high residual water content. It is not possible to completely exclude and/or remove water from such hybrid polymer produced in this way. Consequently, the present invention provides numerous advantages over the prior art efforts.

The details of the invention and its aspects are provided hereinafter.

First Aspect

The first aspect relates to a water-soluble and/or water-swellable hybrid polymer.

Hybrid Polymer

The water-soluble and/or water-swellable hybrid polymer may herein simply be referred to as 'hybrid polymer', for brevity. The hybrid polymer comprises (i) from 5 wt.-% to 95 wt.-% polysaccharide polymer and (ii) from 5 wt.-% to 95 wt.-% synthetic polymer. In at least one embodiment, the hybrid polymer comprises (i) from 10 wt.-% to 90 wt.-%, or from 15 wt.-% to 85 wt.-%, or from 20 wt.-% to 80 wt.-%, or from 25 wt.-% to 75 wt.-%, 30 wt.-% to 70 wt.-%, or from 35 wt.-% to 65 wt.-%, or from 40 wt.-% to 60 wt.-%, or from 45 wt.-% to 55 wt.-% polysaccharide polymer and (ii) from 10 wt.-% to 90 wt.-%, or from 15 wt.-% to 85 wt.-%, or from 20 wt.-% to 80 wt.-%, or from 25 wt.-% to 75 wt.-%, 30 wt.-% to 70 wt.-%, or from 35 wt.-% to 65 wt.-%, or from 40 wt.-% to 60 wt.-%, or from 45 wt.-% to 55 wt.-% synthetic polymer. In at least one embodiment, the hybrid polymer has a weight ratio of polysaccharide polymer to synthetic polymer of from 70:30; or 60:40; or 50:50; or 40:60; or 30:70; or 20:80; or 10:90. In at least one embodiment, the hybrid polymer comprises at least 30 wt.-% polysaccharide polymer, by total weight of the hybrid polymer.

In at least one embodiment, the hybrid polymer is substantially free of species that release ammonia when the hybrid polymer is used e.g. employed in alkaline cosmetic compositions.

In at least one embodiment, the structure of the hybrid polymer is such that the polysaccharide polymer is a backbone onto which the synthetic polymer is grafted.

In at least one embodiment, the hybrid polymer is a derived natural cosmetic ingredient. According to ISO 16128-1:2016(E) a polymer is a derived natural cosmetic ingredient if it is of greater than 50% natural origin by renewable carbon content. The degree of natural origin can be quantified by renewable carbon content according to analytical procedure ASTM 6866-12, Method B.

Synthetic Polymer

The hybrid polymer comprises a synthetic polymer. "Synthetic polymer" herein means any polymer that is not a naturally-occurring polymer nor a derivative of a naturally-occurring polymer.

The synthetic polymer comprises from 90 mol-% to 99.9 mol-% units (a) and from 0.01 mol-% to 10 mol-% units (b). In at least one embodiment, the synthetic polymer comprises units (a) and units (b) such that the sum thereof is at least 99 mol-%.

In at least one embodiment, the synthetic polymer consists of units (a) and units (b).

Units (a)

The synthetic polymer comprises repeating units according to Formula (1)

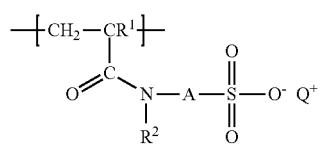

wherein
$R^1$ and $R^2$ are independently selected from H, methyl or ethyl;
A is a linear or branched $C_1$-$C_{12}$-alkyl group; and
$Q^+$ is $H^+$, $NH_4^+$, an organic ammonium ion conforming to $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear mono-hydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $Q^+$ is $Li^+$, $Na^+$, $K^+$, $½Ca^{++}$, $½Mg^{++}$, $½Zn^{++}$, $⅓Al^{+++}$, or combinations thereof.
Preferably $Q^+$ is $H^+$, $NH_4^+$, $Na^+$, or $K^+$. More preferably $Q^+$ is $H^+$, $NH_4^+$, $Na^+$, more preferably $Q^+$ is $NH_4^+$ or $Na^+$.

In at least one embodiment, the synthetic polymer comprises at least one repeating unit (a) according to Formula (1) wherein $R^1$ and $R^2$ are independently selected from H, methyl or ethyl; A is a linear or branched $C_1$-$C_{12}$-alkyl group; and $Q^+$ is $H^+$, $Li^+$, $Na^+$, $K^+$, $½Ca^{++}$, $½Mg^{++}$, $½Zn^{++}$, $⅓Al^{+++}$, or combinations thereof, preferably wherein $Q^+$ is $Na^+$.

In at least one embodiment, $Q^+$ is $NH4^+$. In at least one embodiment, $Q^+$ is selected from the group monoalkylammonium, dialkylammonium, trialkylammonium and/or tetraalkylammonium salts, in which the alkyl substituents of the amines may independently of one another be ($C_1$ to $C_{22}$)-alkyl radicals or ($C_2$ to $C_{10}$)-hydroxyalkyl radicals.

$NH_4^+$ is preferred because it is more soluble the favored solvent used in the polymer synthesis. $Na^+$ is preferred because of reduced likelihood of unpreferred gases being produced during synthesis and also due to economic advantages.

In at least one embodiment, the synthetic polymer comprises at least one repeating unit according to Formula (1). In at least one embodiment, the synthetic polymer comprises two or more different repeating units according to Formula (1), such as repeating units according to Formula (1) having different $Q^+$ counterions.

In at least one embodiment, the repeating units according to Formula (1) result from the incorporation of a monomer selected from the group consisting of acryloyldimethyltaurates, acryloyl-1,1-dimethyl-2methyltaurates, acryloyltaurates, acryloyl-N-methyltaurates, and combinations thereof. Preferably the repeating units according to Formula (1) result from the incorporation of acryloyldimethyltaurate.

In at least one embodiment, the repeating units according to Formula (1) have a degree of neutralisation of between 0 mol-% and 100 mol-%. In at least one embodiment, the repeating units according to Formula (1) have a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80 mol-%, more preferably more than 90 mol-%, even more preferably more than 95 mol-%.

In at least one embodiment, the synthetic polymer comprises from 95 mol-% to 99.9 mol-%, or at least 95.5 mol-%, or at least 96 mol-%, or at least 96.5 mol-%, or at least 97 mol-%, or at least 97.5 mol-%, or at least 98 mol-%, or at least 98.5 mol-%, or at least 99 mol-%, or at least 99.5 mol-% of repeating units according to Formula (1).

Crosslinked and non-crosslinked homo- and co-polymers based on 2-acrylamido-2-methyl-1-propanesulfonic acid (AMPS) monomers and their salts are available from Clariant under their Aristoflex® series.

Units (b)

The synthetic polymer comprises crosslinking or branching units, wherein the crosslinking or branching units result from the incorporation of a monomer comprising at least two olefinically unsaturated double bonds. The synthetic polymer comprises from 0.01 mol-% to 10 mol-%, preferably from 0.01 mol-% to 5 mol-%, more preferably 0.01 mol-% to 3 mol-% of crosslinking or branching units.

In at least one embodiment, the crosslinking or branching units comprise least one oxygen, nitrogen, sulfur or phosphorus atom. In at least one embodiment, the crosslinking or branching units result from monomers having a molecular weight of less than 500 g/mol. In at least one embodiment, the units (b) are bifunctional or trifunctional crosslinking agents.

In at least one embodiment, the synthetic polymer comprises two or more different crosslinking or branching units.

In at least one embodiment, the crosslinking or branching units result from the incorporation of a monomer according to Formula (2):

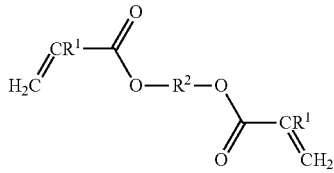

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms.

A monomer according to Formula (2) has the advantage that grafted synthetic polymer can be predicted as a more brush-like synthetic polymer. However brush like synthetic polymers show different properties, as linear ones. For example depending on different comonomer units the solubility could in- or decreased.

In at least one embodiment, the crosslinking or branching units result from the incorporation of a monomer according to Formula (3)

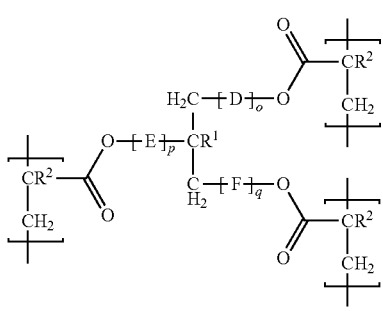

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms;
D, E, and F are independently methyleneoxy (—$CH_2O$), ethyleneoxy (—$CH_2$—$CH_2$—O—), propyleneoxy (—$CH(CH_3)$—$CH_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and
o, p, and q each independently are an integer from 1 to 50.

A monomer according to Formula (3) has the advantage that grafted synthetic polymer can be predicted as a highly branched synthetic polymer. These highly branched grafted synthetic polymer could protect effective the polysaccharide against inadvertently biodegradation.

In at least one embodiment, the crosslinking or branching units result from the incorporation of a crosslinker selected from the group consisting of methylenebisacrylamide; methylenebismethacrylamide; esters of unsaturated monocarboxylic and polycarboxylic acids with polyols, preferably di-acrylates and tri-acrylatees and -methacrylates (e.g. glycerol propoxylate triacrylatee [GPTA]), more preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. In at least one embodiment, the crosslinking or branching units result from the incorporation of trimethylolpropane triacrylatee (TMPTA).

Particularly preferred as crosslinkers for the synthetic polymers of the invention are glycerol propoxylate triacrylate (GPTA), trimethylolpropane triacrylate (TMPTA), pentaerythritol diacrylate mono stearate (PEAS), hexanediol diacrylate (HDDA), and hexanediol dimethacrylate (HDDMA). Especially preferred is glycerol propoxylate triacrylatee (GPTA).

Units (c)

In at least one embodiment, the synthetic polymer comprises at least one neutral repeating structural unit (c).

In at least one embodiment, the synthetic polymer comprises (c) from 0.99 mol-% to 59.99 mol-%, preferably from 1.99 mol-% to 44.99 mol-% of neutral repeating structural units. In at least one embodiment, the synthetic polymer comprises at least one neutral repeating structural unit selected from the group consisting of N-vinylformamide, N-vinylacetamide, N-methyl-N-vinylformamide, N-methyl-N-vinylacetamide, N-vinyl-2-pyrrolidone, N-vinylcaprolactam, vinylacetate, N,N-dimethylacrylamide, N-isopropylacrylamide, acrylamide, methylacrylate, behenylpolyethoxy-(25)-methacrylate, laurylpoly-ethoxy-(7)-methacrylate, cetylpolyethoxy-(10)-methacrylate, stearylpoly-ethoxy-(8)-methacrylate, methoxypoly-ethoxy-(12)-methacrylate, and combinations thereof.

Units (d)

In at least one embodiment, the synthetic polymer comprises at least one anionic repeating structural unit (d).

In at least one embodiment, the synthetic polymer comprises from 1.98 mol-% to 20 mol-%, preferably from 2.5 mol-% to 18 mol-% of anionic repeating structural units, wherein the anionic repeating structural units result from the incorporation of a monomer comprising at least one carboxylate anion, and wherein the anionic repeating structural units are different from units (a).

In at least one embodiment, the anionic repeating structural unit results from the incorporation of monomers according to formula (A):

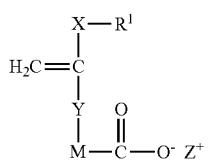

wherein
$R^1$ and $R^3$ are H, methyl or ethyl, or $C(O)O^-Z^+$;
X, Y are selected from a covalent bond, O, $CH_2$, C(O)O, OC(O), $C(O)NR^3$ or $NR^3C(O)$;
M are selected from a covalent bond, —$[C(O)O$—$CH_2$—$CH_2]_n$—, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1-5 and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, $½Ca^{++}$, $½Mg^{++}$, $½Zn^{++}$, $⅓Al^{+++}$, or combinations thereof. In at least one embodiment, the $Z^+$ is $H^+$, $NH_4^+$, $Li^+$, $Na^+$, $K^+$, $½Ca^{++}$, $½Mg^{++}$, $½Zn^{++}$, or $⅓Al^{+++}$, preferably $H^+$, $NH_4^+$, $Li^+$, $Na^+$ or $K^+$.

In at least one embodiment, the synthetic polymer comprises at least one anionic repeating structural unit selected from the group consisting of acrylic acid, methacrylic acid, itaconic acid, carboxyethylacrylate, carboxyethylacrylate oligomers, 2-propylacrylic acid 2-ethylacrylic acid, and their respective alkali or alkaline earth metal salts.

Optional Units (e)

In at least one embodiment, the synthetic polymer comprises at least one optional unit (e). In at least one embodiment, the optional unit results from the incorporation of a monomer selected from the group consisting of unsaturated carboxylic acids and their anhydrides and salts, and also their esters with aliphatic, olefinic, cycloaliphatic, arylaliphatic or aromatic alcohols having a carbon number of from 1 to 22. In at least one embodiment, the optional unit results from the incorporation of at least one monomer selected from the group consisting of functionalised (meth)acrylic acid esters, acrylic or methacrylic acid amidees, polyglycol acrylic or methacrylic acid esters, polyglycol acrylic or methacrylic acid amides, dipropyleneglycolacrylic or methacrylic acid esters, dipropylenglycolacrylic or methacrylic acid amides, ethoxylated fatty alcohol acrylates or -methacrylates, propoxylated fatty alcohol acrylates or linear or cyclic N-vinylamides or N-methylvinyl amides.

In at least one embodiment, the optional unit is an anionic repeating structural unit that results from the incorporation of monomers according to formula (A):

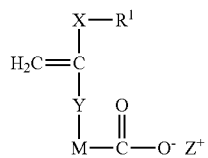

(A)

wherein $R^1$ and $R^3$ are H, methyl or ethyl, or $C(O)O^-Z^+$;

X, Y are selected from a covalent bond, O, $CH_2$, C(O)O, OC(O), $C(O)NR^3$ or $NR^3C(O)$;

M are selected from a covalent bond, $-[C(O)O-CH_2-CH_2]_n-$, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1-5 and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a C6 to C22 alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, $½Ca^{++}$, $½Mg^{++}$, $½Zn^{++}$, $⅓Al^{+++}$, or combinations thereof. In at least one embodiment, the $Z^+$ is $H^+$, $NH_4^+$, $Li^+$, $Na^+$, $K^+$, $½Ca^{++}$, $½Mg^{++}$, $½Zn^{++}$, or $⅓Al^{+++}$, preferably $H^+$, $NH_4^+$, $Li^+$, $Na^+$ or $K^+$.

In at least one embodiment, the optional unit is an anionic structural unit that results from the incorporation of a monomer according to formula (A) wherein X is a covalent bond or is $CH_2$. In at least one embodiment, the optional unit is an anionic structural unit that results from the incorporation of a monomer according to formula (A) wherein Y is a covalent bond, $CH_2$, C(O)O, or $C(O)NR^3$. In at least one embodiment, the optional unit is an anionic structural unit that results from the incorporation of a monomer according to formula (A) wherein M is a covalent bond, $-[C(O)O-CH_2-CH_2]_n-$, a linear or branched alkylene group with 1 to 6 carbon atoms. In at least one embodiment, the optional unit is an anionic structural unit that results from the incorporation of a monomer according to formula (A) wherein $R^1$ is H, methyl or ethyl; X is a covalent bond or is $CH_2$; Y is a covalent bond, $CH_2$, C(O)O, or $C(O)NR^3$; $R^3$ is H, methyl or ethyl; M is a covalent bond, $-[C(O)O-CH_2-CH_2]_n-$, a linear or branched alkylene group with 1 to 6 carbon atoms; $Z^+$ is $H^+$, $NH_4^+$, $Li^+$, $Na^+$, $K^+$, $½Ca^{++}$, $½Mg^{++}$, $½Zn^{++}$, or $⅓Al^{+++}$, or combinations thereof.

In at least one embodiment, the optional unit results from the incorporation of a monomer selected from the group consisting of N-vinylformamide, N-vinylacetamide, N methyl-N-vinylformamide, N-methyl-N-vinylacetamide, N-vinyl-2-pyrrolidone (NVP), N vinylcaprolactam, vinylacetate, methylvinylether, ethylvinylether, methylallylether, ethylmethallylether, styrol, acetoxystyrol, methylmethallylether, ethylallylether, tert-butylacrylamide, N,N-diethylacrylamide, N,N-dimethylacrylamide, N,N-dimethylmethacrylamide, N,N-dipropylacrylamide, N-isopropylacrylamide, N-propylacrylamide, acrylamide, methacrylamide, methylacrylate, methymethylacrylate, tert-butylacrylate, tert-butylmethacrylate, n-butylacrylate, n-butylmethacrylate, laurylacrylate, laurylmethacrylate, behenylacrylate, behenylmethacrylate, cetylacrylate, cetylmethacrylate, stearylacrylate, stearylmethacrylate, tridecylacrylate, tridecylmethacrylate, polyethoxy-(5)-methacrylate, polyethoxy-(5)-acrylate, polyethoxy-(10)-methacrylate, polyethoxy-(10)-acrylate, behenylpolyethoxy-(7)-methacrylate, behenylpolyethoxy-(7)-acrylate, behenylpolyethoxy-(8)-methacrylate, behenylpoly-ethoxy-(8)-acrylate, behenylpolyethoxy-(12)-methacrylate, behenylpoly-ethoxy-(12)-acrylate, behenylpolyethoxy-(16)-methacrylate, behenylpolyethoxy-(16)-acrylate, behenylpolyethoxy-(25)-methacrylate, behenylpolyethoxy-(25)-acrylate, laurylpoly-ethoxy-(7)-methacrylate, laurylpolyethoxy-(7)-acrylate, laurylpolyethoxy-(8)-methacrylate, laurylpolyethoxy-(8)-acrylate, laurylpolyethoxy-(12)-methacrylate, laurylpolyethoxy-(12)-acrylate, laurylpolyethoxy-(16)-methacrylate, laurylpoly-ethoxy-(16)-acrylate, laurylpolyethoxy-(22)-methacrylate, laurylpolyethoxy-(22)-acrylate, laurylpolyethoxy-(23)- methacrylate, laurylpolyethoxy-(23)-acrylate, cetylpolyethoxy-(2)-methacrylate, cetylpolyethoxy-(2)-acrylate, cetyl polyethoxy-(7)-methacrylate, cetyl polyethoxy-(7)-acrylate, cetylpolyethoxy-(10)-methacrylate, cetylpolyethoxy-(10)-acrylate, cetylpolyethoxy-(12)-methacrylate, cetylpolyethoxy-(12)-acrylate cetylpoly-ethoxy-(16)-methacrylate, cetylpolyethoxy-(16)-acrylate cetyl polyethoxy-(20)-methacrylate, cetyl polyethoxy-(20)-acrylate, cetyl polyethoxy-(25)-methacrylate, cetyl polyethoxy-(25)-acrylate, cetyl polyethoxy-(25)-methacrylate, cetyl polyethoxy-(25)-acrylate, stearylpolyethoxy-(7)-methacrylate, stearylpolyethoxy-(7)-acrylate, stearylpoly-ethoxy-(8)-methacrylate, stearylpolyethoxy-(8)-acrylate, stearylpolyethoxy-(12)-methacrylate, stearylpolyethoxy-(12)-acrylate, stearylpoly-ethoxy-(16)-methacrylate, stearylpolyethoxy-(16)-acrylate, stearylpolyethoxy-(22)-methacrylate, stearylpoly-ethoxy-(22)-acrylate, stearylpolyethoxy-(23)-methacrylate, stearylpolyethoxy-(23)-acrylate, stearylpolyethoxy-(25)-methacrylate, stearylpolyethoxy-(25)-acrylate, tridecylpolyethoxy-(7)-methacrylate, tridecylpolyethoxy-(7)-acrylate, tridecylpolythoxy-(10)-methacrylate, tridecylpolyethoxy-(10)-acrylate, tridecylpolyethoxy-(12)-methacrylate, tridecylpolyethoxy-(12)-acrylate, tridecylpolyethoxy-(16)-methacrylate, tridecylpolyethoxy-(16)-acrylate, tridecylpolyethoxy-(22)-methacrylate, tridecylpoly-ethoxy-(22)-acrylate, tridecylpolyethoxy-(23)-methacrylate, tridecylpolyethoxy-(23)-acrylate, tridecylpoly-ethoxy-(25)-methacrylate, tridecylpolyethoxy-(25)-acrylate, methoxypolyethoxy-(7)-methacrylate, methoxy-polyethoxy-(7)-acrylate, methoxypoly-ethoxy-(12)-methacrylate, methoxypolyethoxy-(12)-acrylate, methoxypolyethoxy-(16)-methacrylate, methoxypolyethoxy-(16)-acrylate, methoxypolyethoxy-(25)-methacrylate, methoxypolyethoxy-(25)-acrylate, acrylic acid, ammonium acrylate, sodium acrylate, potassium acrylate, lithium acrylate, zinc acrylate, calcium acrylate, magnesium acrylate, zirconium acrylate, methacrylic acid, ammonium methacrylate, sodium methacrylate, potassium methacrylate, lithium methacrylate, calcium methacrylate, magnesium methacrylatee, zirconium methacrylate, zinc methacrylate, 2-carboxyethylacrylate, ammonium 2-carboxyethylacrylate, sodium 2-carboxyethylacrylate, potassium 2-carboxyethylacrylate, lithium 2 carboxyethylacrylate, zinc 2-carboxyethylacrylate, calcium 2-carboxyethylacrylate, magnesium 2-carboxyethylacrylate, zirconium 2-carboxyethylacrylate, 2-carboxyethylacrylate-oligomere, ammonium 2-carboxyethylacrylate-oligomers, sodium 2-carboxyethylacrylate-oligomers, potassium 2-carboxyethylacrylate-oligomers, lithium 2 carboxyethylacrylate-oligomers, zinc 2-carboxyethylacrylate-oligomers, calcium 2-carboxyethylacrylate-oligomers, magnesium 2-carboxyethylacrylate-oligomers, zirconium 2-carboxyethylacrylate-oligomers, itaconic acid, sodium itaconate, potassium itaconate, lithium itaconate, calcium itaconate, magnesium itaconate, zirconium itaconate, zinc itaconate, 2-ethylacryl acid, ammonium 2-ethylacrylate, sodium 2-ethylacrylate, potassium 2-ethylacrylate, lithium 2-ethylacrylate, calcium 2-ethylacrylate, magnesium 2-ethylacrylate, zirconium 2-ethylacrylate, zinc 2-ethylacrylate, 2-propylacryl acid, ammonium 2-propylacrylate, sodium 2-propylacrylate, potassium 2-propylacrylate, lithium 2-propylacrylate, calcium 2-propylacrylate, magnesium 2-propylacrylate, magnesium 2-propylacrylate, zirconium 2-propylacrylate, zinc 2-propylacrylate, glycerin propoxylate triacrylate (GPTA), trimethylolpropane triacrylate (TMPTA), pentaerythritoldiacrylate monostearate (PEAS), polyethyleneglycol diacrylate, hexanediol diacrylate (HDDA), hexanediol dimethacrylate (HDDMA), and combinations thereof.

In a preferred embodiment, the optional unit results from the incorporation of a monomer selected from the group consisting of glycerine propoxylate triacrylate (GPTA) and trimethylolpropantriacrylate (TMPTA). In a preferred embodiment, the optional unit results from the incorporation of a monomer selected from the group consisting of N-vinylformamide, N-vinylacetamide, N-methyl-N-vinylacetamide, N-vinyl-2-pyrrolidone (NVP), N,N-diethylacrylamide, acrylamide, methacrylamide, methylacrylate, methylmethacrylate, tert-Butylacrylate, acrylic acid, methacrylic acid, 2-carboxyethylacrylate, 2-carboxyethylacrylate oligomers, itaconic acid glycerine propoxylate triacrylate (GPTA), trimethylolpropane triacrylate (TMPTA), pentaerythritol diacrylate monostearate (PEAS) and polyethyleneglycol diacrylate.

In at least one embodiment, the optional unit results from the incorporation of a monomer selected from the group consisting of acrylic acid, methacrylic acid, styrenesulfonic acid, maleic acid, fumaric acid, crotonic acid, itaconic acid, and senecic acid. In at least one embodiment, the optional unit results from monomers selected from the group consisting of open-chain N-vinyl amides, preferably N-vinylformamide (VIFA), N-vinylmethylformamide, N-vinylmethylacetamide (VIMA) and N-vinylacetamides; cyclic N-vinyl amides (N-vinyl lactams) with a ring size of 3 to 9, preferably N-vinyl pyrrolidones (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacryl amide, hydroxypropylmethacrylamide, and mono[2-(methacryloyloxy)ethyl]succinate; N,N-dimethylaminomethacrylate; diethylaminomethylmethacrylate; acrylamideo- and methacrylamideoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; tetrafluoroethylene; and combinations thereof.

Polysaccharide Polymer

The hybrid polymer comprises polysaccharide polymer. The polysaccharide polymer is water-soluble and/or water-swellable. In at least one embodiment, the polysaccharide polymer absorbs water and/or forms a gel or gum when immersed in water. In at least one embodiment, the polysaccharide polymer is a natural gum or mucilage. Natural gums are useful because they are generally soluble in water due to the presence of an excessive number of —OH moieties which form hydrogen bonds with water molecules. Suitable gums are disclosed in Rana, V. et al, Carbohydrate Polymers 83 (2011) 1031-1047 (see, in particular, Table 1). In at least one embodiment, the polysaccharide polymer is a natural gum derived from a plant.

In at least one embodiment, the polysaccharide polymer is selected from the group consisting of chitosan, xanthan gum, fenugreek gum, tara gum, locust bean gum, carrageenan, guar gum, alginate, agar, gum tragacanth, tamarind kernel gum, gum arabica, cherry gum, gum karaya, okra gum, gum cassia, Chicle gum, konjac gum glucomannan, gum ghatti, pectin, sclerotium gum, gellan gum, derivatives thereof, and combinations thereof. Chemically modified versions of such polymers may also be used.

"Modified polysaccharides" means that the polysaccharide polymer treated by one or more suitable physical, enzymatic or chemical process into another modified form of the polysaccharide polymer.

A modified form of the polysaccharide polymer treat by a suitable physical, enzymatic or chemical process mean e.g.:
- Acidic treatment of polysaccharide polymer by the reaction with Acids (e.g. hydrochloric acid, phosphoric acid, or sulphuric acid)
- Alkaline treatment of polysaccharide polymer by the reaction with bases (e.g. Sodium hydroxide or potassium hydroxide)
- bleached polysaccharide polymer by the reaction with peracetic acid, hydrogene peroxide, sodium hypochlorite, sulfur dioxide, sulphites, potassium permanganate or ammonium persulfate.
- Enzymatic modified form of the polysaccharide polymer by the treatment with encymes.
- oxidised polysaccharide polymer by oxidation (e.g. with Sodium hypochlorite)
- acetylated polysaccharide polymer by esterification with e.g. anhydrides
- hydroxypropyl Polysaccharide by reaction with propylene oxide
- hydroxyethyl Polysaccharide by reaction with ethylene oxide Chitosan is a linear polysaccharide composed of randomly distributed β-linked D-glucosamine and N-acetyl-D-glucosamine monomers. Xanthan gum is composed of pentasaccharide repeat units, comprising glucose, mannose, and glucuronic acid in the molar ratio of about 2.0:2.0:1.0. Fenugreek gum is, as its name suggests, derived from fenugreek and is a galactomannan where the ratio of mannose:galactose is approximately 1:1. Tara gum is a galactomannan and comes from the small tree or thorny shrub having the latin name Caesalpinia spinosa. The ratio of mannose:galactose in tara gum is approximately 3:1. Locust bean gum is a galactomannan vegetable gum extracted from the seeds of the carob tree. Locust bean gum consists mainly of high-molecular-weight hydrocolloidal polysaccharides composed of galactose and mannose units combined through glycosidic linkages. Carrageenan is a linear sulfated polysaccharide that are extracted from red edible seaweeds. There are three main varieties of carrageenan, which differ in their degree of sulfation: kappa-carrageenan has one sulfate group per disaccharide; iota-carrageenan has two sulfates per disaccharide; lambda carrageenan has three sulfates per disaccharide. All carrageenans are high-molecular weight polysaccharides made up of repeating galactose units and 3,6-anhydrogalactose, both sulfated and non-sulfated. The units are joined by alternating α-1,3 and β-1,4 glycosidic linkages. Guar gum is a polysaccharide composed of the sugars galactose and mannose: the backbone is a linear chain of β 1,4-linked mannose residues to which galactose residues are 1,6-linked at every second mannose, forming short side-branches. Guar gum is primarily the groand endosperm of guar beans. Alginate may also be referred to in the literature as algin or alginic acid. Alginate is an anionic polysaccharide derived from brown algae and is a linear copolymer with homopolymeric blocks of (1-4)-linked β-D-mannuronate residues and α-L-guluronate residues. Agar is derived from the polysaccharide agarose, which forms the supporting structure in the cell walls of certain species of algae. Agar is actually the resulting mixture of two components: the linear polysaccharide agarose, and a heterogeneous mixture of smaller molecules called agaropectin. Agarose is a linear polymer made up of the repeating unit of agarobiose, which is a disaccharide made up of D-galactose and 3,6-anhydro-L-galactopyranose. Gum tragacanth is a natural gum obtained from the dried sap of several species of Middle Eastern legumes of the genus Astragalus. Gum tragacanth is made up of two types of polysaccharide fractions: tragacanthin and bassorin. Tragacanthin is water-soluble and bassorin is water-swellable. The polysaccharide fractions of gum tragacanth comprise D-galacturonic acid, D-galactose, L-fructose, D-xylose and L-arabinose. Tamarind kernel gum is a polysaccharide of glucose, galactose and xylose in a molar ratio of about 3:2:1. The backbone of the tamarind seed gum polysaccharide is based on a glucose units that are substituted with galactose and xylose. Gum Arabica comes from the Acacia tree. Both gum Arabica and gum ghatti comprise arabinogalactan polysaccharide, which consists of arabinose and galactose monosaccharides. Konjac glucomannan is a non-ionic polysaccharide foand in the tubers of Amorphophallus konjac and consists of (1,4)-linked β-D-mannose and β-D-glucose in a molar ratio of about 1.6:1.

In at least one embodiment, the polysaccharide polymer comprises glucose and/or galactose units. In at least one embodiment, the polysaccharide polymer is a galactomannan. Galactomannans are polysaccharides consisting of a mannose backbone with galactose side groups (more specifically, a (1-4)-linked beta-D-mannopyranose backbone with branchpoints from their 6-positions linked to alpha-D-galactose, i.e. 1-6-linked alpha-D-galactopyranose). In at least one embodiment, the polysaccharide polymer is a guar gum or a guar gum derivative. In at least one embodiment, the guar gum derivative is selected from the group consisting of hydroxypropyl guar gum, carboxymethyl guar gum, carboxymethyl hydroxypropyl guar gum, and quaternary ammonium guar gum. In at least one embodiment, the polysaccharide polymer is an arabinogalactan.

In at least one embodiment, the polysaccharide polymer is substantially free of starch, amylase, amylopectin, glycogen, cellulose, and derivatives thereof. Cellulose derivatives include for example cellulose ethers, carboxymethylcellulose, hydroxyethylcellulose. Such polysaccharides are either neither water-soluble nor water-swellable, and/or result in hybrid polymers that are not desirable from a performance perspective.

In at least one embodiment, the polysaccharide polymer is selected from the group consisting of chitosan, xanthan gum, locust bean gum, carrageenan, guar gum, alginate, agar, fenugreek gum, konjac gum, derivatives thereof, and combinations thereof. In at least one embodiment, the polysaccharide polymer is selected from the group consisting of xanthan gum, carrageenan, guar gum, chitosan and alginate. In a preferred embodiment, the polysaccharide polymer is selected from the group consisting of xanthan gum, carrageenan, guar gum, and combinations thereof. In a preferred embodiment, the polysaccharide polymer is xanthan gum.

Polymerisation

The hybrid polymer components (i) and (ii) are polymerised by radical precipitation polymerisation in a solvent. Radical precipitation polymerisation has the advantage over other synthesis methods in that it results in a more useful level of polymer branching. In at least one embodiment, the polymerisation is grafting radical precipitation polymerisation.

In at least one embodiment, the radical precipitation polymerization is carried out in a polar solvent mixture comprising:
I) water and
II) a further compound.

In at least one embodiment the compound II) is polar and organic.

In at least one embodiment the compound II) is one or more polar alcohols and one or more ketones.

In a preferred embodiment, the compound II) is selected from the group consisting methanol, ethanol, 1-propanol, 2-propanol, 2-methyl-2-propanol, 1-butanol, 2-butanol, dimethyl ketone, diethyl ketone, pentan-2-one, butanone, tetrahydro pyrane, tetrahydro furane, 2-methyl-tetrahydro furane, 1,3-dioxane, 1,4-dioxane, preferably 2-propanol, 2-methyl-2-propanol, dimethyl ketone, tetrahydro furane, 2-methyl-tetrahydro furane, more preferably 2-methyl-2-propanol and dimethyl ketone.

In a preferred embodiment, the solvent mixture contains from 0.5 up to 10 wt.-%, preferably from 1 up to 8 wt.-% and more preferably from 2 up to 5 wt.-% water.

In a preferred embodiment, the solvent mixture contains from 1 up to 99.5 wt.-%, preferably from 5 up to 95 wt.-% and more preferably from 10 up to 90 wt.-% 2-methyl-2-propanol.

In a preferred embodiment, the polar solvent mixture comprises from 0.5 up to 10 wt.-% water, from 1 up to 98.5 wt.-% 2-methyl-2-propanol and from 1 up to 98.5 wt.-% dimethyl ketone, preferably from 0.5 up to 7.5 wt.-% water, from 5 up to 94.5 wt.-% 2-methyl-2-propanol and from 5 up to 94.5 wt.-% dimethyl ketone.

In at least one embodiment, the monomers resulting in units (a) and/or (b) are/is neutralised with a base prior to the polymerisation, and/or the hybrid polymer after polymerisation is neutralised with a base. In at least one embodiment, the the base is selected from bases comprising an ion selected the group consisting of $Li^+$, $Na^+$, $K^+$, $Ca^{++}$, $Mg^{++}$, $Zn^{++}$, $Al^{+++}$, and combinations thereof; preferably wherein the base is selected from hydroxides, carbonates and hydrogen carbonates comprising an ion selected the group consisting of $Li^+$, $Na^+$, $K^+$, $Ca^{++}$, $Mg^{++}$, $Zn^{++}$, $Al^{+++}$, and combinations thereof.

The preferred embodiments, as well as more detailed and preferred features of the polymerisation, are provided in the eighth aspect, which is combinable and compatible with the first aspect and thus incorporated herein by reference.

Example Embodiments of the First Aspect

In a preferred embodiment, the first aspect relates to a water-soluble and/or water-swellable hybrid polymer comprising:
(i) from 5 wt.-% to 95 wt.-% water-soluble and/or water-swellable polysaccharide polymer;
(ii) from 5 wt.-% to 95 wt.-% synthetic polymer consisting of:
(a) from 95 mol-% to 99.9 mol-% repeating units according to Formula (1)

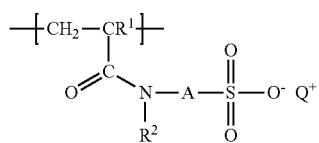

(1)

wherein
$R^1$ and $R^2$ are independently selected from H, methyl or ethyl; A is a linear or branched $C_1$-$C_{12}$-alkyl group; and $Q^+$ is $H^+$, $NH_4^+$, an organic ammonium ion $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear monohydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $Q^+$ is $Li^+$, $Na^+$, $K^+$, ½$Ca^{++}$, ½$Mg^{++}$, ½$Zn^{++}$, ⅓$Al^{+++}$, or combinations thereof;
(b) from 0.01 mol-% to 5 mol-% crosslinking or branching units, wherein the crosslinking or branching units result from the incorporation of a monomer comprising at least two olefinically unsaturated double bonds;
characterised in that the components (i) and (ii) are polymerised by radical precipitation polymerisation in a solvent.

In a preferred embodiment, the first aspect relates to a water-soluble and/or water-swellable hybrid polymer comprising:
(i) from 5 wt.-% to 95 wt.-% water-soluble and/or water-swellable polysaccharide polymer;
(ii) from 5 wt.-% to 95 wt.-% synthetic polymer consisting of:
(a) from 95 mol-% to 99.9 mol-% repeating units resulting from the incorporation of a monomer selected from the group consisting of acryloyldimethyltaurates, acryloyl-1,1-dimethyl-2methyltaurates, acryloyltaurates, acryloyl-N-methyltaurates, and combinations thereof;
(b) from 0.01 mol-% to 5 mol-% crosslinking or branching units, wherein the crosslinking or branching units result from the incorporation of a crosslinking monomer selected from the group consisting of: glycerol propoxylate triacrylatee (GPTA), trimethylolpropane triacrylatee (TMPTA), pentaerythritol diacrylatee mono stearate (PEAS), hexanediol diacrylatee (HDDA), hexanediol dimethacrylatee (HDDMA), and combinations thereof;
characterised in that the components (i) and (ii) are polymerised by radical precipitation polymerisation in a solvent.

Second Aspect

The second aspect relates to a composition. The composition comprises:
(i) a hybrid polymer according to the first aspect;
(ii) a carrier.

In at least one embodiment, the composition is a cosmetic composition. In at least one embodiment, the cosmetic composition is selected from the group consisting of shampoo, body wash, facial cleanser, cleansing masks, bubble bath, intimate wash, bath oil, cleansing milk, micellar water, make-up remover, cleansing wipes, perfume, liquid soaps, shaving soaps, shaving foams, cleansing foams, day creams, night creams, anti-ageing creams, body milks, body lotions, face serums, eye creams, sunscreen sprays, sun care milks, sun care creams, sun care gels, after-shave lotions, pre-shaving creams, depilatory creams, whitening creams, self-tanning creams, anti-acne gels, mascaras, foundations, primers, concealers, bb creams, eyeliners, highlighters, lip stains, hand sanitizers, nail varnish removers, conditioners, hair styling gels, hair styling creams, hair shine serums, scalp treatments, hair colourants, split end fluids, deodorants, antiperspirants, baby creams, insect repellent sprays, hand creams, foot creams, exfoliators, scrubs, and cellulite treatments.

Carrier

A carrier is useful for providing the compounds used in present invention in liquid form. In at least one embodiment, the carrier is a cosmetically acceptable carrier. In at least one embodiment, the composition comprises at least 10 wt.-% water. Water is useful for economic reasons but also because it is highly cosmetically acceptable. Optionally the composition comprises water-miscible or water-soluble solvents such as lower alkyl alcohols. In at least one embodiment, the composition comprises $C_1$-$C_5$ alkyl monohydric alcohols, preferably $C_2$-$C_3$ alkyl alcohols. The alcohols which may be present are in particular lower monohydric or polyhydric alcohols having 1 to 4 carbon atoms customarily used for cosmetic purposes, such as preferably ethanol and isopropanol.

In at least one embodiment, the composition comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof.

In a preferred embodiment, the composition comprises a cosmetically acceptable carrier selected from the group consisting of: water, glycols, ethanol, and combinations thereof.

In a preferred embodiment, the composition comprises an aqueous, alcoholic or aqueous-alcoholic carrier, and wherein the aqueous, alcoholic or aqueous-alcoholic carrier comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic carrier comprises water, isopropanol, 1,2-propylene glycol, 1,3-propylene glycol, or mixtures thereof; even more preferably wherein the aqueous, alcoholic or aqueous-alcoholic carrier consists of water or consists of a mixture of water and an alcohol wherein the alcohol is selected from the group consisting of isopropanol, 1,2-propylene glycol and 1,3-propylene glycol.

Natural carriers can also be used. In at least one embodiment, the composition comprises a carrier selected from the group consisting of plant oil, honey, plant-derived sugar compositions, and mixtures thereof.

Viscosity

In at least one embodiment, the composition has a viscosity of from 0 cPs to 20,000 cPs. In at least one embodiment, the composition has a viscosity of from 0.1 cPs to 10,000 cPs, or from 1 cPs to 5,000 cPs, or from 5 cPs to 3,500 cPs. The viscosity measurement conditions are defined in the definitions section above. Viscosity may be important for anti-drip reasons. Dripping can be inconvenient for the user. Furthermore, more viscous compositions can be useful for measured dispensing. In at least one embodiment, the composition has a viscosity of from 0 cPs to 1,000 cPs. This viscosity range is advantageous when the composition is in the form of a facial cleanser in view of the need for distribution on skin and ability to rinse off.

In at least one embodiment, the composition further comprises a viscosity-modifying substance. The viscosity-modifying substance is preferably a thickening polymer. In at least one embodiment, the thickening polymer selected from the group consisting of: copolymers of at least one first monomer type, which is chosen from acrylic acid and methacrylic acid, and at least one second monomer type, which is chosen from esters of acrylic acid and ethoxylated fatty alcohol; crosslinked polyacrylic acid; crosslinked copolymers of at least one first monomer type, which is chosen from acrylic acid and methacrylic acid, and at least one second monomer type, which is chosen from esters of acrylic acid with $C_{10}$- to $C_{30}$-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated $C_{10}$- to $C_{30}$-alcohol and a third monomer type, chosen from $C_1$-to $C_4$-aminoalkyl acrylates; copolymers of two or more monomers chosen from acrylic acid, methacrylic acid, acrylic esters and methacrylic esters; homopolymers of acryloyldimethyltaurate; crosslinked homopolymers of acryloyldimethyltaurate; copolymers of vinylpyrrolidone and salts of acryloyldimethyltaurate; copolymers of salts of acryloyldimethyltaurate and monomers chosen from esters of methacrylic acid and ethoxylated fatty alcohols; copolymers of salts of acryloyldimethyltaurate, methacrylic acid and monomers chosen from and alkylated acrylamid; salts of acryloyldimethyltaurate and N-vinylpyrrolidone; salts of acryloyldimethyltaurate, methacrylic acid and monomers chosen from esters of methacrylic acid; hydroxyethylcellulose; hydroxypropylcellulose; hydroxypropylguar; glyceryl polyacrylate; glyceryl polymethacrylate; copolymers of at least one $C_2$-, $C_3$- or $C_4$-alkylene and styrene; polyurethanes; hydroxypropyl starch phosphate; polyacrylamide; copolymer of maleic anhydride and methyl vinyl ether crosslinked with decadiene; carob seed flour; guar gum; xanthan; dehydroxanthan; carrageenan; karaya gum; hydrolyzed corn starch; copolymers of polyethylene oxide, fatty alcohols and saturated methylenediphenyl diisocyanate (e.g. PEG-150/stearyl alcohol/SMDI copolymer); and mixtures thereof.

pH

In at least one embodiment, the composition has a pH value of from 2.0 to 12.0, preferably from 3.0 to 9.0, more preferably from 4.5 to 8. By varying the pH value, a composition can be made available that is suitable for different applications.

In at least one embodiment, the composition comprises an alkalizing agent or pH adjusting agent. In at least one embodiment, ammonia or caustic soda is suitable, but water-soluble, physiologically tolerable salts of organic and inorganic bases can also be considered. In at least one embodiment, the pH adjusting agent is selected from ammonium hydrogen carbonate, ammonia, monoethanolamine, ammonium carbonate. In at least one embodiment, the alkalizing agents is selected from the group consisting of 2-amino-2-methyl-1-propanol, 2-amino-2-methyl-1,3-propanediol, 2-amino-2-ethyl-1,3-propanediol, tris(hydroxyl-methyl)-aminomethane, 2-amino-1-butanole, tris-(2-hydroxypropyl)-amine, 2,2-iminobisethanol, lysine, iminourea (guanidine carbonate), tetrahydro-1,4-oxazine, 2-amino-5-guanidin-valeric acid, 2-aminoethansulfonic acid, diethanolamine, triethanolamine, N-methyl ethanolamine, isopropanolamine, diisopropanolamine, triisopropanolamine, glucamine, sodium hydroxide, potassium hydroxide, lithium hydroxide and magnesium oxide, and mixtures thereof.

To establish an acidic pH value, and acid can be included. In at least one embodiment, the composition comprises an acid selected from the group consisting of hydrochloric acid, phosphoric acid, acetic acid, formic acid, sulfuric acid, hydrochloric acid, citric acid, and mixtures thereof. Citric acid is most preferred in that it has high consumer acceptance. In at least one embodiment, the acidic pH is adjusted with a buffer such as a phosphate buffer, a TRIS buffer or a citric buffer. The buffers may be used alone or in combination with an acid.

Form

In at least one embodiment, the composition is in liquid form. In an alternative embodiment, the composition is in solid form. Optionally, the composition is in powdered or granulated form. This is advantageous in that it is not needed to ship liquid, which is typically heavy over long distances, and thus has economic and environmental benefits. A solid form can be achieved by spray drying the composition or the employment of a rotary evaporator. The composition can be converted into liquid form after it has been shipped e.g. by adding water.

Surfactants

In at least one embodiment, the composition comprises a surfactant or surfactant system. In at least one embodiment, the surfactant or surfactant system comprises a surfactant selected from the group consisting of anionic surfactants, cationic surfactants, non-ionic surfactants, zwitterionic surfactants and/or amphoteric surfactants.

In at least one embodiment, the composition comprises a total amount of surfactant of from 0.01 wt.-% to 70 wt.-%, from 0.1 wt.-% to 40%, from 1 wt.-% to 30%, from 2 wt.-% to 20 wt.-%.

In at least one embodiment, the composition comprises an anionic surfactant. In at least one embodiment, the anionic surfactant is selected from the group consisting of ($C_{10}$-$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, acylglutamates, and mixtures thereof. The anionic surfactants (and their mixtures) can be used in the form of their water-soluble or water-dispersible salts, examples being the sodium, potassium, magnesium, ammonium, mono-, di-, and triethanolammonium, and analogous alkylammonium salts. In at least one embodiment, the anionic surfactant is the salt of an anionic surfactant comprising 12 to 14 carbon atoms. In at least one embodiment, the anionic surfactant is selected from the group consisting of sodium lauryl sulfate, sodium laureth sulfate, sodium tridecyl sulfate, sodium trideceth sulfate, sodium myristyl sulfate, sodium myreth sulfate, and mixtures thereof.

In at least one embodiment, the composition comprises an acylglycinate surfactant. In at least one embodiment, the acylglycinate surfactant conforms to the formula (Y):

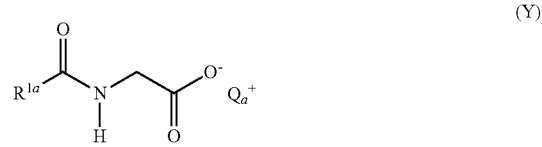

(Y)

wherein $R^{1a}$ is a linear or branched, saturated alkanoyl group having 6 to 30, preferably 8 to 22, particularly preferably 8 to 18, carbon atoms or is a linear or branched, mono- or polyunsaturated alkenoyl group having 6 to 30, preferably 8 to 22 and particularly preferably 12 to 18 carbon atoms, and $Q_a^+$ is a cation. In at least one embodiment, $Q_a^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof. Optionally $R^{1a}$ is, independently from one another, selected from ($C_1$-$C_{22}$)-alkyl radicals or ($C_2$-$C_{10}$)-hydroxyalkyl radicals. In at least one embodiment, the acylglycinate surfactant is selected from sodium cocoylglycinate and potassium cocoylglycinate. In at least one embodiment, the acylglycinate surfactant is selected from those conforming to formula (Y), wherein R is $C_{12}$ alkyl or $C_{14}$ alkyl. In at least one embodiment, the acylglycinate surfactant is selected from those conforming to formula (Y), wherein R is $C_{16}$ alkyl or $C_{18}$ alkyl.

In at least one embodiment, the composition comprises a glutamate surfactant corresponding to formula (Z) or a salt thereof:

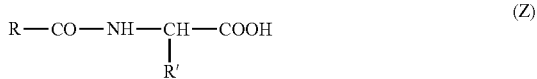

(Z)

wherein
R' is HOOC—$CH_2$—$CH_2$— or $M^+$−OOC—$CH_2$—$CH_2$— wherein $M^+$ is a cation; and wherein R is a linear or branched, saturated alkanoyl group having 6 to 30, preferably 8 to 22, more preferably 8 to 18, carbon atoms or is a linear or branched, mono- or polyunsaturated alkenoyl group having 6 to 30, preferably 8 to 22 and more preferably 12 to 18 carbon atoms. In at least one embodiment, $M^+$ is a metal cation. In at least one embodiment, $M^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof. In at least one embodiment, the glutamate surfactant is selected from sodium cocoyl glutamate and potassium cocoyl glutamate. In at least one embodiment, the glutamate surfactant is selected from those conforming to formula (Z), wherein R is $C_{12}$ alkyl or $C_{14}$ alkyl. In at least one embodiment, the glutamate surfactant is selected from those conforming to formula (Z), wherein R is $C_{16}$ alkyl or $C_{18}$ alkyl.

In at least one embodiment, the composition comprises from 0.01 wt.-% to 30 wt.-%, or 1 wt.-% to 25 wt.-%, preferably from 5 wt.-% to 20 wt.-%, more preferably from 12 wt.-% to 18 wt.-% anionic surfactant.

In at least one embodiment, the composition comprises a non-ionic surfactant.

In at least one embodiment, the non-ionic surfactant has an HLB (Hydrophilic Lipophilic Balance) of greater than 12. Optionally, the non-ionic surfactant is selected from the group consisting of ethoxylated or ethoxylated/propoxylated fatty alcohols with a fatty chain comprising from 12 to 22 carbon atoms, ethoxylated sterols, such as stearyl- or lauryl alcohol (EO-7), PEG-16 soya sterol or PEG-10 soya sterol, polyoxyethylene polyoxypropylene block polymers (poloxamers), and mixtures thereof.

In at least one embodiment, the non-ionic surfactant is selected from the group consisting of ethoxylated fatty alcohols, fatty acids, fatty acid glycerides or alkylphenols, in particular addition products of from 2 to 30 mol of ethylene oxide and/or 1 to 5 mol of propylene oxide onto $C_8$- to $C_{22}$-fatty alcohols, onto $C_{12}$- to $C_{22}$-fatty acids or onto alkyl phenols having 8 to 15 carbon atoms in the alkyl group, $C_{12}$- to $C_{22}$-fatty acid mono- and diesters of addition products of from 1 to 30 mol of ethylene oxide onto glycerol, addition products of from 5 to 60 mol of ethylene oxide onto castor oil or onto hydrogenated castor oil, fatty acid sugar esters, in particular esters of sucrose and one or two $C_8$- to $C_{22}$-fatty acids, INCI: Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate, esters of sorbitan and one, two or three $C_8$- to $C_{22}$-fatty acids and a degree of ethoxylation of from 4 to 20, polyglyceryl fatty acid esters, in particular of one, two or more $C_8$- to $C_{22}$-fatty acids and polyglycerol having preferably 2 to 20 glyceryl units, alkyl glucosides, alkyl oligoglucosides and alkyl polyglucosides having $C_8$ to $C_{22}$-alkyl groups, e.g. decylglucoside or laurylglucoside, and mixtures thereof.

In at least one embodiment, the non-ionic surfactant is selected from the group consisting of fatty alcohol ethoxylates (alkylpolyethylene glycols), alkylphenol polyethylene glycols, alkylmercaptan polyethylene glycols, fatty amine ethoxylates (alkylaminopolyethylene glycols), fatty acid ethoxylates (acylpolyethylene glycols), polypropylene glycol ethoxylates (Pluronics®), fatty acid alkylol amides, (fatty acid amide polyethylene glycols), N-alkyl-, N-alkoxypolyhydroxy-fatty acid amide, sucrose esters, sorbitol esters, polyglycol ethers, and mixtures thereof.

In at least one embodiment, the composition comprises a fatty N-methyl-N-glucamide surfactant. In at least one embodiment, the fatty N-methyl-N-glucamide surfactant conforms to the formula (X):

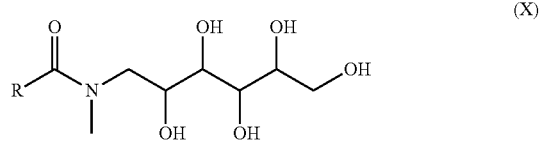

(X)

wherein
R is a linear or branched alkyl or alkenyl group having from 3 to 30 carbon atoms. In at least one embodiment, R is an alkyl group having from 3 to 30 carbon atoms.

In at least one embodiment, R is a saturated aliphatic hydrocarbon group which can be linear or branched and can have from 3 to 20 carbon atoms in the hydrocarbon chain, preferably linear or branched. Branched means that a lower alkyl group such as methyl, ethyl or propyl is present as substituent on a linear alkyl chain. In at least one embodiment, R is selected from the group consisting of 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl. Suitable fatty N-methyl-N-glucamide surfactants are described in WO2013/178700 and EP0550637, which are incorporated herein by reference. In at least one embodiment, the N-methyl-N-glucamide surfactant is selected from those conforming to formula (X), wherein R is $C_{12}$ alkyl or $C_{14}$ alkyl. In at least one embodiment, the N-methyl-N-glucamide surfactant is selected from those conforming to formula (X), wherein R is $C_{16}$ alkyl or $C_{18}$ alkyl. N-methyl-N-glucamide surfactants are available from Clariant under their GlucoTain® brand.

In at least one embodiment, the composition comprises from 1 wt.-% to 20 wt.-%, more preferably from 2 wt.-% to 10 wt.-%, even more preferably from 3 wt.-% to 7 wt.-% non-ionic surfactant.

In at least one embodiment, the amphoteric surfactants are selected from the group consisting of N—($C_{12}$-$C_{18}$)-alkyl- β-aminopropionates and N—($C_{12}$-$C_{18}$)-alkyl-β-iminodipropionates as alkali metal salts and mono-, di-, and trialkylammonium salts; N-acylaminoalkyl-N,N-dimethylacetobetaine, preferably N—($C_8$-$C_{18}$)-acylaminopropyl-N,N-dimethylacetobetaine, ($C_{12}$-$C_{18}$)-alkyl-dimethyl-sulfopropylbetaine, amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., ($C_{12}$-$C_{18}$)-alkyl-dimethyl-amine oxide, fatty acid amidoalkyldimethylamine oxide, and mixtures thereof.

In at least one embodiment, the composition comprises a betaine surfactant. Optionally, the betaine surfactant is selected from $C_8$- to $C_{18}$-alkylbetaines. In at least one embodiment, the betaine surfactant is selected from the group consisting of cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and laurylbis(2-hydroxypropyl)alphacarboxyethylbetaine and combinations thereof. Optionally, the betaine surfactant is selected from $C_8$- to $C_{18}$-sulfobetaines. In at least one embodiment, the betaine surfactant is selected from the group consisting of cocodimethylsulfopropylbetaine, stearyldimethylsulfopropylbetaine, lauryldimethyl-sulfoethylbetaine, laurylbis(2-hydroxyethyl)sulfopropylbetaine, and combinations thereof. Optionally, the betaine surfactant is selected from carboxyl derivatives of imidazole, the $C_8$- to $C_{18}$-alkyldimethylammonium acetates, the $C_8$- to $C_{18}$-alkyldimethylcarbonylmethylammonium salts, and the $C_8$- to $C_{18}$-fatty acid alkylamidobetaines, and mixtures thereof. Optionally, the $C_8$- to $C_{18}$-fatty acid alkylamidobetaine is selected from coconut fatty acid amidopropylbetaine, N-coconut fatty acid amidoethyl-N-[2-(carboxymethoxy)ethyl] glycerol (CTFA name: Cocoamphocarboxyglycinate), and mixtures thereof.

In at least one embodiment, the composition comprises from 0.5 wt.-% to 20 wt.-%, preferably from 1 wt.-% to 10 wt.-% amphoteric surfactant.

In at least one embodiment, the composition comprises a surfactant system. In at least one embodiment, the surfactant system comprises at least one surfactant selected from the group consisting of lauryl sulfate, laureth sulfate, cocoamido-propylbetaine, sodium cocoylglutamate, lauroamphoacetate, and mixtures thereof. In at least one embodiment, the surfactant system comprises sodium laureth sulphate, sodium lauryl sulphate, and optionally cocamidopropyl betaine. In at least one embodiment, the surfactant system comprises sodium laureth sulphate, Potassium Cocyl Glutamate, and cocamidopropyl betaine.

Conditioning Agent

In at least one embodiment, the composition comprises a conditioning agent. In at least one embodiment, the conditioning agent is a water insoluble, water dispersible, nonvolatile, liquid that forms emulsified, liquid particles. In at least one embodiment, the conditioning agent is a silicone (e.g., silicone oil, cationic silicone, silicone gum, high refractive silicone, and silicone resin), an organic conditioning oil (e.g., hydrocarbon oils, polyolefins, and fatty esters), or combinations thereof.

In at least one embodiment, the conditioning agent is a silicone, and wherein the composition comprises from 0.01 wt.-% to 10 wt.-%, or from 0.1 wt.-% to 5 wt.-% silicone conditioning agent, by total weight of the composition. Suitable silicone conditioning agents, and optional suspending agents for the silicone, are described in U.S. Pat. No. 5,104,646. In at least one embodiment, the composition comprises a silicone gum selected from the group consisting of polydimethylsiloxane, (polydimethylsiloxane) (methylvinylsiloxane) copolymer, poly(dimethylsiloxane) (diphenylsiloxane) (methylvinylsiloxane) copolymer, and mixtures thereof.

In at least one embodiment, the composition comprises a terminal aminosilicone. "Terminal aminosilicone" as defined herein means silicone comprising one or more amino groups at one or both ends of the silicone backbone. In at least one embodiment, the composition is substantially free of any silicone compound comprising pendant amino groups. In an embodiment, the composition is substantially free of any silicone compound other than terminal aminosilicones. In at least one embodiment, the amino group at least one terminus of the silicone backbone of the terminal aminosilicone is selected from the group consisting of primary amines, secondary amines and tertiary amines. In at least one embodiment, the composition comprises a terminal aminosilicone conforming to Formula (S):

   (S)

wherein

G is hydrogen, phenyl, hydroxy, or $C_1$-$C_8$ alkyl, preferably methyl;

a is an integer having a value from 1 to 3, preferably 1;

b is 0, 1 or 2, preferably 1;

n is a number from 0 to 1,999;

$R^F$ is a monovalent radical conforming to the general formula $C_qH_{2q}L$, wherein q is an integer having a value from 2 to 8 and L is selected from the following groups: —N($R^T$)$CH_2$—$CH_2$—N($R^T$)$_2$; —N($R^T$)$_2$; —N($R^T$)$_3A^-$; —N($R^T$)$CH_2$—$CH_2$—$NR^TH_2A^-$; wherein $R^T$ is hydrogen, phenyl, benzyl, or a saturated hydrocarbon radical, preferably an alkyl radical from having from 1 to 20 carbon atoms; $A^-$ is a halide ion.

In at least one embodiment, the terminal aminosilicone corresponding to Formula (S) has a=1, q=3, G=methyl, n is from 1000 to 2500, alternatively from 1500 to 1700; and L is —N($CH_3$)$_2$. A suitable terminal aminosilicone corresponding to Formula (S) has a=0, G=methyl, n is from 100 to 1500, or from 200 to 800, and L is selected from the following groups: —N($R^T$)$CH_2$—$CH_2$—N($R^T$)$_2$; —N($R^T$)$_2$; —N($R^T$)$_3A^-$; —N($R^T$)$CH_2$—$CH_2$—$NR^TH_2A^-$; wherein $R^T$ is selected from hydrogen, phenyl, benzyl, or a saturated hydrocarbon radical, preferably an alkyl radical from having from 1 to 20 carbon atoms; $A^-$ is a halide ion, alternatively L is —$NH_2$. In at least one embodiment, the terminal aminosilicone is selected from the group consisting of bis-aminomethyl dimethicone, bisaminoethyl dimethicone, bis-aminopropyl dimethicone, bis-aminobutyl dimethicone, and mixtures thereof. In at least one embodiment, the viscosity of the terminal aminosilicone is from 1,000 to 30,000 cPs, or from 5,000 to 20,000 cPs measured at 25° C.

In at least one embodiment, the composition comprises from 0.1 wt.-% to 20 wt.-%, or from 0.5 wt.-% to 10 wt.-%, or from 1 wt.-% to 6 wt.-% terminal aminosilicone, by total weight of the composition.

In at least one embodiment, the composition comprises a high melting point fatty compound. The high melting point fatty compound has a melting point of 25° C. or higher. In at least one embodiment, the high melting point fatty compound is selected from the group consisting of a fatty alcohol, fatty acid, fatty alcohol derivative, fatty acid derivative, and mixtures thereof. Non-limiting examples of the high melting point compounds are found in International Cosmetic Ingredient Dictionary, Fifth Edition, 1993, and CTFA Cosmetic Ingredient Handbook, Second Edition, 1992. The composition may comprise from 0.1 wt.-% to 40 wt.-%, or from 1 wt.-% to 30 wt.-%, or from 1.5 wt.-% to 16 wt.-%, or from 1.5 wt.-% to 8 wt.-% of a high melting point fatty compound, by total weight of the composition. This is advantageous in view of providing improved conditioning benefits such as slippery feel during the application to wet hair, softness and moisturized feel on dry hair. In at least one embodiment, the fatty alcohol is selected from the group consisting of: cetyl alcohol, stearyl alcohol, behenyl alcohol, and mixtures thereof. In at least one embodiment, the composition comprises a linear fatty alcohol, wherein the linear fatty alcohol is also comprised in a lamellar gel matrix. The lamellar gel matrix is suitable for providing various conditioning benefits such as slippery feel during the application to wet hair and softness and moisturized feel on dry hair. The linear fatty alcohol may comprise from 8 to 24 carbon atoms. In at least one embodiment, the linear fatty alcohol is selected from the group consisting of: cetyl alcohol, stearyl alcohol, and mixtures thereof. In an embodiment, the weight ratio of total linear fatty alcohol to terminal aminosilicone is from 0.5:1 to 10:1, or from 1:1 to 5:1, or from 2.4:1 to 2.7:1. In at least one embodiment, the lamellar gel matrix comprises a cationic surfactant and a high melting point fatty compound. In view of providing the lamellar gel matrix, the cationic surfactant and the high melting point fatty compound are contained at a level such that the weight ratio of the cationic surfactant to the high melting point fatty compound is in the range of from 1:1 to 1:10, or from 1:1 to 1:6.

In at least one embodiment, the composition comprises a cationic surfactant. In at least one embodiment, the composition comprises from 0.05 wt.-% to 3.0 wt.-%, or from 0.075 wt.-% to 2.0 wt.-%, or from 0.1 wt.-% to 1.0 wt.-%, of cationic surfactant by total weight of the composition. In at least one embodiment, the cationic surfactant is comprised in a lamellar gel matrix. In other words, the composition comprises a lamellar gel matrix and the lamellar gel matrix comprises the cationic surfactant. In an embodiment, cationic surfactant is according to Formula (C):

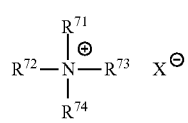

(C)

wherein
at least one of $R^{71}$, $R^{72}$, $R^{73}$ and $R^{74}$ is selected from an aliphatic group of from 8 to 30 carbon atoms, an aromatic, alkoxy, polyoxyalkylene, alkylamido, hydroxyalkyl, aryl, or an alkylaryl group having up to 22 carbon atoms;
the remainder of $R^{71}$, $R^{72}$, $R^{73}$ and $R^{74}$ are independently selected from the group consisting of an aliphatic group consisting of from 1 to 22 carbon atoms, and an aromatic, alkoxy, polyoxyalkylene, alkylamido, hydroxyalkyl, aryl or alkylaryl group having up to 22 carbon atoms;
X is selected from the group consisting of: halogen, acetate, citrate, lactate, glycolate, phosphate, nitrate, sulfonate, sulfate, alkylsulfate, alkyl sulfonate radicals, and combinations thereof.

In at least one embodiment, the cationic surfactant is selected from the group consisting of behenyl trimethyl ammonium chloride, methyl sulfate or ethyl sulfate, and stearyl trimethyl ammonium chloride, methyl sulfate or ethyl sulfate. It is believed that a longer alkyl group provides improved smoothness and soft feeling on wet and dry hair, compared to cationic surfactants with a shorter alkyl group. It is also believed that such cationic surfactants can provide reduced irritation, compared to those having a shorter alkyl group.

In at least one embodiment, the cationic surfactant is a di-long alkyl quatemized ammonium salt selected from the group consisting of: dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In at least one embodiment, the cationic surfactant is a tertiary amido amine having an alkyl group of from 12 to 22 carbons. The tertiary amido amine may be selected from the group consisting of stearamidopropyldimethyl-, stearamidopropyldiethyl-, stearamidoethyldiethyl-, stearamidoethyldimethyl-, palmitamidopropyldimethyl-, palmitamidopropyldiethyl-, palmitamidoethyldiethyl-, palmitamidoethyldimethyl-, behenamidopropyldimethyl-, behenamidopropyldiethyl-, behenamidoethyldiethyl-, behenamidoethyldimethyl-, arachidamidopropy ldimethy 1-, arachidamidopropyldiethyl-, arachidamidoethyldiethyl-, and arachidamidoethyldimethyl-amine, diethylaminoethylstearamide, and mixtures thereof. A tertiary amido amine may be used in combination with an acid. The acid is typically used as a salt-forming anion. In an embodiment, the acid is selected from the group consisting of lactic acid, malic acid, hydrochloric acid, 1-glumatic acid, acetic acid, citric acid, and mixtures thereof.

In at least one embodiment, the cationic surfactant is selected from the group consisting of cetyltrimonium chloride (CTAC), stearyltrimonium chloride (STAC), behentrimonium methosulfate, stearoylamidopropyldimethyl amine (SAPDMA), distearyldimethylammonium chloride, and mixtures thereof.

Hairstyling Polymers

In at least one embodiment, the composition further comprises a hairstyling polymer. In at least one embodiment, the hairstyling polymer is selected from the group consisting of: amphoteric hairstyling polymers, zwitterionic hairstyling polymers, anionic hairstyling polymers, non-ionic hairstyling polymers, cationic hairstyling polymers, and mixtures thereof. In at least one embodiment, the composition comprises from 0.01 wt.-% to 20 wt.-%, or from 0.01 wt.-% to 16 wt.-%, or from 0.01 wt.-% to 10 wt.-%, or from 1 wt.-% to 8 wt.-%, or from 2 wt.-% to 6 wt.-% of hairstyling polymer.

In at least one embodiment, the hairstyling polymer is a water-compatible hairstyling polymer, alternatively a water-soluble hairstyling polymer. In at least one embodiment, the composition is substantially free of a water-incompatible hairstyling polymer. An example of a water-incompatible hairstyling polymer includes an Acrylates/t-Butylacrylamide Copolymer which is a copolymer of tert-butyl acrylamide and one or more monomers of acrylic acid, methacrylic acid, or one of their simple esters (e.g. Ultrahold® 8 from BASF). Balance® CR from Akzo Nobel, which is an acrylates copolymer of two or more monomers of (meth)acrylic acid or one of their simple esters, is water-compatible. The octylacrylamide/acrylate/butylaminoethyl methacrylate copolymer Amphomer® is also water-compatible. In at least one embodiment, the hairstyling polymer is a latex hairstyling polymer.

The composition may comprise a cationic hairstyling polymer. In at least one embodiment, the cationic hairstyling polymers is selected from from group consisting of those with primary, secondary, tertiary or quaternary amino groups. In at least one embodiment, the cationic hairstyling polymer has a cationic charge density, and wherein the cationic charge density is from 1 to 7 meq/g. In at least one embodiment, the cationic hairstyling polymer comprises quaternary amino groups. In at least one embodiment, the cationic hairstyling polymer is a homo- or copolymer where the quaternary nitrogen groups are contained either in the polymer chain or as substituents on one or more of the monomers. The ammonium group-containing monomers can be copolymerized with non-cationic monomers. In at least one embodiment, the cationic hairstyling polymer comprises cationic monomers where the cationic monomers are unsaturated compounds that can undergo radical polymerization and which bear at least one cationic group. In at least one embodiment, the cationic monomers are selected from the group consisting of: ammonium-substituted vinyl monomers such as, for example, trialkylmethacryloxyalkylammonium, trialkylacryloxyalkylammonium, dialkyldiallylammonium and quaternary vinylammonium monomers with cyclic, cationic nitrogen-containing groups such as pyridinium, imidazolium or quaternary pyrrolidones, e.g. alkylvinylimidazolium, alkylvinylpyridinium, or alkylvinylpyrrolidone salts. The alkyl groups of these monomers may be lower alkyl groups such, as for example, $C_1$- to $C_7$-alkyl groups, and may also be are $C_1$- to $C_3$-alkyl groups.

In at least one embodiment, cationic hairstyling polymer comprises ammonium group-containing monomers being copolymerized with non-cationic monomers. The non-cationic monomers may be selected from the group consisting of: acrylamide, methacrylamide, alkyl- and dialkylacrylamide, alkyl- and dialkylmethacrylamide, alkyl acrylate, alkyl methacrylate, vinylcaprolactone, vinylcaprolactam, vinylpyrrolidone, vinyl esters, for example vinyl acetate, vinyl alcohol, propylene glycol or ethylene glycol, and mixture thereof. The alkyl groups of these monomers may be $C_1$- to $C_7$-alkyl groups, and may be $C_1$- to $C_3$-alkyl groups. In at least one embodiment, cationic hairstyling polymer comprises at least one quaternary amino group. Suitable polymers with at least one quaternary amino group include, for example, those described in the CTFA Cosmetic Ingredient Dictionary under the designations 'polyquaternium' such as methylvinylimidazolium chloride/vinylpyrrolidone copolymer (polyquaternium-16) or quaternized vinylpyrrolidone/dimethylaminoethyl methacrylate copolymer (polyquaternium-11; Gafquat® 755N-PW from ISP) as well as quaternary silicone polymers or silicone oligomers such as, for example, silicone polymers with quaternary end groups (quatemium-80).

In at least one embodiment, the hairstyling polymer is a cationic hairstyling polymer being of synthetic origin. In at least one embodiment, the cationic hairstyling polymers of synthetic origin are selected from the group consisting of: poly(dimethyldiallylammonium chloride); copolymers from acrylamide and dimethyldiallylammonium chloride; quaternary ammonium polymers, formed by the reaction of diethyl sulfate with a copolymer from vinylpyrrolidone and dimethylaminoethyl methacrylate, especially vinylpyrrolidone/dimethylaminoethyl methacrylate methosulfate copolymer (e.g. Gafquat® 755 N; Gafquat® 734); quaternary ammonium polymers from methylvinylimidazolium chloride and vinylpyrrolidone (e.g. Luviquat® HM 550 from BASF; Luviquat® Hold from BASF; polyquaternium-46 [vinylcaprolactam {VCap}, vinylpyrrolidone {VP} and quaternized vinylimidazole {QVI}] from BASF; Luviquat® FC 905 from BASF [polyquaternium-16]); Luviquat Supreme® from BASF (polyquaternium-68, quaternised copolymer of vinyl pyrrolidone, methacrylamides, vinyl imidazole and quaternized vinyl imidazole); polyquaternium-35; polyquaternium-57; polymers from trimethylammonium ethyl methacrylate chloride; terpolymers from dimethyldiallylammonium chloride, sodium acrylate and acrylamide (e.g. Merquat® Plus 3300); copolymers from vinylpyrrolidone, dimethylaminopropyl methacrylamide, and methacryloylaminopropyllauryldimethylammonium chloride; terpolymers from vinylpyrrolidone, dimethylaminoethyl methacrylate, and vinylcaprolactam (e.g. Gaffix® VC 713); vinylpyrrolidone/methacrylamidopropyltrimethylammonium chloride copolymers (e.g. Gafquat® HS 100); copolymers from vinylpyrrolidone and dimethylaminoethyl methacrylate; copolymers from vinylpyrrolidone, vinylcaprolactam, and dimethylaminopropylacrylamide; poly- or oligoesters formed from at least one first type of monomer that is selected from hydroxyacids substituted with at least one quaternary ammonium group; dimethylpolysiloxane substituted with quaternary ammonium groups in the terminal positions; and mixtures thereof.

In at least one embodiment, the hairstyling polymer is a cationic hairstyling polymer being of natural origin. In at least one embodiment, the cationic hairstyling polymers being of natural origin are selected from the group consisting of: cationic derivatives of polysaccharides, for example, cationic cellulose derivatives, starch, guar, and mixtures thereof. Cationic derivatives of polysaccharides may be represented by the general formula (D):

$$G\text{-}O\text{---}B\text{---}N^+\text{---}R^a\text{---}R^b\text{---}R^c\ X^- \qquad (D)$$

wherein
  G is an anhydroglucose residue, for example, starch or cellulose anhydroglucoses;
  B is a divalent bonding group, for example, alkylene, oxyalkylene, polyoxyalkylene or hydroxyalkylene;
  $R^a$, $R^b$ and $R^c$ are independently from one another, alkyl, aryl, alkylaryl, arylalkyl, alkoxyalkyl or alkoxyaryl, any of which can have up to 22 carbon atoms, wherein the total number of carbon atoms in $R^a$, $R^b$ and $R^c$ is may be a maximum of 20.

In at least one embodiment, the hairstyling polymer is a cationic cellulose derivative being selected from the group consisting of: those that have at least one quaternary ammonium group, e.g. a copolymer made of hydroxyethyl cellulose and diallyldimethyl ammonium chloride (polyquaternium-4), or the reaction product made of hydroxyethyl cellulose and an epoxide substituted with a trialkyl ammonium group (polyquaternium-10), wherein the alkyl groups can have 1 to 20 carbon atoms, or wherein the alkyl group is methyl. In at least one embodiment, the hairstyling polymer is a cationic cellulose derivative having a molecular weight of from 100,000 Da to 600,000 Da, or from 200,000 Da to 400,000 Da. In at least one embodiment, the cationic cellulose derivative has a nitrogen content, wherein the nitrogen content is from 0.5 wt.-% to 4 wt.-%, or from about 1.5 wt.-% to 3 wt.-%. In at least one embodiment, the hairstyling polymer is a cationic cellulose derivative being polyquaternium-4. Polyquaternium-4 is sold under the trade names Celquat® HIOO and Celquat® L200, of which Celquat® L200 is especially preferred.

In at least one embodiment, the hairstyling polymer is a cationic latex hairstyling polymer. In at least one embodiment, the cationic hairstyling polymer is selected from the group consisting of: polyquaternium-4, polyquaternium-11, polyquaternium-16, polyquaternium-68, mixtures thereof, and mixtures of polyquaternium-68 with a non-ionic hairstyling polymer. In at least one embodiment, the hairstyling polymer is selected from the group consisting of: polyquaternium-4, polyquaternium-11, polyquaternium-68, and mixtures thereof. In at least one embodiment, the composition comprises a chitosan, a chitosan salt or a chitosan derivative. In at least one embodiment, the composition comprises less than 0.1 wt.-% by weight chitosan, chitosan salts and chitosan derivatives. In another embodiment, the composition is substantially free from chitosan, chitosan salts and chitosan derivatives. In at least one embodiment, the composition comprises a hairstyling polymer selected from the group consisting of: polyquaternium-4, polyquaternium-11, polyquaternium-16, polyquaternium-68, mixtures thereof; or from the group consisting of: polyquaternium-4, polyquaternium-68, and mixtures thereof. In at least one embodiment, the composition comprises a hairstyling polymer selected from the group consisting of: polyquaternium-4, polyquaternium-11, polyquaternium-68, mixtures thereof; or from the group consisting of: polyquaternium-4, polyquaternium-68, and mixtures thereof.

In at least one embodiment, the composition comprises less than 0.5 wt.-% of a cationic hairstyling polymer by total weight of the composition.

In at least one embodiment, the composition comprises an amphoteric or zwitterionic hairstyling polymer. In at least one embodiment, the amphoteric or zwitterionic hairstyling polymer is selected from the group consisting of: copolymers formed from alkylacrylamide, alkylaminoalkyl methacrylate, and two or more monomers from acrylic acid and methacrylic acid as well as, if necessary, their esters, especially copolymers from octylacrylamide, acrylic acid, butylaminoethyl methacrylate, methyl methacrylate and hydroxypropyl methacrylate (octylacrylamide/acrylate/butylaminoethyl methacrylate copolymer, for example Amphomer® from Akzo Nobel); copolymers, that are formed from at least one of a first type of monomer that possesses quaternary amino groups and at least one of a second type of monomer that possesses acid groups; copolymers from fatty alcohol acrylates, alkylamine oxide methacrylate and at least one monomer selected from acrylic acid and methacrylic acid as well as, if necessary, acrylic acid esters and methacrylic acid esters, especially copolymers from lauryl acrylate, stearyl acrylate, ethylamine oxide methacrylate and at least one monomer selected from acrylic acid and methacrylic acid as well as, if necessary, their esters; copolymers from methacryloyl ethyl betaine and at least one monomer selected from methacrylic acid and methacrylic acid esters; copolymers from acrylic acid, methyl acrylate and methacrylamidopropyltrimethylammonium chloride (polyquaternium-47); copolymers from acrylamidopropyltrimethylammonium chloride and acrylates or copolymers from acrylamide, acrylamidopropyltrimethylammonium chloride, 2-amidopropylacrylamide sulfonate and dimethylaminopropylamine (polyquaternium-43); oligomers or polymers, producible from quaternary crotonoylbetaines or quaternary crotonoylbetaine esters. In at least one embodiment, the composition comprises an amphoteric or zwitterionic latex hairstyling polymer. In at least one embodiment, the hairstyling polymer is selected from the group consisting of: polyquaternium-47, octylacrylamide/acrylate/butylaminoethyl methacrylate copolymers, and mixtures thereof.

The hairstyling composition may comprise an anionic hairstyling polymer. In at least one embodiment, the anionic hairstyling polymer is selected from the group consisting of: acrylates copolymers of two or more monomers of (meth) acrylic acid or one of their simple esters (e.g. Balance® CR from Akzo Nobel); acrylates/hydroxyesters acrylates copolymers including those being copolymers of butyl acrylate, methyl methacrylate, methacrylic acid, ethyl acrylate and hydroxyethyl methacrylate (e.g. Acudyne™ 1000 from Dow Personal Care); terpolymers of acrylic acid, ethyl acrylate, and N-tert-butylacrylamide; crosslinked or uncrosslinked vinyl acetate/crotonic acid copolymers; terpolymers of tert-butylacrylate, ethyl acrylate and methacrylic acid; sodium polystyrenesulfonate; copolymers of vinyl acetate, crotonic acid and vinyl propionate; copolymers of vinyl acetate, crotonic acid and vinyl neodecanoate;

aminomethylpropanol/acrylate copolymers; copolymers of vinylpyrrolidone and at least one further monomer selected from among acrylic acid, methacrylic acid, acrylic acid esters and methacrylic acid esters; copolymers of methyl vinyl ether and maleic acid monoalkyl esters; aminomethylpropanol salts of copolymers of allyl methacrylate and at least one further monomer selected from among acrylic acid, methacrylic acid, acrylic acid esters and methacrylic acid esters; crosslinked copolymers of ethyl acrylate and methacrylic acid; copolymers of vinyl acetate, mono-n-butyl maleate and isobornyl acrylate; copolymers of two or more monomers selected from among acrylic acid, methacrylic acid, acrylic acid esters and methacrylic acid esters, copolymers of octylacrylamide and at least one monomer selected from among acrylic acid, methacrylic acid, acrylic acid esters and methacrylic acid esters; polyesters of diglycol, cyclohexanedimethanol, isophthalic acid and sulfoisophthalic acid; polyurethanes; and copolymers of polyurethane and acrylates. e.g. polyurethane-14/AMP-acrylates polymer blend (e.g. DynamX® from Akzo Nobel). Suitable polyester polymers include polyester-5 polymers, for example AQ® 48 Ultra Polymer, (diglycol/CHDM/isophthalates/SIP copolymer [a copolymer of diethylene glycol, 1,4-cyclohexanedimethanol and the simple esters of isophthalic acid and sulfoisophthalic acid]), AQ® 55 S, and AQ® 38 S, all from Eastman Chemical Company. Also suitable is a polyvinylmethacrylic acid/maleic acid copolymer (Omnirez® 2000 from ISP). Anionic latex hairstyling polymers are also suitable. In at least one embodiment, the anionic hairstyling polymer is selected from the group consisting of: polyurethane-1 (e.g. Luviset® P.U.R. from BASF), polyurethane-14/AMP-acrylates copolymer blend (e.g. DynamX® from Akzo Nobel), acrylates copolymers of two or more monomers of (meth)acrylic acid or one of their simple esters (e.g. Balance® CR from Akzo Nobel), and mixtures thereof. In at least one embodiment, the anionic hairstyling polymer is polyurethane-1.

The composition may comprise a non-ionic hairstyling polymer. In at least one embodiment, the composition comprises a non-ionic hairstyling polymer, wherein are non-ionic hairstyling polymer is a homo- or copolymer that is formed from at least one of the following monomers: vinylpyrrolidone, vinylcaprolactam, vinyl esters such as, for example, vinyl acetate, vinyl alcohol, acrylamide, methacrylamide, alkyl- and dialkylacrylamide, alkyl- and dialkylmethacrylamide, alkyl acrylate, alkyl methacrylate, propylene glycol or ethylene glycol, where the alkyl groups in these monomers may be $C_1$- to $C_7$-alkyl groups or $C_1$- to $C_3$-alkyl groups. In at least one embodiment, the composition comprises a homopolymer selected from the group consisting of: vinylcaprolactam, vinylpyrrolidone, N-vinylformamide and mixtures thereof. In at least one embodiment, the non-ionic hairstyling polymer is selected from the group consisting of: copolymers of vinylpyrrolidone and vinyl acetate, terpolymers of vinylpyrrolidone, vinyl acetate and vinyl propionate, polyacrylamides; polyvinyl alcohols as well as polyethylene glycol/polypropylene glycol copolymers; and mixtures thereof. In at least one embodiment, the non-ionic hairstyling polymer is selected from the group consisting of: polyvinylpyrrolidone/dimethylaminopropylaminoacrylates copolymer (Aquaflex® SF 40 from ISP); isobutylene ethylmaleinimide/hydroxy ethylmaleinimide copolymer (Aquaflex® FX 64 from ISP); vinylcaprolactam/polyvinylpyrrolidone/dimethylaminoethyl methacrylate copolymer (Advantage® from ISP); and mixtures thereof. Non-ionic latex hairstyling polymers are also suitable. In at least one embodiment, the non-ionic hairstyling polymer is selected from the group consisting of: polyvinylpyrrolidone (K90, 85, 80, 60, 30), polyvinylpyrrolidone/vinyl acetate copolymers (PVPNA 64), terpolymers of vinylpyrrolidone, methacrylamide and vinylimidazole (e.g. Luviset® Clear from BASF), and mixtures thereof. In at least one embodiment, the non-ionic hairstyling polymer is selected from the group consisting of: PVP K 60, 30, and PVPNA 37/64. In at least one embodiment, the non-ionic hairstyling polymer is selected from the group consisting of: PVP K60 and PVPNA 37/64.

In at least one embodiment, the composition comprises an anionic latex hairstyling polymer. In at least one embodiment, the anionic latex hairstyling polymer is a urethane-based polymer, for example polyurethane-34 (Baycusan® from Bayer). Polyurethane-34 is described in EP2105127A1. In at least one embodiment, the hairstyling polymer is the latex hairstyling polymer polyurethane-34.

In at least one embodiment, the anionic hairstyling polymer and/or cationic hairstyling polymer is present in neutralized or partially neutralized form. In at least one embodiment, the composition comprises a neutralising agent, and wherein the neutralising agent is selected from the group consisting of: potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia ($NH_3$), triethanolamine, trimethylamine (Tris Amino Ultra), aminomethylpropandiol (AMPD) and mixtures thereof. In at least one embodiment, the neutralising agent is 2-aminomethyl propanol.

Auxiliaries

In at least one embodiment, the composition comprises additives common in cosmetology, pharmacy, and dermatology, which are hereinafter called auxiliaries. In at least one embodiment, the auxiliary is selected from the group consisting of oily substances, emulsifiers, coemulsifiers, cationic polymers, film formers, superfatting agents, stabilizers, active biogenic substances, glycerol, preservatives, pearlizing agents, dyes and fragrances, solvents, opacifiers, functional acids, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and/or carriers/solvents.

In at least one embodiment, the composition comprises water soluble vitamins and their derivatives, water soluble amino acids and their salts and/or derivatives, viscosity modifiers, dyes, nonvolatile solvents or diluents (water soluble and insoluble), pearlescent aids, thickeners, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine, minoxidil, and combinations thereof. In at least one embodiment, the composition comprises from 0 wt.-% to 5 wt.-% vitamins and amino acids, by total weight of the composition. The composition may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The composition may comprise from 0 wt.-% to 5 wt.-% pigment materials. The composition may comprise from 0 wt.-% to 5 wt.-% antimicrobial agents.

In at least one embodiment, the composition comprises an oily substance, which is any fatty substance which is liquid at room temperature (25° C.). In at least one embodiment, the composition comprises oily substance selected from the group consisting of silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, argan oil, abyssinian oil, and coconut oil; synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$-$C_{13}$) fatty acids with linear ($C_6$-$C_{20}$) fatty alcohols; esters of branched ($C_6$-$C_{13}$) carboxylic acids with linear ($C_6$-$C_{20}$) fatty alcohols, esters of linear ($C_6$-$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$-$C_{10}$) fatty acids; esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

In at least one embodiment, the composition comprises a non-ionic coemulsifier. In at least one embodiment, the non-ionic coemulsifier is selected from adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; ($C_{12}$-$C_{18}$) fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance. Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

In at least one embodiment, the composition comprises a cationic polymer. Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37 & mineral oil & PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

In at least one embodiment, the composition comprises a superfatting agent. As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

In at least one embodiment, the composition comprises a stabiliser. As stabiliser it is possible to use metal salts of fatty acids, such as magnesium, aluminum and/or zinc stearate, for example.

In at least one embodiment, the composition comprises a care additive. The compositions can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, panthenol and similar substances as a care additive.

In at least one embodiment, the composition comprises a preservative or preservative system. Examples of suitable preservatives include benzyl alcohol, piroctone olamine, phenoxyethanol, parabens, pentanediol, benzoic acid/sodium benzoate, sorbic acid/potassium sorbate, and other organic acids used to provide antimicrobial protection. Preservation boosting ingredients include anisic acid, lactic acid, sorbitan caprylate, ethylhexylglycerin, caprylyl glycol, octanediol, and similar substances. In at least one embodiment, the composition comprises 0.01 to 5 wt.-%, particularly preferably from 0.05 wt.-% to 1 wt.-% of at least one preservative. Suitable preservatives are the substances listed in the International Cosmetic Ingredient Dictionary and Handbook, 9th Edition with the function "preservatives". In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition comprises a preservative selected from the group consisting of cetyltrimethyl ammoniumchloride, cetylpyridinium chloride, benzethonium chloride, diisobutylethoxyethyldimethyl benzylammoniumchloride, sodium N-lauryl sarcosinate, sodium-N-palmethylsarcosinate, Lauroylsarcosine, N-myristoylglycine, potassium-N-laurylsarcosine, trimethylammoniumchloride, sodium aluminium chlorohydroxylactate, triethylcitrate, tricetylmethylammoniumchloride, 2,4,4'-trichloro-2'-hydroxydiphenylether (Triclosan), phenoxyethanol, 1,5-pentandiol, 1,6-hexandiol, 3,4,4'-trichlorocarbanilide (Triclocarban), diaminoalkylamide, L-lysine hexadecylamide, heavy metal citrate salts, salicylate, piroctose, zinc salts, pyrithione and its heavy metal salts, zinc pyrithione, zinc phenol sulfate, farnesol, ketoconazol, oxiconazol, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, selenium disulfide, Octopirox®, methylchloroisothiazolinone, methylisothiazolinone, methyldibromo glutaronitrile, AgCl, chloroxylenol, sodium salts of diethylhexylsulfosuccinate, sodiumbenzoate, phenoxyethanol, benzylalkohol, phenoxyisopropanol, paraben, such as butyl-, ethyl-, methyl- and propylparaben, and their salts, pentandiol, 1,2-octanediol, ethylhexylglycerin, benzylalcohol, sorbic acid, benzoic acid, lactic acid, imidazolidinyl urea, diazolidinyl urea, dimethylol dimethyl hydantoin (DMDMH), sodium salts of hydroxymethyl glycinate, hydroxyethylglycine of sorbic acid and combinations thereof. In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition is substantially free of parabens.

In at least one embodiment, the composition comprises an anti-fungal substance. In at least one embodiment, the anti-fungal substance is selected from the group consisting of ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, zinc pyrithione, octopirox, and combinations thereof. In at least one embodiment, the composition comprises a total amount of anti-fungal substance in the composition of from 0.1 wt.-% to 1 wt.-%. In at least one embodiment, the composition comprises a pyridinethione anti-dandruff particulates, for example 1-hydroxy-2-pyridinethione salts, are highly preferred particulate anti-dandruff agents. The concentration of pyridinethione antidandruff particulate may ranges from 0.1% to 4%, by weight of the composition, preferably from 0.1% to 3%, more preferably from 0.3% to 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or regrowth of hair may be stimulated or regulated, or both, or that hair loss may be reduced or inhibited, or that hair may appear thicker or fuller.

Functional acids are acidic substances used to impart a clinical functionality to the skin or hair upon application.

Suitable functional acids include alpha hydroxy acids, beta-hydroxy acids, lactic acid, retinoic acid, and similar substances.

In at least one embodiment, the composition comprises an astringent. In at least one embodiment, the astringent is selected from the group consisting of magnesium oxide, aluminium oxide, titanium dioxide, zirconium dioxide, zinc oxide, oxide hydrates, aluminium oxide hydrate (boehmite) and hydroxide, chlorohydrates of calcium, magnesium, aluminium, titanium, zirconium or zinc. In at least one embodiment, the composition comprises from 0.001 wt.-% to 10 wt.-%, or from 0.01 wt.-% to 9 wt.-%, or from 0.05 wt.-% to 8 wt.-%, or from 0.1 wt.-% to 5 wt.-% astringent.

In at least one embodiment, the composition comprises a deodorising agent. In at least one embodiment, the deodorising agent is selected from the group consisting of allantoin, bisabolol, and combinations thereof. In at least one embodiment, the composition comprises from 0.001 wt.-% to 10 wt.-%, or from 0.01 wt.-% to 9 wt.-%, or from 0.05 wt.-% to 8 wt.-%, or from 0.1 wt.-% to 5 wt.-% deodorising agent.

In at least one embodiment, the composition comprises a sun protection agent and/or UV filter. Suitable sun protection agents and UV filters are disclosed in WO2013017262A1 (published on 7 Feb. 2013), from page 32, line 11 to the end of page 33. In at least one embodiment, the sun protection agent and/or UV filter is selected from the group consisting of 4-amino benzoic acid, 3-(4'-trimethylammonium)-benzylide-boran-2-one-methylsulfate, camphor benzalkonium methosulfate, 3,3,5-trimethyl-cyclohexylsalicylate, 2-hydroxy-4-methoxybenzophenone, 2-phenylbenzimidazole-5-sulfonic acid and potassium-, sodium-und triethanolamine salts thereof, 3,3'-(1,4-phenylene dimethine)-bis-(7,7-dimethyl-2-oxobicyclo[2.2.1]-heptane-1-methane sulfonic acid) and its salts, 1-(4-tert.-butylphenyl)-3-(4-methoxyphenyl) propan-1,3-dion, 3-(4'-sulfo)-benzylidene-bornane-2-one its salts, 2-cyan-3,3-diphenyl-acrylic acid-(2-ethylhexylester), polymers of N-[2(and 4)-(2-oxoborn-3-ylidenmethyl)benzyl]-acrylamide, 4-methoxy-cinnamic acid-2-ethyl-hexylester, ethoxylated ethyl-4-amino-benzoate, 4-methoxy-cinnamic acid-isoamylester, 2,4,6-tris-[p-2-ethylhexyloxycarbonyl)anilino]-1,3,5-triazine, 2-(2H-benzotriazole-2-yl)-4-methyl-6-(2-methyl-3-(1,3,3,3-tetramethyl-1-(trimethylsilyloxy)-disiloxanyl)-propyl) phenol, 4,4'-[(6-[4-((1,1-dimethylethyl)-amino-carbonyl) phenylamino]-1,3,5-triazin-2,4-yl)diimino]bis-(benzoic acid-2-ethylhexylester), 3-benzophenone, 4-benzophenone (acic), 3(4'-methylbenzyliden)-D,L-camphor, 3-benzylidene-camphor, salicylic acid-2-ethylhexylester, 4-dimethyl aminobenzic acid-2-ethylhexylester, hydroxy-4-methoxy-benzophenone-5 sulfonic acid and the sodium salt thereof, 4-isopropyl benzylsalicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium, and triethanolamine salts, octylmethoxy cinnamic acid, isopentyl-4-methoxy cinnamic acid, isoamyl-p-methoxy cinnamic acid, 2,4,6-trianilino-(p-carbo-2'-ethylhexyl-1'-oxy)-1,3,5-triazine (octyl triazone) phenol, 2,2(2H-benzotriazol-2-yl)-4-methyl-6-(2-methyl-3-(1,3,3,3-tetra methyl-1-(trimethylsilyl)oxy)-disiloxanyl)propyl (drometrizole trisiloxane) benzic acid, 4,4-((6-(((1,1-dimethylethyl)amino)carbonyl)phenyl)amino)-1,3,5-triazine-2,4-diyl)diimino)bis,bis(2-ethylhexyl)ester) benzoic acid, 4,4-((6-(((1,1-dimethylethyl)amino)-carbonyl) phenyl)amino)-1,3,5-triazine-2,4-diyl)diimino)bis,bis(2-ethylhexyl)ester), 3-(4'-methylbenzylidene)-D,L-camphor (4-methylbenzylidene camphor), benzylidene-camphor-sulfonic acid, octocrylene, polyacrylamidomethyl-benzylidene-camphor, 2-ethylhexyl salicylate (octyl salicylate), 4-dimethyl-aminobenzoeacidethyl-2-hexylester (octyl dimethyl PABA), PEG-25 PABA, 2 hydroxy-4-methoxybenzophenone-5-sulfonic acid (5-benzophenone) and the sodium salt thereof, 2,2'-methylene-bis-6-(2H-benzotriazol-2-yl)-4-(tetramethyl-butyl)-1,1,3,3-phenol, the sodium salt of 2-2'-bis-(1,4-phenylene)1H-benzimidazole-4,6-disulfonic acid, (1,3,5)-triazine-2,4-bis((4-(2-ethyl-hexyloxy)-2-hydroxy)-phenyl)-6-(4-methoxyphenyl), 2-ethyl hexyl-2-cyano-3,3-diphenyl-2-propenoate, glyceryl octanoate, di-p-methoxy cinnamic acid, p-amino-benzoic acid and its ester, 4-tert-butyl-4'-methoxydibenzoylmethane, 4-(2-β-glucopyranoxy) propoxy-2-hydroxybenzophenone, octyl salicylate, methyl-2,5-diisopropyl cinnamic acid, cinoxate, dihydroxy-dimethoxybenzophenone, disodium salts of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzyliden-dioxoimidazolidinpropionate, methylene-bis-benztriazolyl tetramethylbutylphenol, phenyldibenzimidazoltetrasulfonate, bis-ethylhexyloxyphenol-methoxyphenol-triazine, tetrahydroxybenzophenone, terephthalylidendicamphor-sulfonic acid, 2,4,6-tris[4,2-ethylhexyloxycarbonyl)anilino]-1,3,5-triazine, methyl-bis (trimethylsiloxy)silyl-isopentyl trimethoxy cinnamic acid, amyl-p-dimethylaminobenzoate, amyl-p-dimethylamino benzoate, 2-ethylhexyl-p-dimethylaminobenzoate, isopropyl-p-methoxy cinnamic acid/diisopropyl cinnamic acid ester, 2-ethylhexyl-p-methoxy cinnamic acid, 2-hydroxy-4-methoxy benzophenone, 2-hydroxy-4-methoxybenzophenone-5-sulfonic acid and the trihydrate, 2-hydroxy-4-methoxybenzophenone-5-sulfonate sodium salt, phenyl-benzimidazole sulfonic acid, and combinations thereof. In at least one embodiment, the composition comprises from 0.001 wt.-% to 10 wt.-%, preferably from 0.05 wt.-% to 5 wt.-%, even more preferably from 0.1 wt.-% to 3 wt.-%, most preferably from 0.05 wt.-% to 1 wt.-% sun protection agent and/or UV filter. In at least one embodiment, the composition comprises a photoprotective substance in an amount of from 0.01 to 10 wt.-%, or from 0.1 to 5 wt.-%, particularly preferably from 0.2 to 2 wt.-%. The photoprotective substances include, in particular, all of the photoprotective substances specified in EP 1 084 696, which is incorporated herein by reference. In a preferred embodiment, the photoprotective substance is selected from the group consisting of 2-ethylhexyl 4-methoxycinnamate, methyl methoxycinnamate, 2-hydroxy-4-methoxybenzophenone-5-sulfonic acid, polyethoxylated p-aminobenzoates, and combinations thereof.

In at least one embodiment, the composition comprises an anti-oxidant. In at least one embodiment, the anti-oxidant is selected from the group consisting of amino acids, peptides, sugars, imidazoles, carotinoids, carotenes, chlorogenic acid, lipoic acid, thiols, thiol glycosyl esters, thiol N-acetyl esters, thiol methyl esters, thiol ethyl esters, thiol propyl esters, thiol amyl esters, thiol butyl esters, thiol lauryl esters, thiol palmitoyl esters, thiol oleyl esters, thiol linoleyl esters, thiol cholesteryl esters, thiol glyceryl esters, dilaurylthiodipropionate, distearylthiodipropionate, thiodipropionic acid, metal chelators, hydroxy acids, fatty acids, folic acids, vitamin C, tocopherol, vitamin A, stilbenes, derivatives and combinations thereof. In at least one embodiment, the anti-oxidant is selected from the group consisting of glycine, histidine, tyrosine, tryptophan, urocaninic acid, D,L-carnosine, D-carnosine, L-carnosine, beta-carotene, alpha-carotene, lycopene, dihydrolipoic acid, aurothioglucose, propylthiouracil, thioredoxine, glutathione, cysteine, cystine, cystamine, buthioninsulfoximine, homocysteinsulfoximine, buthioninsulfone, penta-, hexa-, heptathioninsulfoximine, hydroxyfatty acids, palmitic acid, phytinic acid, lactoferrin, citric acid, lactic acid, malic acid, humic acid, bile acid, bilirubin, biliverdin, EDTA, EGTA, linoleic acid, linolenic acid, oleic acid, butylhydroxyanisol, trihydroxybutyrophenone, ubichinon, ubichinol, ascorbylpalmitate, Mg-ascorbylphosphate, ascorbylacetate, vitamin E acetate, vitamin A palmitate, carnosine, mannose, ZnO, ZnSO$_4$, selenium methionine, stilbenes, superoxide dismutase, and combinations thereof. In at least one embodiment, the antioxidant is selected from the group consisting of vitamin A, vitamin A derivatives, vitamin E, vitamin E derivatives, and combinations thereof. In at least one embodiment, the composition comprises from 0.001 wt.-% to 10 wt.-%, preferably from 0.05 wt.-% to 5 wt.-%, even more preferably from 0.1 wt.-% to 3 wt.-%, most preferably from 0.05 wt.-% to 1 wt.-% antioxidant.

In at least one embodiment, the composition comprises a dye or pigment. In at least one embodiment, the composition comprises at least one pigment. Suitable dyes and pigments are disclosed in WO2013017262A1 in the table spanning pages 36 to 43. These may be colored pigments which impart color effects to the product mass or to hair, or they may be luster effect pigments which impart luster effects to the product mass or to the hair. The color or luster effects on the hair are preferably temporary, i.e. they last until the next hair wash and can be removed again by washing the hair with customary shampoos. In at least one embodiment, the composition comprises a total amount of from 0.01 wt.-% to 25 wt.-%, preferably from 5 wt.-% to 15 wt.-% pigment. In at least one embodiment, the particle size of the pigment is from 1 micron to 200 micron, preferably from 3 micron to 150 micron, more preferably 10 micron to 100 micron. The pigments are colorants which are virtually insoluble in the application medium, and may be inorganic or organic. Inorganic-organic mixed pigments are also possible. Preference is given to inorganic pigments. The advantage of inorganic pigments is their excellent resistance to light, weather and temperature. The inorganic pigments may be of natural origin. In at least one embodiment, the inorganic pigment is selected from the group consisting of chalk, ochre, umber, green earth, burnt sienna, graphite, and combinations thereof. The pigments may be white pigments, such as, for example, titanium dioxide or zinc oxide, black pigments, such as, for example, iron oxide black, colored pigments, such as, for example, ultramarine or iron oxide red, lustre pigments, metal effect pigments, pearlescent pigments, and fluorescent or phosphorescent pigments, where preferably at least one pigment is a colored, nonwhite pigment. In at least one embodiment, the pigment is selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments), and combinations thereof. In at least one embodiment, the pigment is selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), and combinations thereof. In at least one embodiment, the pigment is selected from the group consisting of pearlescent and colored pigments based on mica which are coated with a metal oxide or a metal oxychloride, such as titanium dioxide or bismuth oxychloride, and optionally further color-imparting substances, such as iron oxides, Prussian blue, ultramarine, carmine etc. and where the color can be determined by varying the layer thickness. Such pigments are sold, for example, under the trade names Rona®, Colorona®, Dichrona® and Timiron® by Merck, Germany. In at least one embodiment, the pigment is selected from the group consisting of organic pigments such as sepia, gamboge, bone charcoal, Cassel brown, indigo, chlorophyll and other plant pigments. In at least one embodiment, the pigment is selected from the group consisting of synthetic organic pigments such as azo pigments, anthraquinoids, indigoids, dioxazine, quinacridone, phthalocyanine, isoindolinone, perylene and perinone, metal complex, alkali blue and diketopyrrolopyrrole pigments.

In at least one embodiment, the composition comprises from 0.01 wt.-% to 10 wt.-%, preferably from 0.05 wt.-% to 5 wt.-%, of at least one particulate substance. Suitable substances are, for example, substances which are solid at room temperature (25° C.) and are in the form of particles. In at least one embodiment, the particulate substance is selected from the group consisting of silica, silicates, aluminates, clay earths, mica, insoluble salts, in particular insoluble inorganic metal salts, metal oxides, e.g. titanium dioxide, minerals and insoluble polymer particles are suitable. The particles are present in the composition in undissolved, preferably stably dispersed form, and, following application to the keratin substrate and evaporation of the solvent, can deposit on the substrate in solid form. A stable dispersion can be achieved by providing the composition with a yield point which is large enough to prevent the solid particles from sinking. An adequate yield point can be established using suitable gel formers in a suitable amount. In at least one embodiment, the particulate substance is selected from the group consisting of silica (silica gel, silicon dioxide) and metal salts, in particular inorganic metal salts, where silica is particularly preferred. Metal salts are, for example, alkali metal or alkaline earth metal halides, such as sodium chloride or potassium chloride; alkali metal or alkaline earth metal sulfates, such as sodium sulfate or magnesium sulfate.

In at least one embodiment, the composition comprises a direct dye. Preferred among the direct dyes are the following compounds, alone or in combination with one another: Hydroxyethyl-2-nitro-p-toluidine, 2-hydroxyethylpicramic acid, 4-nitrophenylaminourea, tri(4-amino-3-methylphenyl) carbenium chloride (Basic Violet 2), 1,4-di-amino-9,10-anthracenedione (Disperse Violet 1), 1-(2-hydroxy-ethyl) amino-2-nitro-4-[di(2-hydroxyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio) naphthalene chloride (C.I. 12245; Basic Red No. 76), 3-methyl-1-phenyl-4-{[3-(trimethylammonio)phenyl] azo}pyrazol-5-one chloride (C.I. 12719; Basic Yellow No. 57) and 2,6-diamino-3-[(pyridin-3-yl)azo]pyridine as well as the salts thereof. Particularly preferred among the aforesaid direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxy-ethyl)amino-2-nitro-4-[di(2-hydro-xyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)-amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl) azo]-7-(trimethylammonio)-2-naphthol chloride (C.I. 12250; Basic Brown No. 16), 1-[(4-amino-2-nitrophenyl) azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio) phenyl]azo}pyrazol-5-one chloride (C.I. 12719; Basic Yellow No. 57) and 2,6-diamino-3-[(pyridin-3-yl)azo]pyridine as well as the salts thereof.

In at least one embodiment, the total quantity of direct dyes in the composition amounts to 0.01 to 15 wt.-%, preferably 0.1 to 10 wt.-%, most preferred 0.5 to 8 wt.-%.

Third Aspect

A third aspect relates to the use of the hybrid polymer according to the first aspect as a thickening agent, structurant, and/or rheology modifier.

In at least one embodiment, the hybrid polymer is used in a cosmetic composition.

Fourth Aspect

A fourth aspect relates to a kit comprising the composition according to the second aspect and a formulation selected from the group consisting of hair conditioning formulations, hair styling formulations, intensive conditioning formulations, skin moisturizing formulations, and combinations thereof.

Fifth Aspect

A fifth aspect relates to a container comprising a package comprising a receptacle comprising the composition according to the second aspect and wherein the package comprises a closure for containing the composition in the receptacle.

Sixth Aspect

A sixth aspect relates to method for cleansing hair and/or skin comprising applying the composition according to the second aspect onto hair and/or skin.

Seventh Aspect

A seventh aspect relates to the use of the composition according to the second aspect as a cosmetic agent.

Eighth Aspect

An eighth aspect relates to a polymerisation process for synthesising a water-soluble and/or water-swellable hybrid polymer comprising:
(i) from 5 wt.-% to 95 wt.-% water-soluble and/or water-swellable polysaccharide polymer; and
(ii) from 5 wt.-% to 95 wt.-% synthetic polymer as defined in the first aspect;
characterised in that the components (i) and (ii) are polymerised by radical precipitation polymerisation in a solvent. Preferably the polymerisation is grafting radical precipitation polymerisation.

In at least one embodiment, the monomer(s) resulting in units in the synthetic polymer are/is neutralised with a base prior to the polymerisation, and/or the hybrid polymer after polymerisation is neutralised with a base.

In at least one embodiment, the monomers resulting in units (a) and/or (b) are/is neutralised with a base prior to the polymerisation, and/or the hybrid polymer after polymerisation is neutralised with a base.

In at least one embodiment, wherein the base is selected from bases comprising an cation selected the group consisting of $NH_4^+$, $Li^+$, $Na^+$, $K^+$, $Ca^{++}$, $Mg^{++}$, $Zn^{++}$, $Al^{+++}$, $Zr^{++++}$ and mixtures thereof; preferably wherein the base is selected from hydroxides, carbonates and hydrogen carbonates comprising an ion selected the group consisting of $NH_4^+$, $Li^+$, $Na^+$, $K^+$, $Ca^{++}$, $Mg^{++}$, $Zn^{++}$, $Al^{+++}$ and mixtures thereof. In at least one embodiment, the base is selected from the group consisting of gaseous ammonia, ammonium hydrogen carbonate, ammonium carbonate, ammonium hydroxide, sodium hydrogen carbonate, sodium carbonate, sodium hydroxide, potassium hydrogen carbonate, potassium carbonate, potassium hydroxide, lithium hydrogen carbonate, lithium carbonate, lithium hydroxide, calcium hydrogen carbonate, calcium carbonate, calcium hydroxide, preferably sodium hydrogen carbonate, sodium carbonate, sodium hydroxide, potassium hydrogen carbonate, potassium carbonate, potassium hydroxide, even more preferably sodium hydrogen carbonate, sodium carbonate, sodium hydroxide, most preferably sodium hydrogen carbonate and sodium carbonate.

In at least one embodiment, the solvent is an organic or inorganic solvent having a highly inert behaviour in free-radical polymerisation reactions and which advantageously allow the formation of medium or high molecular weights, or mixtures of such solvents. The choice of chemistry and level of solvent is important in view of ensuring the dispersion and dissolving of the units making up the hybrid polymer in the reaction mixture. Furthermore, the hybrid polymer as it is synthesised should not result in the build-up of clumps and/or adhesions in the reaction mixture or on the equipment. It is advantageous that no significant agglomerates and adhesions build up within the stirring equipment because of the risk of damage and extension cleaning requirements. In at least one embodiment, the solvent has a boiling point of from 20° C. to 110° C., or from 40° C. to 95° C., or from 50° C. to 90° C. In at least one embodiment, the solvent is a polar solvent. In at least one embodiment, the solvent is selected from the group consisting of water, lower alcohols, and mixtures of water and lower alcohols. In at least one embodiment, the solvent is selected from the group consisting of methanol, ethanol, propanol, acetone, iso-, sec- and t-butanol, hydrocarbons having 1 to 30 carbon atoms, and mixtures and emulsions thereof. In at least one embodiment, the solvent is a mixture of water and a solvent selected from the group consisting of methanol, ethanol, propanol, acetone, iso-, sec- and t-butanol, hydrocarbons having 1 to 30 carbon atoms. In at least one embodiment, the solvent is selected from the group consisting of methanol, ethanol, 1-propanol, 2-propanol, 2-methyl-2-propanol, 1-butanol, 2-butanol, dimethyl ketone, diethyl ketone, tetrahydropyran, tetrahydrofuran, 2-methyltetrahydrofuran, 1,3-dioxane, 1,4-dioxane, preferably ethanol, 1-propanol, 2-propanol, 2-methylpropan-2-ol, 1-butanol, 2-butanol, dimethyl ketone, tetrahydrofuran, 2-methyltetrahydrofuran, 1,3-dioxane, even more preferably 2-propanol, 2-methylpropan-2-ol, dimethyl ketone, tetrahydrofuran, 2-methyltetrahydrofuran, 1,3-dioxane, most preferably 2-methylpropan-2-ol and dimethyl ketone. In at least one embodiment, the solvent is a mixture of water and a solvent is selected from the group consisting of methanol, ethanol, 1-propanol, 2-propanol, 2-methyl-2-propanol, 1-butanol, 2-butanol, dimethylketone, diethylketone, tetrahydropyran, tetrahydrofuran, 2-methyltetrahydrofuran, 1,3-dioxane, 1,4-dioxane, preferably ethanol, 1-propanol, 2-propanol, 2-methylpropan-2-ol, 1-butanol, 2-butanol, dimethylketone, tetrahydrofuran, 2-methyltetrahydrofuran, 1,3-dioxane, even more preferably 2-propanol, 2-methylpropan-2-ol, dimethylketone, tetrahydrofuran, 2-methyltetrahydrofuran, 1,3-dioxane, most preferably 2-methylpropan-2-ol and dimethyl ketone. In at least one embodiment, the solvent mixture comprises from 0.1 wt.-% to 30 wt.-% water, or from 0.5 wt.-% to 25 wt.-% water, or from 1 wt.-% to 20 wt.-% water, preferably from 0,5 wt.-% to 15 wt.-% water. It is advantageous to ensure that the level of water in the solvent is 30 wt.-% or below in view of reduced likelihood of clumping during the polymerisation process. Such build-up of clumps can put the stirring mechanism under undesirable strain. In at least one embodiment, the solvent mixture comprises from 1 wt.-% to 99.5 wt.-% preferably from 5 wt.-% to 95 wt.-%, more preferably from 10 wt.-% to 90 wt.-% 2-methylpropan-2-ol. In at least one embodiment, the solvent mixture is 2-methylpropan-2-ol and dimethyl ketone. In at least one embodiment, the solvent mixture comprises from 0.5 to 10 wt.-% water, from 1 wt.-% to 98.5 wt.-% 2 methylpropan-2-ol and from 1 wt.-% to 98.5 wt.-% dimethyl ketone, preferably from 0.5 wt.-% to 7.5 wt.-% water, from 5 wt.-% to 94.5 wt.-% 2-methylpropan-2-ol and from 5 wt.-% to 94.5 wt.-% dimethyl ketone, most preferably from 1 wt.-% to 5 wt.-% water, from 7.5 wt.-% to 91.5 wt.-% 2-methylpropan-2-ol and from 7.5 wt.-% to 91.5 wt.-% dimethyl ketone.

In at least one embodiment, the polymerisation takes place in the temperature range of from 0° C. to 150° C., or from 10° C. to 100° C., or from 20° C. to 90° C., or from 30° C. to 80° C., or from 30° C. to 70° C., or from 40° C. to 60° C., or from 50° C. to 70° C.

In at least one embodiment, the polymerisation takes place at either atmospheric pressure or under elevated or reduced pressure.

In at least one embodiment, the polymerisation may also be performed under an inert gas atmosphere, preferably under nitrogen gas.

In at least one embodiment, the polymerisation is carried out in the presence of an initiator. The initiator is used for initiating the polymerisation. In at least one embodiment, the initiator is selected from high-energy electromagnetic rays, mechanical energy, a chemical initiator, or combinations thereof. In at least one embodiment, the initiator is a radical-producing initiator. In at least one embodiment, the initiator is selected from the group consisting of organic peroxides, persulfates, azo initiators, and mixtures thereof. In at least one embodiment, the initiator is an organic peroxide selected from the group consisting of benzoyl peroxide, tert-butyl hydroperoxide, di-tert-butyl hydroperoxide, triphenylmethyl hydroperoxide, methyl ethyl ketone peroxide, cumene hydroperoxide, dilauroyl peroxide (DLP), and mixtures thereof.

In at least one embodiment, the initiator is an azo initiator selected from the group consisting of azo-bis-isobutyronitrile, 2,2'-azobis(4-methoxy-2.4-dimethyl valeronitrile), 2,2'-azobis(2,4-dimethyl valeronitrile), dimethyl 2,2'-azobis (2-methylpropionate), 2,2'-azobis(2-methylbutyronitrile), 1,1'-azobis(cyclohexane-1-carbonitrile), 2,2'-azobis[n-(2-propenyl)-2-methyl-propionamide], and mixtures thereof. In at least one embodiment, the initiator is an azo initiator selected from the group consisting of azodiisobutyronitrile (AIBN) and azobisamideopropyl hydrochloride (ABAH).

In at least one embodiment, the initiator is a persulfate selected from the group consisting of potassium peroxidisulfate, potassium peroxidisulfate, ammonium peroxidisulfate, potassium peroxi mono sulfat, sodium peroximonosulfate, ammonium peroximonosulfate, and mixtures thereof. Organic persulfates are also useful.

In at least one embodiment, the initiator is selected from the group consisting of inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate) or redox systems comprising as reducing component an aliphatic or aromatic sulfonic acid (e.g., benzenesulfonic acid, toluenesulfonic acid, etc.).

In at least one embodiment, the initiator is a mixture of a redox initiator and an azo initiator. This has the advantage that a redox initiator system generates significant amount of —O* radicals on polysaccharide backbone and azo initiator will deliver enough active synthetic polymer chains. The combination of a redox initiator and an azo initiator will increase the amount of grafted synthetic polymer chains on polysaccharide backbone.

In at least one embodiment, the initiator is a mixture of ammonium peroxidisulfate and sodium sulfite, potassium peroxidisulfate and sodium sulfite, ammonium peroxidisulfate and ascorbic acid, sodium peroxidisulfate and ascorbic acid, ammonium peroxidisulfate and N,N,N',N'-tetramethylene diamine, potassium peroxidisulfate and N,N,N',N'-tetramethylene diamine, ammonium peroximonosulfate and N,N,N',N'-tetramethylene diamine, ammonium peroximonosulfate and ascorbic acid, ammonium peroximonosulfate and thiourea, ammonium peroximonosulfate and malonic acid, ammonium peroximonosulfate and glycolic acid, ammoniumperoxi-monosulfate and malic acid, 2-hydroxy-2-sulfonatoacetic acid and sodium sulfite, 2-hydroxy-2-sulfonatoacetic acid and ammonium peroximonosulfat, 2-hydroxy-2-sulfonatoacetic acid and N,N,N',N'-tetramethylendiamin, tert.-butylhydroperoxide and N,N,N',N'-tetramethylendiamin, 2-hydroxy-2-sulfonatoacetic acid and tert.-butylhydroperoxide.

In at least one embodiment, the polymerisation comprises the step of treating the water-soluble and/or water-swellable polysaccharide polymer with water prior to polymerisation. This water treatment step preferably results in a homogenous distribution of water molecules in the polysaccharide polymer.

In at least one embodiment, the polymerisation comprises the step of recovering the hybrid polymer after polymerisation. In at least one embodiment, the filtrate following filtration of the polymerisation product comprises 5 wt.-% or less of solid material.

EXAMPLES

The examples which follow are intended to illustrate the subject matter of the invention, though without restricting it thereto.

General Synthesis Example

The water-soluble and/or water-swellable hybrid polymer comprises (i) water-soluble and/or water-swellable polysaccharide polymer; and (ii) synthetic polymer. Components (i) and (ii) are polymerised by radical precipitation polymerisation in a solvent. Preferably the polymerisation is grafting radical precipitation polymerisation. Firstly, to the water-soluble and/or water-swellable polysaccharide polymer (component [i]) a defined amount of water is added, which is then combined with the monomers used for the synthetic polymer (component [ii]) that have been dispersed or dissolved in solvent. The solvent is preferably a solvent mixture of 2-methylpropan-2-ol and water or a mixture of 2-methylpropan-2-ol, dimethylketone and water where the level of water in the solvent mixture is below 30 wt.-% by total weight of the solvent mixture. The polymerisation reaction is started for example by a radical-releasing initiator combined with a redox-initiator.

The synthetic polymer is preferably thus polymerised at the same time as the hybrid polymer is synthesised. The polymerisation reaction is preferably carried out between 30° C. and 70° C. and over a timeframe of at least 30 minutes. The hybrid polymer is produced in the solvent mixture as a white, voluminous precipitate. The hybrid polymer is recovered from the solvent via evaporation or drying means (e.g. vacuum drying) and/or via pressurised filtration or distillation. Indeed, even a low level of solvent remaining in the final product is unacceptable.

In some cases, the monomer(s) resulting in the structural units for the synthetic polymer is/are neutralised prior to the start of synthesis. In this case, the acid groups of the monomers are replaced by a base. However, the neutralisation of the acid groups on the synthetic polymer can also occur after the radical precipitation polymerisation has occurred.

Example 1

In a 1-Liter Quickfit round bottom flask equipped with a reflux condenser, sub surface gas inlet tubing, inner temperature sensor and overhead agitator 373.6 g dry 2-methylpropan-2-ol and 6.4 g deionized water was dosed. 80 g ACDMT was charged. The ACDMT was neutralized to a pH of 7 to 8 by injection of gaseous ammonia above the surface. The temperature was kept below 40° C. Then 9 g of xanthan gum with a homogenous water content of 3 wt.-%, 0.85 g trimethylolpropane triacrylate (TMPTA) and 0.9 g N,N,N',N'-tetramethylene diamine was dissolved/dispersed in the reaction mixture. At agitation of 200 rpm nitrogen was inject subsurface for 1 h. During this time the temperature of the reaction mixture was raised and stabilized to 60° C. with help of a water bath. At 60° C. the pH was readjusted to a pH of 7 to 8. Then the reaction was initiated by a continuously dosing of a mixture containing 20 g 2-methylpropan-2-ol, 1 g tert.-butylhydroperoxide (70% in water) and 1.35 g dimethyl 2,2'-azobis(2-methylpropionate) (V601) over approximately 120 min. After the complete dosage was reached the reaction mixture was heated to a gentle reflux for two hours.

The hybrid polymer is produced in the solvent mixture as a white, voluminous precipitate. The hybrid polymer is recovered from the solvent via evaporation or drying means (e.g. vacuum drying) and/or via pressurised filtration or distillation. Indeed, even a low level of solvent remaining in the final product is unacceptable.

Example 2

In a 1-Liter Quickfit round bottom flask equipped with a reflux condenser, sub surface gas inlet tubing, inner temperature sensor and overhead agitator 190 g dry 2-methylpropan-2-ol, 190 g dimethylketone and 6 g deionized water was dosed. 50 g ACDMT was charged and ACDMT was neutralized to a pH of 7 to 8 by addition of 20.2 g sodium hydrogen carbonate. The temperature was kept below 40° C. Then 27.5 g of xanthan gum with a homogenous water content of 3 wt.-%, 0.7 g trimethylolpropantriacrylate (TMPTA) and 0.6 g N,N,N',N'-tetramethylene diamine was dissolved/dispersed in the reaction mixture. At agitation of 200 rpm nitrogen was inject subsurface for 1 h. During this time the temperature of the reaction mixture was raised and stabilized to 60° C. with help of a water bath. At 60° C. the pH was readjusted to a pH of 7 to 8. Then the reaction was initiated by a continuously dosing of a mixture containing 20 g 2-methylpropan-2-ol, 0.72 g tert.-butylhydroperoxide (70% in water) and 1.1 g dimethyl 2,2'-azobis(2-methylpropionate) (V601) over approximately 120 min. After the complete dosage was reached the reaction mixture was heated to a gentle reflux for two hours.

The hybrid polymer is produced in the solvent mixture as a white, voluminous precipitate. The hybrid polymer is recovered from the solvent via evaporation or drying means (e.g. vacuum drying) and/or via pressurised filtration or distillation. Indeed, even a low level of solvent remaining in the final product is unacceptable.

According to the general procedure and Examples 1 and 2, all other hybrid polymer examples in Table 1 are synthesised by correspondingly adjusting water content, monomer and initiator composition.

TABLE 1

| | solids | | | Polysaccharide | | Synthetic | | Polysaccharide | | Initiator | |
| | [wt.-% | Solvent** | Water | polymer | | Polymer | Mono-mer I | polymer | t-BHP | TMEDA | V601 |
| Example | polymer] | [g] | [g] | [Name/wt.-%] | | [wt.-%] | [ACDMT/mol-%] | [Name/wt.-%] | [mol-%] | [mol-%] | [mol-%] |
|---|---|---|---|---|---|---|---|---|---|---|---|
| 1 | 18.3 | A. 400 | 20 | Xanthan | 10.0 | 90 | 99.3 | TMPTA | 0.7 | 2.03 | 2.0 | 1.51 |
| 2 | 16.4 | B. 400 | 20 | Xanthan | 35.2 | 64.8 | 99.0 | TMPTA | 1.0 | 2.23 | 2.1 | 1.96 |
| 3 | 17.7 | A. 400 | 20 | Xanthan | 65.0 | 35 | 99.5 | TMPTA | 0.5 | 4.03 | 4.0 | 2.09 |
| 4 | 16.6 | A. 400 | 20 | Xanthan | 50.4 | 49.6 | 99.5 | GPTA | 0.5 | 3.07 | 3.1 | 1.49 |
| 5 | 16.8 | A. 400 | 20 | Xanthan | 25.0 | 75 | 99.7 | PEAS | 0.3 | 2.02 | 2.0 | 2.02 |
| 6 | 18.3 | B. 400 | 20 | Guar gum | 10.0 | 90 | 99.3 | TMPTA | 0.7 | 4.00 | 4.0 | 1.51 |
| 7 | 18.1 | A. 400 | 20 | Guar gum | 15.2 | 84.8 | 99.9 | TMPTMA | 0.1 | 3.00 | 3.0 | 1.50 |
| 8 | 18.3 | A. 400 | 20 | Guar gum | 15.0 | 85 | 99.5 | PEG600 DMA | 0.5 | 3.02 | 3.0 | 2.03 |
| 9 | 20.2 | A. 400 | 20 | Guar gum | 24.6 | 75.4 | 99.0 | GPTA | 1.0 | 4.25 | 4.2 | 2.02 |
| 10 | 20.0 | A. 400 | 20 | Guar gum | 74.9 | 75.1 | 99.7 | PEAS | 0.3 | 2.07 | 2.1 | 2.01 |
| 11 | 20.1 | A. 400 | 20 | Chitosan | 30.0 | 70 | 99.4 | TMPTA | 0.6 | 3.01 | 3.0 | 2.01 |
| 12 | 20.1 | A. 400 | 20 | Chitosan | 30.0 | 70 | 99.7 | GPTA | 0.3 | 3.02 | 3.0 | 2.01 |

TABLE 1-continued

| | solids | | | Polysaccharide | | Synthetic | | Polysaccharide | | Initiator | | |
|---|---|---|---|---|---|---|---|---|---|---|---|---|
| Example | [wt.-% polymer] | Solvent** [g] | Water [g] | polymer [Name/wt.-%] | | Polymer [wt.-%] | Mono-mer I [ACDMT/mol-%] | polymer [Name/wt.-%] | | t-BHP [mol-%] | TMEDA [mol-%] | V601 [mol-%] |
| 13 | 20.1 | A. 400 | 20 | Carrageenan | 40.0 | 60 | 99.6 | TMPTA | 0.4 | 3.50 | 3.5 | 2.02 |
| 14 | 20.2 | A. 400 | 20 | Carrageenan | 40.0 | 60 | 99.3 | GPTA | 0.7 | 3.49 | 3.5 | 2.01 |
| 15 | 20.0 | B. 400 | 20 | Alginic acid | 20.0 | 80 | 99.9 | TMPTA | 0.1 | 3.06 | 3.0 | 1.50 |
| 16 | 20.0 | A. 400 | 20 | Alginic acid | 19.9 | 80.1 | 99.8 | GPTA | 0.2 | 3.06 | 3.0 | 1.51 |
| 17 | 20.1 | A. 400 | 20 | Fenugreek gum | 25.1 | 74.9 | 99.7 | PEAS | 0.3 | 3.05 | 3.0 | 1.51 |
| 18 | 19.1 | A. 400 | 20 | Fenugreek gum | 25.1 | 74.9 | 99.6 | GPTA | 0.4 | 3.48 | 3.5 | 1.53 |
| 19 | 20.0 | A. 400 | 20 | Locust bean gum | 27.5 | 72.5 | 99.8 | PEAS | 0.2 | 3.51 | 3.5 | 2.00 |
| 20 | 19.0 | A. 400 | 20 | Tara gum | 22.5 | 77.5 | 99.5 | GPTA | 0.5 | 3.50 | 3.5 | 1.99 |
| 21 | 17.7 | B. 400 | 20 | Konjac gum | 30.2 | 69.8 | 99.9 | GPTA | 0.1 | 3.01 | 3.0 | 1.50 |
| 22 | 17.7 | A. 400 | 20 | Konjac gum | 30.2 | 69.8 | 99.8 | TMPTA | 0.2 | 3.01 | 3.0 | 2.99 |

KEY: ACDMT = acryloyldimethyltaurate, NVP = N-vinyl-2-pyrrolidone, NVF = N-vinylformamide, VIMA = N-vinyl-N-methylacetamide, AS = acrylic acid, V601 = dimethyl 2,2'-azobis(2-methylpropionate), TBHP = tert.butylhydroperoxide, TMEDA = N,N,N',N'- tetramethylethylene diamine, PEG 600 DMA = polyethylene glycol dimethacrylate, FF6 = Brüggolit ®FF6,
**Solvent A = 2-methylpropan-2-ol,
**Solvent B = 2-methylpropan-2-ol/dimethylketone (1:1 mixture).

Example Compositions

The following compositions comprise Hybrid H, which is the hybrid polymer according to the first aspect.

Example Composition 1: After Sun Cream Gel

| A | Mineral Oil | 3.00% |
|---|---|---|
| | Isopropyl Palmitate | 3.00% |
| | Cetearyl Isononanoate | 3.00% |
| | Jojoba Oil | 3.00% |
| | Walnut Oil | 3.00% |
| | Tocopheryl Acetate | 1.00% |
| B | Hybrid H | 1.20% |
| C | Water | ad 100% |
| | Glycerin | 3.00% |
| | Allantoin (Clariant) | 0.20% |
| | Nipaguard ® POM (Clariant) | 1.00% |
| | Phenoxyethanol, Methylparaben, Piroctone Olamine | |
| | Panthenol | 1.00% |
| D | Collagen nativ 1% | 3.00% |
| | Ethanol | 1.50% |

Procedure:
I Mix A, then add B.
II Mix C.
III Stir II into I.
IV Add D to III.
V Finally homogenize the emulsion.

Example Composition 2: Sun Milk SPF 15

| A | Ethylhexyl Stearate | 7.00% |
|---|---|---|
| | Decyl Oleate | 5.00% |
| | Plantasens ® Natural Emulsifier HE 20 (Clariant) | 3.00% |
| | Cetearyl Glucoside (and) Sorbitan Olivate | |
| | Dimethicone | 2.00% |
| | Octocrylene | 7.00% |
| | Butyl Methoxydibenzoylmethane | 2.50% |
| | Ethylhexyl Salicylate | 4.50% |
| B | Water | Ad 100% |
| | Glycerin | 3.00% |
| C | Hybrid H | 1.00% |
| D | Nipaguard ® POM (Clariant) | 1.00% |
| | Phenoxyethanol (and) Piroctone Olamine (and) Methylparaben | |
| E | Citric Acid | q.s. |

Procedure:
I Mix the components of A and melt at approx. 80° C.
II Mix the components of B and stir until homogenous, heat up to 80° C.
III Add C to I.
IV Add III to II and homogenize with a high shear mixer at 19.000 rpm for 2 min.
V Cool down to room temperature while stirring (200 rpm).
VI Add D to V and stir at 200 rpm until homogenous.
VII Finally adjust the pH with E to 6.5.

Example Composition 3: Liquid Soap

| A | Water | Ad 100% |
|---|---|---|
| | Glycerin | 3.00% |
| | 1,2-Propanediol | 2.00% |
| | Hybrid H | 3.00% |
| B | Genapol ® LRO liquid (Clariant) | 20.00% |
| | Sodium Laureth Sulfate | |
| | Genagen ® CAB 818 (Clariant) | 4.00% |
| | Cocamidopropyl Betaine | |
| | GlucoTain ® Clear (Clariant) | 2.00% |
| | Caprylol/Caproyl Methyl Glucamide | |
| C | Nipaguard ™ DMDMH (Clariant) | 0.40% |
| | DMDM Hydantoin | |
| | Fragrance | 0.20% |
| | Sodium Cloride | 0.50% |
| D | Citric Acid | 0.10% |

Procedure:
I Mix ingredients of phase A.
II Mix phase B and add to I.
III Add phase C in the given order.
IV Stir until homogeneous.
V Adjust pH to 5.5.

Example Composition 4: Effect Shower Gel

| A | Genapol ® LRO liquid (Clariant) | 30.00% |
|---|---|---|
| | Sodium Laureth Sulfate | |
| | Genagen ® CAB 818 (Clariant) | 6.00% |
| | Cocamidopropyl Betaine | |
| | Hostapon ® KCG (Clariant) | 5.00% |
| | Sodium Cocoyl Glutamate | |

| | | |
|---|---|---|
| B | Water | Ad 100% |
| C | Hybrid H | 1.40% |
| D | Nipaguard ® DMDMH (Clariant) DMDM Hydantoin | 0.50% |
| | Cirebelle 104 Blue Sythetic Wax | 1.00% |

Procedure:

I Mix the components of A and B until complete dissolved.

II Add C and stir until the solution is free of lumps.

III Add D to II.

IV Finally adjust the pH if necessary.

Example Composition 5: Facial Cleanser

| | | |
|---|---|---|
| A | Water | Ad 100% |
| | Hybrid H | 1.80% |
| B | Genapol ® LRO paste (Clariant) Sodium Laureth Sulfate | 4.50% |
| | Medialan ® LD (Clariant) Sodium Lauroyl Sarcosinate | 13.50% |
| | Genagen ® CAB 818 (Clariant) Cocamidopropyl Betaine | 3.00% |
| C | Citric Acid | q.s. |
| D | Benzoic Acid | 0.50% |

Procedure:

I Add Polymer to water and stir until homogeneous.

II Add the ingredients of phase B to I in the given order.

III Adjust pH to 4.0 with phase C.

IV Add D.

Example Composition 6: Mascara

| | | |
|---|---|---|
| A | Hydroxyethylcellulose | 0.50% |
| | Hybrid H | 0.50% |
| | 1,2-Propyleneglycol | 1.00% |
| | Magnesium Aluminium Silicate | 1.00% |
| | Triethanolamine 99% | 1.50% |
| | Water | Ad 100% |
| B | Stearic Acid | 3.00% |
| | SilCare ® Silicone 41M15 (Clariant) Caprylyl Methicone | 1.00% |
| | SilCare ® Silicone 31M50 (Clariant) Caprylyl Trimethicone | 2.00% |
| | Tego ® Care 450 Polyglyceryl-3 Methylglucose Distearate | 4.00% |
| | Polybutene. | 2.00% |
| | Beeswax | 2.50% |
| | Plantasens ® Olive Wax S51 (Clariant) Hydrogenated Olive Oil | 2.50% |
| | Microcrystalline Wax | 3.50% |
| C | Iron Oxides | 10.0% |
| D | Phenonip ™ ME (Clariant) Phenoxyethanol, Methylparaben, Ethylparaben | 1.00% |
| E | Baycusan ® C 1004 Polyurethane-35 | 2.00% |

Procedure:

I Mix ingredients of phase A. Then heat to 80° C. while stirring.

II Mix ingredients of phase B and heat to 80° C.

III Add C to B and homogenize.

IV Add A to III while homogenizing (4 min, 20000 rpm), stir vigorously until 35-40° C.

V Add D and stir until homogeneous.

VI Add E and stir until homogeneous then stir until room temperature.

Example Composition 7: BB Cream SPF 15

| | | |
|---|---|---|
| A | Water | Ad 100% |
| | Glycerin | 2.00% |
| | Hybrid H | 1.00% |
| B | Hostaphat ® KW 340 D (Clariant) Triceteareth-4 Phosphate | 3.00% |
| | Cetearyl Alcohol | 2.00% |
| | Octocrylene | 7.00% |
| | Butyl Methoxydibenzoylmethane | 2.50% |
| | Ethylhexyl Salicylate | 4.50% |
| | Plantasens ® Olive LD (Clariant) Hydrogenated Ethylhexyl Olivate (and) Hydrogenated Olive Oil Unsaponifiables | 2.00% |
| | 12-15 Alkyl Benzoate | 8.00% |
| | Plantasens ® Olive Squalane (Clariant) Squalane | 2.00% |
| | Plantasens ® Shea Butter (Clariant) Butyrospermum Parkii (Shea) Butter | 1.00% |
| | XIAMETER ® PMX-200 Silicone Fluid 200 CS Dimethicone | 2.00% |
| C | Chroma-Lite ® Black Mica (and) Bismuth Oxychloride (and) Iron Oxides | 0.05% |
| | Chroma-Lite ® Red Mica (and) Bismuth Oxychloride (and) Iron Oxides | 0.20% |
| | Chroma-Lite ® Yellow Mica (and) Bismuth Oxychloride (and) Iron Oxides | 0.60% |
| | Titanium Dioxide | 5.00% |
| | Butylene Glycol | 4.00% |
| D | Plantasens ® Natural Vitamin E (Clariant) Tocopherol | 1.00% |
| | Panthenol | 0.50% |
| | Gatuline ® Age Defense 2 | 1.00% |
| | Aqua (and) *Juglans Regia* (Walnut) Seed Extract | |
| | Sodium Hyaluronate | 0.40% |
| | Orgasol ® 4000 EXD NAT COS Caresse Nylon-6/12 | 1.00% |
| | Fragrance | 0.20% |
| | Nipaguard ® POB (Clariant) Phenoxyethanol (and) Piroctone Olamine (and) Benzoic Acid | 0.80% |
| E | Citric Acid | q.s. |

Procedure:

I Mix ingredients of phase A until dissolved. Then heat to 80° C.

II Mix ingredients of phase B and heat to 80° C.

III Premix phase C then add to B and homogenize gently by using Ultra-Turrax.

IV Pour III into I and homogenize gently by using Ultra-Turrax. Then stir until 35° C.

V Add phase D in the given order and stir until homogeneous.

VI Adjust the pH to 5.5 to 6.0 with phase E.

Example Composition 8: WW Foundation

| | | |
|---|---|---|
| A | Water | Ad 100% |
| | Hybrid H | 1.00% |
| | Magnesium Aluminium Silicate | 1.00% |
| B | Plantasens ® Natural Emulsifier HP10 (Clariant) Sucrose Polystearate, Cetearyl Alcohol, Olea Europaea (Olive) Oil Unsaponifiables | 4.50% |
| | SilCare ® Silicone 31M50 (Clariant) Caprylyl Trimethicone | 2.00% |

-continued

| | | |
|---|---|---|
| | XIAMETER ® PMX-200 Silicone Fluid 100 CS Dimethicone | 2.00% |
| | Caprylic/Capric Triglyceride | 5.00% |
| | Plantasens ® Olive Wax S51 (Clariant) Hydrogenated Vegetable Oil | 1.50% |
| C | Chroma-Lite ® Black Mica (and) Bismuth Oxychloride (and) Iron Oxides | 0.10% |
| | Chroma-Lite ® Red Mica (and) Bismuth Oxychloride (and) Iron Oxides | 0.40% |
| | Chroma-Lite ® Yellow Mica (and) Bismuth Oxychloride (and) Iron Oxides | 1.20% |
| | Titanium Dioxide | 7.00% |
| | Dicaprylyl Carbonate | 4.00% |
| | Butylene Glycol | 3.00% |
| D | Plantasens ® Natural Vitamin E (Clariant) Tocopherol | 1.00% |
| | Orgasol ® 4000 EXD NAT COS Caresse Nylon-6/12 | 1.00% |
| | Fragrance | 0.20% |
| | Nipaguard ® POB (Clariant) Phenoxyethanol (and) Piroctone Olamine (and) Benzoic Acid | 0.80% |
| E | Citric Acid | q.s. |

Procedure:

I Mix ingredients of phase A and homogenize gently by using Ultra-Turrax, then stir and heat to 70° C.

II Mix ingredients of phase B and heat to 70° C.

III Premix phase C then add to B and homogenize gently by using Ultra-Turrax.

IV Pour III into I and homogenize gently by using Ultra-Turrax. Then stir until 35° C.

V Add phase D and stir until homogeneous.

VI Adjust the pH to 5.5 to 6.0 with phase E.

Example Composition 9: Liquid Highlighter

| | | |
|---|---|---|
| A | Water | Ad 100% |
| | Bentonite | 1.00% |
| B | Hybrid H | 1.00% |
| C | Liquiwax ™ PolyIPL Stearyl/PPG-3 Myristyl Ether Dimer Dilinoleate | 2.00% |
| | Plantasens ® Olive Wax S51 (Clariant) Hydrogenated Olive Oil | 2.00% |
| | Stearic Acid | 1.20% |
| | Isostearic Acid | 0.90% |
| D | Water | 5.00% |
| | Sodium Hydroxide | 0.12% |
| E | Orgasol ® 4000 EXD NAT COS Caresse Nylon-6/12 | 1.50% |
| | Timiron ® Super Gold Mica, Titanium Dioxide | 2.50% |
| | Xirona ® Indian Summer Silica (and) Iron Oxides | 2.50% |
| F | Panthenol | 0.50% |
| | Cyclopentasiloxane | 7.50% |
| | Phenonip ™ ME (Clariant) Phenoxyethanol, Methylparaben, Ethylparaben | 1.00% |
| | Tocopheryl Acetate | 1.00% |

Procedure:

I Phase A: disperse Bentonite in water.

II Add B to I and mix until dissolved, then heat to 80° C.

III Melt C at 80° C.

IV Add III to II while homogenizing (2 min, 20000 rpm).

V Premix D, add to IV and stir until homogeneous.

VI Add E to V and stir until cool (35° C.).

V Add F and stir until room temperature.

Example Composition 10: Lipstain

| | | |
|---|---|---|
| A | Water | Ad 100% |
| | Glycerin | 30.00% |
| | Hybrid H | 3.00% |
| B | FD&C Red No. 40 CI16035 | 0.15% |
| C | Emulsogen ® HCO 040 (Clariant) PEG-40 Hydrogenated Castor Oil | 0.50% |
| | Phenonip ™ ME (Clariant) Phenoxyethanol, Methylparaben, Ethylparaben | 1.00% |
| | Flavour | 0.20% |

Procedure:

I Mix the components of A and stir until dissolved.

II Add B and stir until the solution is homogeneous.

III Add C and stir until dissolved.

IV Finally adjust the pH to 6.5 to 7.0, if necessary.

Example Composition 11: Eyeliner Gel

| | | |
|---|---|---|
| A | Water | Ad 100% |
| | Glycerin | 1.00% |
| | Hybrid H | 2.00% |
| B | Phenonip ™ ME (Clariant) Phenoxyethanol, Methylparaben, Ethylparaben | 1.00% |
| C | PVR | 1.50% |
| | Water | 10.00% |
| D | Timiron ® Super Gold Mica, CI77891, Titanium Dioxide | 12.00% |

Procedure:

I Mix the components of A and stir until dissolved.

II Add B and stir until the solution is homogeneous.

III Premix C separately, then add to II and stir until dissolved.

IV Add D while stirring.

V Finally adjust pH to 7.5.

Example Composition 12: After Shave Balm

| | | |
|---|---|---|
| A | Hostaphat ® KL 340 D (Clariant) Trilaureth-4 Phosphate | 2.00% |
| | Octopirox ® (Clariant) Piroctone Olamine | 0.05% |
| B | Plantasens ® *Abyssinian* Oil (Clariant) *Crambe Abyssinica* Seed Oil | 2.00% |
| | Isopropyl Isostearate | 3.00% |
| | Plantasens ® Inca Inchi Serum (Clariant) *Plukenetia Volubilis* Seed Oil (and) Phytosterols (and) *Olea Europaea* (Olive) Oil Unsaponifiables (and) Beeswax | 1.00% |
| C | Water | Ad 100% |
| | Polyglykol 400 (Clariant) PEG-8 | 3.00% |
| | Allantoin | 0.30% |
| D | Hybrid H | 1.50% |
| E | Dimethicone | 1.00% |
| F | Citric Acid | q.s. |
| G | Phenonip ™ ME (Clariant) Phenoxyethanol, Methylparaben, Ethylparaben | 1.00% |

Procedure:

I Mix and dissolve the components of A.

II Add B into I.

III Mix and dissolve the components of C.

IV Add D into II.

V Add III to IV and stir at about 200 rpm for one hour.

VI Add E to V and stir for 30 min.

VII Adjust the pH with F to 5.5.
VIII Add G to VI and stir.
IX Finally homogenize.

Example Composition 13: Sprayable Body Milk

| A | Hostaphat ® KL 340 D (Clariant) | 1.00% |
|---|---|---|
|   | Trilaureth-4 Phosphate |   |
|   | Mineral Oil | 8.00% |
|   | Isopropyl Palmitate | 3.00% |
|   | Cetearyl Alcohol | 0.50% |
|   | Caprylic/Capric Triglyceride | 2.00% |
|   | Glyceryl Stearate | 0.50% |
|   | SilCare ® Silicone 41M15 (Clariant) | 1.00% |
|   | Caprylyl Methicone |   |
| B | Hybrid H | 1.00% |
| C | Water | ad 100% |
|   | Glycerin | 5.00% |
| D | Ethanol | 5.00% |
|   | Tocopheryl Acetate | 1.00% |
| E | Nipaguard ® POM (Clariant) | 1.00% |
|   | Phenoxyethanol, Methylparaben, Piroctone Olamine |   |

Procedure:
I Melt A at 60° C., then add B.
II Heat C to 60° C.
III Stir II into I, and stir until cool.
IV Add the components of D one after another to III at 35° C.
V Add E and then finally homogenize the emulsion.

Example Composition 14: Body Lotion for Men

| A | Caprylic/Capric Triglyceride | 3.50% |
|---|---|---|
|   | Plantasens ® Olive LD (Clariant) | 3.00% |
|   | Hydrogenated Ethylhexyl Olivate (and) Hydrogenated Olive Oil Unsaponifiables |   |
|   | Myristyl Myristate | 2.50% |
|   | Cetearyl Alcohol | 2.00% |
|   | Octyldodecanol | 1.00% |
|   | Glyceryl Stearate Citrate | 1.50% |
| B | Hybrid H | 1.20% |
| C | Water | ad 100% |
|   | Glycerin | 5.00% |
| D | Ethanol | 3.00% |
|   | Tocopheryl Acetate | 1.00% |
|   | *Aloe Barbadensis* Leaf Juice | 1.00% |
|   | Nipaguard ® POM (Clariant) | 1.00% |
|   | Phenoxyethanol, Methylparaben, Piroctone Olamine |   |
|   | Fragrance | 0.20% |
| E | Sodium Hydroxide | q.s. |

Procedure:
I Melt the components of A at approx. 70° C.
II Mix the components of C and heat to approx. 70° C.
III Add B to I when completely melted.
IV Add C to III.
V At 35° C. add the components of D to IV.
VI Adjust the pH with E to 6.0 to 6.5.

Example Composition 15: Anti-Ageing Cream Gel

| A | Caprylic/Capric Triglyceride | 5.00% |
|---|---|---|
|   | Dicaprylyl Ether | 5.00% |
|   | Cetearyl Alcohol | 2.00% |
|   | Nipaguard ® POB (Clariant) | 0.80% |
|   | Phenoxyethanol (and) Piroctone Olamine (and) Benzoic Acid |   |
| B | Ubiquinone | 0.10% |
| C | Aristoflex ® HMB (Clariant) | 0.40% |
|   | Ammonium Acryoyldimethyltaurate/Beheneth-25 Methacrylate Crosspolymer |   |
|   | Hybrid H | 0.40% |
| D | Sodium Hyaluronate | 0.30% |
| E | Water | Ad 100% |
| F | Tocopheryl Acetate | 0.30% |
|   | Fragrance | 0.30% |

Procedure:
I Mix the components of A and melt at 60° C.
II Add B and solve while shaking lightly.
III Add C.
IV Solve D in E and add to III.
V Add F to IV at 35° C.

Example Composition 16: Light Day Cream

| A | Water | Ad 100% |
|---|---|---|
|   | Hybrid H | 0.75% |
|   | Glycerin | 3.00% |
| B | Plantasens ® Natural Emulsifier HE20 (Clariant) | 1.20% |
|   | Cetearyl Glucoside, Sorbitan Olivate |   |
|   | Aristoflex ® AVC (Clariant) | 0.10% |
|   | Ammonium Acryloyldimethyltaurate/VP Copolymer |   |
|   | Plantasens ® *Abyssinian* Oil (Clariant) | 3.00% |
|   | *Crambe Abyssinica* Seed Oil |   |
|   | Octyldodecanol | 5.00% |
|   | Isodecyl Neopentanoate | 3.00% |
| C | Plantasens ® Natural Vitamin E (Clariant) | 0.50% |
|   | Tocopherol |   |
|   | Nipaguard ® SCP (Clariant) | 1.00% |
|   | Phenoxyethanol (and) Sorbitan Caprylate |   |
|   | Fragrance | 0.30% |
| D | Citric Acid | q.s. |

Procedure:
I Mix ingredients of phase A, stir for 5 minutes and homogenize during 1 min using Ultra-Turrax.
II Add B and heat to 75° C.
III At Temperature, homogenize gently during 1 min using Ultra-Turrax.
IV Cool down under stirring.
V Below 40° C. add C and stir.
VI Adjust pH with D to 5.5.

Example Composition 17: Caring Night Cream

| A | Water | Ad 100% |
|---|---|---|
|   | Glycerin | 2.00% |
|   | Hybrid H | 1.00% |
| B | Hostaphat ® KW 340 D (Clariant) | 2.00% |
|   | Triceteareth-4 Phosphate |   |
|   | Plantasens ® Oat Serum (Clariant) | 3.00% |
|   | *Avena Sativa* (Oat) Kernel Oil (and) Phytosterols (and) *Olea Europaea* (Olive) Oil Unsaponifiables (and) Beeswax |   |
|   | Plantasens ® Shea Butter (Clariant) | 7.00% |
|   | *Butyrospermum Parkii* (Shea) Butter |   |
|   | Isopropyl Palmitate | 5.00% |
|   | *Macadamia Integrifolia* Seed Oil | 4.00% |
|   | *Cera Alba* (Beeswax) | 3.00% |
| C | Nipaguard ® SCP (Clariant) | 1.00% |
|   | Phenoxyethanol (and) Sorbitan Caprylate |   |
|   | Fragrance | 0.30% |
| D | Sodium Hydroxide | 0.10% |

Procedure:
I Mix ingredients of phase A and heat to 75° C.
II Mix ingredients of phase B and heat to 75° C.
III At Temperature, pour phase B into phase A and homogenize gently by using Ultra-Turrax.
IV Cool down under stirring.
V Below 40° C. add C and stir.
VI Adjust pH with D to 5.5.

Example Composition 18: Sprayable Hair Styling Gel

| A | Hybrid H | 0.90% |
|---|---|---|
| B | Water | Ad 100% |
| C | Genapol ® LA-230 (Clariant) Laureth-23 | 4.00% |
|   | Diaformer ® Z-632N (Clariant) Acrylates/Stearyl Acrylate/Ethylamine Oxide Methacrylate Copolymer | 4.50% |
|   | Dipropylene Glycol | 1.00% |
|   | Polyglykol 400 PEG-8 | 0.50% |
|   | Nipaguard ™ DMDMH (Clariant) DMDM Hydantoin | 0.50% |
|   | Panthenol | 0.50% |
| D | Emulsogen ® HCO 040 (Clariant) PEG-40 Hydrogenated Castor Oil | 0.50% |
|   | Fragrance | 0.30% |

Procedure:
I Add A to B while stirring. Stir until a smooth gel is formed.
II Add the components of C one after the other to I and stir until dissolved.
III Mix the components of D and add to II while stirring.

Example Composition 19: Conditioning Shampoo

| A | Water | Ad 100% |
|---|---|---|
|   | Hybrid H | 1.10% |
| B | Genapol ® LRO liquid (Clariant) Sodium Laureth Sulfate | 30.00% |
| C | Genagen ® CAB 818 (Clariant) Cocamidopropyl Betaine | 6.00% |
|   | XIAMETER ® PMX-200 Silicone Fluid 50 CS Dimethicone | 0.25% |
| D | Water | 10.00% |
|   | Jaguar ® 0-162 Hydroxypropyl Guar (and) Hydroxypropyl Guar Hydroxypropyltrimonium Chloride | 0.20% |
| E | Citric Acid | q.s. |
| F | Water | 4.00% |
|   | Sodium Benzoate | 0.45% |
| G | Sodium Chloride | 0.50% |

Procedure:
I Mix the ingredients of phase A and stir until dissolved.
II Add phase B and stir until homogeneous.
III Premix phase C and add to II while stirring.
IV Premix phase D and add to II while stirring.
V Adjust pH with E to 5.5 to 6.0.
VI Premix phase F and add to V, stir until dissolved.
VII Add phase G and stir until dissolved.

Methods of Use:
Example 19 is applied to wet hair. Tap water is employed to create a lather and spread the composition throughout the hair and scalp. The composition is immediately rinsed from the hair. The hair may further be conditioned.

Example Composition 20: Nail Varnish Remover Gel

| A | Water | Ad 100% |
|---|---|---|
|   | Ethanol | 27.00% |
|   | Polyglykol ® 400 (Clariant) PEG-8 | 3.00% |
|   | Glycerin | 3.00% |
|   | Aristoflex ® TAC (Clariant) Ammonium Acryloyldimethyltaurate/Carboxyethyl Acrylate Crosspolymer | 0.20% |
|   | Hybrid H | 1.00% |
| B | Ethyl Acetate | 30.00% |

Procedure:
I Add the components of A one after another and stir until homogenous.
II Add B into A and stir until completely dissolved.
III Add C to II.

Example Composition 21: Whitening Gel

| A | Genapol ® T 250 (Clariant) Ceteareth-25 | 2.00% |
|---|---|---|
|   | Genapol ® DAT 100 (Clariant) PEG-150 Polyglyceryl-2 Tristearate | 1.10% |
| B | Water | Ad 100% |
| C | Ascorbic Acid 2- Glucoside | 3.00% |
| D | Sodium Hydroxide | q.s. |
| E | Hybrid H | 1.50% |
|   | Nipaguard ™ DMDMH (Clariant) DMDM Hydantoin | 2.00% |

Procedure:
I Combine the ingredients of phase A and B while stirring and heating to 60° C.
II Cool to room temperature and add C.
III Adjust pH with D to 6.0.
IV Add E while stirring, continue stirring until homogeneous.

Example Composition 22: O/W Self Tanning Cream

| A | Hostaphat ® CC 100 (Clariant) Cetyl Phosphate | 1.00% |
|---|---|---|
|   | Glyceryl Stearate | 0.50% |
|   | Cetearyl Alcohol | 0.50% |
|   | Mineral Oil | 8.00% |
|   | Isopropyl Palmitate | 7.00% |
|   | Tocopheryl Acetate | 1.00% |
|   | SilCare ® Silicone 41M15 (Clariant) Caprylyl Methicone | 1.00% |
| B | Hybrid H | 2.00% |
| C | Water | ad 100% |
|   | Hostapon ® KCG (Clariant) Sodium Cocoyl Glutamate | 0.50% |
|   | Glycerin | 5.00% |
| D | Fragrance | 0.20% |
|   | Phenonip ™ ME (Clariant) Phenoxyethanol, Methylparaben, Ethylparaben | 1.00% |
| E | Dihydroxyacetone | 5.00% |
|   | Water | 8.00% |
|   | Sodium Hydroxide | q.s. |

Procedure:
I Melt A at 85° C.
II Stir B in A.
III Premix phase C and add to II, then stir until 30-35° C.
IV Add D to III.
V Dissolve Dihydroxyacetone in water and add E to IV.
VI Adjust pH to 4.0, if necessary Example Composition 23: Make Up Remover

| A | Water | ad 100% |
|---|---|---|
|   | Glycerin | 3.00% |
|   | Hybrid H | 0.80% |

-continued

| | | |
|---|---|---|
| B | Hostaphat ® KL 340 D (Clariant) | 3.00% |
| | Trilaureth-4 Phosphate | |
| | Cetearyl Alcohol | 1.50% |
| | Plantasens ® Olive LD (Clariant) | 2.00% |
| | Hydrogenated Ethylhexyl Olivate (and) | |
| | Hydrogenated Olive Oil Unsaponifiables | |
| | Isostearyl Isostearate | 4.00% |
| | Iso hexadecane | 4.00% |
| C | Sodium Hydroxide | q.s. |
| D | Nipaguard ® SCP (Clariant) | 1.00% |
| | Phenoxyethanol (and) Sorbitan Caprylate | |
| | Fragrance | 0.20% |

Procedure:
I Mix phase A and stir until dissolved then heat to 80° C.
II Combine ingredients of phase B separately and heat until 80° C.
III Pour II into I and homogenize gently by using Ultra-Turrax. Then cool to room temperature while stirring.
IV Adjust pH with C to 5.5.
V Add D and stir until homogeneous.
Example Composition 24: Insect Repellent Lotion

| | | |
|---|---|---|
| A | Diethyl Toluamide DEET | 10.00% |
| | Hostaphat ® KL 340 D (Clariant) | 1.00% |
| | Trilaureth-4 Phosphate | |
| | Isohexadecan | 5.00% |
| | C12-15 Alkyl Benzoate | 5.00% |
| | Cyclopentasiloxane | 2.00% |
| B | Hybrid H | 1.00% |
| C | Water | Ad 100% |
| | Ethanol | 10.00% |
| D | Fragrance | 0.30% |
| | Nipaguard ® POB (Clariant) | 0.80% |
| | Phenoxyethanol (and) Piroctone Olamine | |
| | (and) Benzoic Acid | |

Procedure:
I Mix the components of A.
II Stir the components of B into I.
III Then add C and stir well.
IV Finally add D and homogenize the emulsion.

The invention claimed is:

1. A water-soluble and/or water-swellable hybrid polymer comprising:
  (i) from 30 wt.-% to 95 wt.-% water-soluble and/or water-swellable polysaccharide polymer;
  (ii) from 5 wt.-% to 70 wt.-% synthetic polymer comprising:
    (a) from 90 mol-% to 99.9 mol-% of repeating units according to Formula (1)

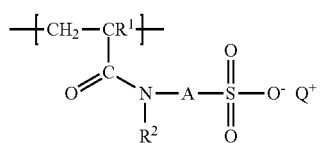

(1)

wherein
R$^1$ and R$^2$ are independently selected from the group consisting of H, methyl or ethyl; A is a linear or branched C$_1$-C$_{12}$-alkyl group; and Q$^+$ is H$^+$, NH$_4^+$, an organic ammonium ion [NHR$^5$R$^6$R$^7$]$^+$ wherein R$^5$, R$^6$, and R$^7$ independently of one another is hydrogen, a linear or branched alkyl group having 1 to 22 carbon atoms, a linear or branched, mono- or poly-unsaturated alkenyl group having 2 to 22 carbon atoms, a C$_6$-C$_{22}$ alkylamidopropyl group, a linear mono-hydroxy-alkyl group having 2 to 10 carbon atoms or a linear or branched dihydroxyalkyl group having 3 to 15 carbon atoms, and wherein at least one of the radicals R$^5$, R$^6$, and R$^7$ is not hydrogen, or Q$^+$ is Li$^+$, Na$^+$, K$^+$, ½ Ca$^{++}$, ½ Mg$^{++}$, ½ Zn$^{++}$, ⅓ Al$^{+++}$, or combinations thereof;
    (b) from 0.01 mol-% to 5 mol-% of crosslinking or branching units, wherein the crosslinking or branching units result from the incorporation of a monomer comprising at least two olefinically unsaturated double bonds;
  wherein components (i) and (ii) are polymerized by radical precipitation polymerization in a polar solvent.

2. The water-soluble and/or water-swellable hybrid polymer according to claim 1, wherein the monomers resulting in units (a) and/or (b) are/is neutralized with a base prior to the polymerization, and/or the hybrid polymer after polymerization is neutralized with a base.

3. The water-soluble and/or water-swellable hybrid polymer according to claim 2, wherein the base is selected from bases comprising an ion selected the group consisting of Li$^+$, Na$^+$, K$^+$, Ca$^{++}$, Mg$^{++}$, Zn$^{++}$, Al$^{+++}$, and combinations thereof.

4. The water-soluble and/or water-swellable hybrid polymer according to claim 1, wherein the repeating units according to Formula (1) result from the incorporation of a monomer selected from the group consisting of acryloyldimethyltaurates, acryloyl-1,1-dimethyl-2-methyltaurates, acryloyltaurates, acryloyl-N-methyltaurates, and combinations thereof.

5. The water-soluble and/or water-swellable hybrid polymer according to claim 1, wherein the crosslinking or branching units result from the incorporation of a monomer according to Formula (2)

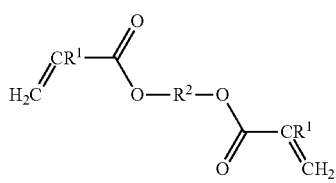

(2)

wherein,
R$^1$ is independently selected from H, methyl or ethyl; and
R$^2$ is a linear or branched alkyl group having 1 to 6 carbon atoms, or is a linear or branched, mono- or polyunsaturated alkylene group having 2 to 6 carbon atoms.

6. The water-soluble and/or water-swellable hybrid polymer according to claim 1, wherein the crosslinking or branching units result from the incorporation of a monomer according to Formula (3)

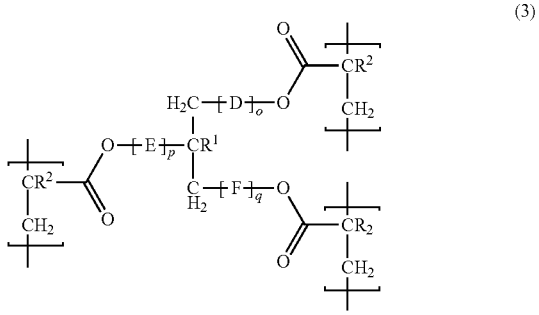

wherein, $R^1$ is independently selected from the group consisting of H, methyl or ethyl; and $R^2$ is a linear or branched alkyl group having 1 to 6 carbon atoms, or is a linear or branched, mono- or polyunsaturated alkylene group having 2 to 6 carbon atoms; D, E, and F are independently methyleneoxy (—CH$_2$O), ethyleneoxy (—CH$_2$—CH$_2$—O—), propyleneoxy (—CH(CH$_3$)—CH$_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and o, p, and q each independently are an integer from 1 to 50.

7. The water-soluble and/or water-swellable hybrid polymer according to claim 1, wherein the crosslinking or branching units result from the incorporation of a crosslinker selected from the group consisting of methylenebisacrylamide; methylenebismethacrylamide; esters of unsaturated monocarboxylic and polycarboxylic acids with polyols, allyl esters of phosphoric acid;
and vinylphosphonic acid derivatives.

8. The water-soluble and/or water-swellable hybrid polymer according to claim 1, wherein the polysaccharide polymer is selected from the group consisting of xanthan gum, carrageenan, guar gum, chitosan and alginate.

9. The water-soluble and/or water-swellable hybrid polymer according to claim 1, wherein the polysaccharide polymer comprises glucose and/or galactose units.

10. The water-soluble and/or water-swellable hybrid polymer according to claim 1, wherein the structure of the hybrid polymer is such that the polysaccharide polymer is a backbone onto which the synthetic polymer is grafted.

11. The water-soluble and/or water-swellable hybrid polymer according to claim 1, wherein the radical precipitation polymerization is carried out in a polar solvent mixture comprising: I) water and II) a further compound.

12. A composition comprising:
at least one water-soluble and/or water-swellable hybrid polymer according to claim 1 and
(ii) at least one carrier.

13. The composition according to claim 12, wherein the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

14. A thickening agent, a structurant, and/or a rheology modifier comprising at least one water-soluble and/or water-swellable hybrid polymer according to claim 1.

15. A process for thickening, adding structure to, and/or modifying a rheology of a composition comprising the step of adding at least one water-soluble and/or water-swellable hybrid polymer comprising:
(i) from 30 wt.-% to 95 wt.-% water-soluble and/or water-swellable polysaccharide polymer;
(ii) from 5 wt.-% to 70 wt.-% synthetic polymer comprising:
(a) from 90 mol-% to 99.9 mol-% of repeating units according to Formula (1)

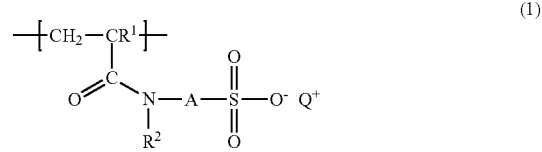

wherein
$R^1$ and $R^2$ are independently selected from the group consisting of H, methyl or ethyl; A is a linear or branched $C_1$-$C_{12}$-alkyl group; and $Q^+$ is $H^+$, $NH_4^+$, an organic ammonium ion $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear mono-hydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof;
(b) from 0.01 mol-% to 5 mol-% of crosslinking or branching units, wherein the crosslinking or branching units result from the incorporation of a monomer comprising at least two olefinically unsaturated double bonds;
wherein components (i) and (ii) are polymerized by radical precipitation polymerization in a polar solvent, to the composition.

* * * * *